US008410045B2

(12) United States Patent
Michel et al.

(10) Patent No.: US 8,410,045 B2
(45) Date of Patent: Apr. 2, 2013

(54) CAMPTOTHECIN-PEPTIDE CONJUGATES AND PHARMACEUTICAL COMPOSITIONS CONTAINING THE SAME

(75) Inventors: Matthieu Michel, Le Vésinet (FR); Denis Ravel, Paris (FR); Fabien Ribes, Marseille (FR); Isabelle Tranchant, Le Kremlin-Bicêtre (FR)

(73) Assignee: Drais Pharmaceuticals, Inc., Bridgewater, NJ (US)

( * ) Notice: Subject to any disclaimer, the term of this patent is extended or adjusted under 35 U.S.C. 154(b) by 897 days.

(21) Appl. No.: 12/295,508

(22) PCT Filed: Mar. 30, 2007

(86) PCT No.: PCT/IB2007/001697
§ 371 (c)(1),
(2), (4) Date: Aug. 18, 2009

(87) PCT Pub. No.: WO2007/113687
PCT Pub. Date: Oct. 11, 2007

(65) Prior Publication Data
US 2010/0015136 A1    Jan. 21, 2010

Related U.S. Application Data

(60) Provisional application No. 60/792,312, filed on Apr. 17, 2006.

(30) Foreign Application Priority Data

Mar. 30, 2006    (EP) .................................... 06290500

(51) Int. Cl.
*A61K 38/10*    (2006.01)
*A61K 38/16*    (2006.01)
*C07D 405/14*    (2006.01)
*C07K 7/08*    (2006.01)
*C07K 14/00*    (2006.01)

(52) U.S. Cl. ........ 514/1.2; 514/1.3; 514/19.3; 514/19.4; 530/326; 530/327; 530/345; 546/48

(58) Field of Classification Search .................... None
See application file for complete search history.

(56) References Cited

U.S. PATENT DOCUMENTS

| 4,604,463 A | 8/1986 | Miyasaka et al. |
| 7,104,894 B2 | 9/2006 | Bennett |
| 2006/0014712 A1 | 1/2006 | Neuman |

FOREIGN PATENT DOCUMENTS

| EP | 0056692 | 7/1982 |
| EP | 0088642 | 9/1983 |
| EP | 0074256 | 11/1986 |
| EP | 0137145 | 4/1988 |
| EP | 0325247 | 5/1993 |
| EP | 0296612 | 6/1994 |
| EP | 0540099 | 4/1996 |
| EP | 0321122 | 9/1996 |
| EP | 0737686 | 7/1999 |
| EP | 1101765 | 8/2002 |
| EP | 1 512 696 A1 | 3/2005 |
| EP | 1 526 183 A2 | 4/2005 |
| WO | 90/03169 | 4/1990 |
| WO | 96/37496 | 11/1996 |
| WO | 96/38146 | 12/1996 |
| WO | 96/38449 | 12/1996 |
| WO | 97/00876 | 1/1997 |
| WO | WO 99/07414 A1 | 2/1999 |
| WO | 99/09996 | 3/1999 |
| WO | WO-99/17804 A1 | 4/1999 |
| WO | 99/65493 | 12/1999 |
| WO | WO 00/01417 A1 | 1/2000 |
| WO | 00/45831 | 8/2000 |
| WO | 00/53607 | 9/2000 |
| WO | 01/64738 | 9/2001 |
| WO | WO-01/64738 A2 | 9/2001 |
| WO | WO-01/70275 A2 | 9/2001 |
| WO | WO 02/02595 A1 | 1/2002 |
| WO | WO 03/018636 A2 | 3/2003 |
| WO | WO-03/031467 A2 | 4/2003 |
| WO | WO-03/097356 A1 | 11/2003 |
| WO | WO-03/103596 A2 | 12/2003 |
| WO | WO 2004/005339 A2 | 1/2004 |
| WO | WO-2004/035032 A2 | 4/2004 |
| WO | WO 2005/016960 A2 | 2/2005 |
| WO | WO 2005/016960 A3 | 2/2005 |

OTHER PUBLICATIONS

De Coupade et al., "Novel human-derived cell-penetrating peptides for specific subcellular delivery of therapeutic biomolecules", Biochemical Society, vol. 390, (2005), pp. 407-418, XP002400383.
Xu et al., "Interaction of Heparin with Synthetic Peptides Corresponding to Thec-Terminal Domain of Intestinal Mucins", Glycoconjugate Journal, Lund, Se, vol. 13, No. 1, (1996), pp. 81-90, XP001042193.
International Search Report PCT/IB2007/001697, mailed on Feb. 12, 2008.
Alimonti et al, (2004) "New approaches to prevent intestinal toxicity of irinotecan-based regimens" Cancer Treatment Rev. 30:555-562.
Chabot (1997) "Clinical pharmacokinetics of irinotecan" Clin. Pharmacokinetics 33:245-259.
Charasson et al. (2002) "Determination of drug interactions occurring with the metabolic pathways of irinotecan" Drug Metab. Dispos. 30:731-733.
Gottlieb et al. (1970) "Preliminary pharmacologic and clinical evaluation of camptothecin sodium (NSC-100880)" Cancer Chemother. Rep. 54:461-470.

(Continued)

Primary Examiner — Jeffrey E Russel
(74) Attorney, Agent, or Firm — Goodwin Procter LLP

(57) ABSTRACT

The present invention relates to a novel compound of use in the improved delivery of therapeutic drug agents into target cells or tissues, composition comprising the same and uses thereof. The compound is more specifically a conjugate of a peptide moiety and a camptothecin, a derivative or analog thereof which provides numerous benefits, including enhancement in terms of aqueous solubility, pharmacokinetics and tissue distribution, enlargement of the therapeutic index, and limitation of the inter-patient metabolic variability, as well as improvement of delivery of the biologically active ingredient to the target cells or tissues.

14 Claims, 1 Drawing Sheet

OTHER PUBLICATIONS

Gupta et al. (1994) "Metabolic Fate of Irinotecan in Humans: Correlation of Glucuronidation with Diarrhea" Cancer Res. 54:3723-3725.
Horikawa et al. (2002) "Reduced gastrointestinal toxicity following inhibition of the biliary excretion of irinotecan and its metabolites by probenecid in rats" Pharmaceutical Res. 19:1345-1353.
Hsiang et al. (1985) "Camptothecin Induces Protein-linked DNA Breaks via Mammalian DNA Topoisomerase I" J. Biol. Chem. 260:14873-14878.
Kawato et al. (1991) "Intracellular Roles of SN-38, a Metabolite of the Camptothecin Derivative CPT-11, in the Antitumor Effect of CPT-11" Cancer Res. 51:4187-4191.
Kehrer et al. (2001) "Modulation of Irinotecan-induced Diarrhea by Cotreatment with Neomycin in Cancer Patients" Clin. Cancer Res. 7:1136-1141.
Kraut et al. (2004) "Pharmacogenomic and pharmacokinetic assessment of liposome encapsulated SN-38 (LE-SN38) in advanced cancer patients" ASCO Abstract No. 2501.
Moertel et al. (1972) "Phase II study of camptothecin (NSC-100880) in the treatment of advanced gastrointestinal cancer" Cancer Chemother. Rep. 56:95-101.
Nakagawa et al. (2006) "Molecular modeling of new camptothecin analogues to circumvent ABCG2-mediated drug resistance in cancer" Cancer Letters 2006 234(1):81-9.
Ohe et al. (1992) "Phase I study and pharmacokinetics of CPT-11 with 5-day continuous infusion" J. Natl. Cancer Inst. 84:972-974.
Rothenberg et al. (1993) "Phase I and pharmacokinetic trial of weekly CPT-11" J. Clin. Oncology 11: 2194-2204.
Satoh et al. (1994) "Metabolic activation of CPT-11, 7-ethyl-10[4-(1-piperidino)-1-piperidino]carbonyloxycamptothecin, a novel antitumor agent, by carboxylesterase" Biol. Pharm. Bull. 17:662-664.
Senter et al. (2001) "Identification and activities of human carboxylesterases for the activation of CPT-11, a clinically approved anticancer drug" Bioconjug. Chem. 12: 1074-1080.
Slatter et al. (2000) "Pharmacokinetics, metabolism, and excretion of irinotecan (CPT-11) following I.V. infusion of [$^{14}$C]CPT-11 in cancer patients" Drug Metab. Dispos. 28:423-433.
Van Cutsem et al. (2005) "Optimisation of irinotecan dose in the treatment of patients with metastatic colorectal cancer after 5-FU failure: results from a multinational, randomised phase II study" Br. J. Cancer. 92:1055-1062.
Wall et al. (1966) "Plant Antitumor Agents. I. The Isolation and Structure of Camptothecin, a Novel Alkaloidal Leukemia and Tumor Inhibitor from Camptotheca acuminate" J. Amer. Chem. Soc. 88:3888-3890.
Xie et al. (2002) "Clinical pharmacokinetics of irinotecan and its metabolites in relation with diarrhea" Clin. Pharmacol. Ther. 72:265-275.
Xu et al. (2002) "Human Carboxylesterase 2 Is Commonly Expressed in Tumor Tissue and Is Correlated With Activation of Irinotecan" Clin. Cancer Res. 8:2605-2611.
Ychou et al. (2002) "High-dose, single-agent irinotecan as first-line therapy in the treatment of metastatic colorectal cancer" Cancer Chemother. Pharmacol. 50:383-391.
Amara et al., (1999), "Stromal cell-derived factor-1α associates with heparan sulfates through the first β-strand of the chemokine," J. Biol. Chem., 274(34):23916-23925.
Arkonac et al., (1998), "Vascular endothelial growth factor induces heparin-binding epidermal growth factor-like growth factor in vascular endothelial cells," J. Biol. Chem., 273(8):4400-4405.
Avrameas et al., (1998), "Polyreactive anti-DNA monoclonal antibodies and a derived peptide as vectors for the intracytoplasmic and intranuclear translocation of macromolecules," Proc. Natl. Acad. Sci. USA, 95:5601-5606.

Campanelli et al., (1996), "Alternative RNA splicing that determines agrin activity regulates binding to heparin and α-dystroglycan," Development, 122(5)1663-1672.
Cardin et al., (1988), "Inhibition of lymphocyte proliferation by synthetic peptides homologous to human plasma apolipoproteins B and E," Biochem. Biophys. Res. Commun., 154(2):741-745.
Derossi et al., (1996), "Cell internalization of the third helix of the antennapedia homeodomain is receptor-independent," J. Biol. Chem., 271(30):18188-18193.
Elliott et al., (1997), "Intercellular trafficking and protein delivery by a herpesvirus structural protein," Cell, 88 (2):223-233.
Fowlkes et al., (1997), "Heparin-binding, highly basic regions within the thyroglobulin type-1 repeat of insulin-like growth factor (IGF)-binding proteins (IGFBPs) -3, -5, and -6 inhibit IGFBP-4 degradation," Endocrinology, 138 (6):2280-2285.
Fromm et al., (1997), "Pattern and spacing of basic amino acids in heparin binding sites," Arch. Biochem. Biophys., 343(1):92-100.
Futaki et al., (2003), "Membrane permeability commonly shared among arginine-rich peptides," J. Mol. Recognit., 16 (5):260-264.
Hasan et al., (1999), "IL-12 is a heparin-binding cytokine," J. Immunol, 162:1064-1070.
Hirabayashi et al., (1993), "Human B-cell clones expressing lupus nephritis-associated anti-DNA idiotypes are preferentially expanded without somatic mutation," Scand. J. Immunol., 37(5):533-540.
Inoue et al., (1990), "Inhibition of oxygen toxicity by targeting superoxide dismutase to endothelial cell surface," FEBS Lett., 269(1):89-92.
Jans, (1994), "Nuclear signaling pathways for polypeptide ligands and their membrane receptors?," FASEB J., 8:841-847.
Kalsi et al., (1995), "Analysis of three new idiotypes on human monoclonal autoantibodies," Lupus, 4(5):375-389.
Kaneda et al., (1997), "Plasma pharmacokinetics of 7-ethyl-10-hydroxycamptothecin (SN-38) after intravenous administration of SN-38 and irinotecan (CPT-11) to rats," Biol. Pharm. Bull., 20(9):992-996.
Kokryakov, (1993), "Protegrins: leukocyte antimicrobial peptides that combine features of corticostatic defensins and tachyplesins," FEBS Lett., 327(2):231-236.
Lortat-Jacob et al., (1991), "Interferon-gamma binds to heparan sulfate by a cluster of amino acids located in the C-terminal part of the molecule," FEBS Lett., 280(1):152-154.
Maher et al., (1989), "The alternatively spliced exon of the platelet-derived growth Factor A chain encodes a nuclear targeting signal," Mol. Cell. Biol., 9(5):2251-2253.
Pohl et al., (1990), "Amino acid sequence of CAP37, a human neutrophil granule-derived antibacterial and monocyte-specific chemotactic glycoprotein structurally similar to neutrophil elastase," FEBS Lett., 272(1-2):200-204.
Ruben et al., (1989), "Structural and functional characterization of human immunodeficiency virus tat protein," J. Virol., 63(1):1-8.
Stevenson et al., (1993), "Utilization of the VH4-21 gene segment by anti-DNA antibodies from patients with systemic lupus erythematosus," J. Autoimmun., 6(6):809-825.
Weisgraber et al., (1987), "Human apolipoprotein B-100 heparin-binding sites," J. Biol. Chem., 262(23):11097-11103.
Yayon et al., (1991), "Cell surface, heparin-like molecules are required for binding of basic fibroblast growth factor to its high affinity receptor," Cell, 64(4):841-848.
Zorko et al., (2005), "Cell-penetrating peptides:mechanism and kinetics of cargo delivery," Advanced Drug Delivery Reviews, 57:529-545.
Zuckermann et al., (1992), "Efficient method for the preparation of peptoids [Oligo(N-substituted glycines)] by Submonomer Solid-Phase Synthesis," J. Am. Chem. Soc., 114:10646-10647.

CAMPTOTHECIN-PEPTIDE CONJUGATES AND PHARMACEUTICAL COMPOSITIONS CONTAINING THE SAME

CROSS-REFERENCE TO RELATED APPLICATIONS

This application is the U.S. national stage application of International Application No. PCT/IB2007/001697, filed on Mar. 30, 2007, which claims the benefit of European Patent Application No. 06 290500.5, filed Mar. 30, 2006 and U.S. Provisional Appl. Ser. No. 60/792,312, filed Apr. 17, 2006, both of which are incorporated by reference herein in their entirety.

SEQUENCE LISTING

The instant application contains a Sequence Listing which has been submitted in ASCII format via EFS-Web and is hereby incorporated by reference in its entirety. Said ASCII copy, created on Jul. 26, 2012, is named DRA-001.txt and is 12,698 bytes in size.

The present invention relates to a novel compound of use in the improved delivery of therapeutic drug agents into target cells or tissues, composition comprising the same and uses thereof. The compound is more specifically a conjugate of a peptidic moiety and a camptothecin, a derivative or analog thereof which provides numerous benefits, including enhancement in terms of aqueous solubility, pharmacokinetics and tissue distribution, enlargement of the therapeutic index, and limitation of the inter-patient metabolic variability, as well as improvement of delivery of the biologically active ingredient into the target cells or tissues.

BACKGROUND OF THE INVENTION

Camptothecin (CPT) is an alkaloid extracted from *Camptotheca acuminata* tree that was discovered in the 1960s (Wall et al, J. Amer. Chem. Soc. 88: 3888-3890 (1966)). This water insoluble molecule showed a very powerful anti-tumoral activity but its utilization in the clinic was limited due to very strong bladder toxicity and severe diarrhea (Gottlieb et al, Cancer Chemother. Rep. 54:461-470 (1970), Moertel et al, Cancer Chemother. Rep. 56:95-101(1972)). Structure-activity studies have identified two hydrosoluble anti-neoplastic derivatives that are currently on the market: irinotecan (CPT-11, Campto®, Camptosar®) and topotecan (Hycamtin®, a water-soluble camptothecin derivative). These two molecules are specific inhibitors of DNA topoisomerase I, that induce single strand breaks in DNA which then blocks DNA replication (Hsiang et al, J. Biol. Chem. 260:14873-14878 (1985), Kawato et al, Cancer Res. 51:4187-4191 (1991), Satoh et al, Biol. Pharm. Bull. 17:662-664 (1994)).

Irinotecan is a water soluble prodrug of SN38 (7-ethyl-10-hydroxy-camptothecin), the active metabolite which is released after hepatic enzymatic cleavage of irinotecan. SN38 is a powerful topoisomerase I inhibitor and is at least 2000-fold more active than irinotecan as an anti-proliferative agent. However, SN38 is highly water insoluble and requires delivery systems to allow its adequate administration and bioavailability. As with many camptothecin derivatives, SN38 contains a lactone ring which is highly important for anti-tumoral efficacy. This lactone ring is unstable at physiological or basic pH, resulting in the conversion of the active drug to the inactive carboxylate form (Chabot, Clin. Pharmacokinetics, 33: 245-259 (1997)).

Irinotecan is widely used for the treatment of colon cancer. However, it encounters several limitations. After administration, irinotecan has to be converted to SN38 to be active. The hepatic enzymatic conversion of irinotecan into the active drug SN38 is very partial in humans (Rohtenberg et al, J. Clin. Oncology 11: 2194-2204 (1993), Senter et al, Bioconjugate Chem. 12: 1074-1080 (2001)). Only 2 to 8% of the administered doses of irinotecan are cleaved by hepatic and tumor carboxylesterases (CES) to the lipophilic metabolite SN38 (Senter et al, Bioconjugate Chem. 12: 1074-1080 (2001), Xu et al, Clin. Cancer Res.8:2605-2611 (2002)). Analyses of the kinetics of this catabolism have demonstrated substantial inter-patient heterogeneity due to genetic and environmental factors which influence the enzyme activity by up to ten times (Charasson et al, Drug Metab. Dispos. 30:731-733 (2002)). This leads to a high level of inter-individual variability in the metabolism of irinotecan and influences the tolerance and efficacy of irinotecan and significantly complicates patient's care. (Ohe et al, J. Natl. Cancer Inst. 84:972-974 (1992), Gupta et al, Cancer Res. 54:3723-3725 (1994), Slatter et al, Drug Metab. Dispos. 28:423-433 (2000), Kraut et al, ASCO abstract No: 2501, 2004). SN38 is further converted (detoxified) to SN38-Glucuronide (SN38-G), an inactive glucuronoconjugate, in the liver by uridine diphosphate glucuronosyl transferase 1A1 (UGT1A1). Glucuronidation renders the molecule hydrophilic which permits its gastro-intestinal excretion via the bile. Once in the intestine, SN38-G is reconverted to SN38 by the intestinal bacterial flora (beta-Glucuronidase enzyme). Irinotecan itself is mainly excreted into bile (>26%) and can be converted to SN38 by intestinal CES (M. Horikawa, Pharmaceutical Res., 19: 1345-1353 (2002)). This local accumulation of SN38 in the intestine is responsible for the high level of delayed intestinal toxicity (diarrhea) observed following irinotecan treatment, which is one of irinotecan's main dose-limiting toxicities (Xie et al, Clin. Pharmacol. Ther; 72: 265-275 (2002), Alimonti et al, Cancer Treatment Rev. 30: 55-562 (2004)). The delayed diarrhea is severe (e.g., life threatening) and sometimes appears together with fever. Another significant toxicity of irinotecan is leucopenia (e.g., neutropenia). Haematological disorders may result in severe aplasia sometimes complicated by systemic infections. These severe side effects observed after treatment result in supplementary hospital care for the patients (longer hospital stay; anti-diarrhea treatment; prophylactic antibiotics therapy) (Kehrer et al, Clin. Cancer Res. 7: 1136-1141 (2001)). It has been shown in clinical trials that dose escalation/intensification of irinotecan gives an improved therapeutic response. This dose-effect has been proven in patients with colorectal metastatic cancers (Ychou et al, Cancer Chemother. Pharmacol. 50:383-391 (2002), Van Cutsem et al, Br. J. Cancer. 92:1055-1062 (2005)). However, the severe side effects described above limit the doses that can be administered to an individual, reducing irinotecan's potential efficacy.

Repeated exposition of human cancers to camptothecin derivatives can lead to the development of drug resistance (Nakagawa et al, Cancer Letters in press (2005)). This characteristic induces a decrease of efficacy not only after treatment with camptothecin derivatives but also with other commonly used anti-cancer agents.

Thus, there is a substantial interest in the development of adequate delivery systems to overcome the limitations of camptothecin derivatives (e.g. SN38), described above.

Different strategies have been proposed for delivery of camptothecin derivatives, such as liposomal formulations of SN38 (described in PCT patent application published under No WO 2004/035032 filed by NEOPHARM), nanoparticle formulations of SN38 (described in PCT patent application published under No WO 03/103596 filed by IMARX), polyglutamic acid-camptothecin conjugates (described in PCT patent application published under No WO 01/70275 filed by CELL THERAPEUTICS) or polymeric derivatives of camptothecin such as PEG-camptothecin conjugates (described in PCT patent applications published under No WO 03/097356 filed by ENZON and No WO 03/031467 filed by DEBIO) or polymeric conjugates of 20-O-[glycyl-aminoacyl-glycyl]-camptothecins (described in PCT patent application published under No WO 99/17804 filed by PHARMACIA & UPJOHN).

Peptidic drug delivery systems have also been described in PCT patent application published under No WO 00/01417 filed by CYCLACEL aiming to facilitate the delivery of different drugs, such as the 10-Hydroxycamptothecin. This patent application describes the use of homeobox peptide derived from the *Drosophila antennapedia* homoprotein (preferably a cell-penetrating peptide (CPP) named penetratin) for conjugation to a number of cytotoxic drugs, thus enhancing their delivery and/or therapeutic effect. However, this patent application does not show any in vitro or in vivo experiments carried out with the conjugates. Consequently the applicant has performed in vitro human serum stability studies using the conjugate described in example 29 of this patent application No WO 00/01417. These studies showed that the half life time (stability) of this conjugate is less than three minutes which does not appear sufficient for intracellular delivery of therapeutically effective amounts of the camptothecin derivative in vivo.

PCT patent application published under No. WO 01/64738 filed by DIATOS relates to amino acid sequences which react with aminoglycans and transfer a broad range of active substances (i.e. nucleic acids, proteins, drugs, antigens or antibodies) from the outside medium to the inside of cells, and more specifically cell nuclei. Such sequences derive from human proteins and are therefore non-immunogenic cell-penetrating peptides (CPP) when administered to a human in need of therapeutic treatments.

There is consequently a need in enhanced delivery efficiency, safety and efficacy of the active compound (e.g., SN38).

Within the framework of research that has lead to this invention, the applicant synthesized different CPP-camptothecin derivative conjugates. These conjugates were then evaluated in vitro and in vivo for their stability, efficacy and toxicity.

In particular, an object of the invention is to provide a compound which alleviates or decreases the drawbacks and undesired side-effects described above for camptothecin derivatives, such as for irinotecan. In particular, the present invention aims to provide a compound which is able to improve solubility of the biologically active agent in pharmaceutically acceptable forms, have sufficient stability to allow an effective intracellular delivery, reduce toxic or non-desirable side-effects, enhance the onset of action of the desired therapeutic effect, provide alternative routes for the administration of the drug, reduce inter-patient variability, and/or modify the tissue distribution and metabolism of the drug.

SUMMARY OF THE INVENTION

According to a first aspect, the invention relates to a conjugate comprising a drug moiety linked to a carrier moiety, wherein said carrier moiety comprises a peptide or analog thereof facilitating penetration into a cell or tissue of a payload (e.g., a drug moiety) and having the ability to increase solubility, modify the pharmacokinetics, metabolism and tissue distribution properties of the drug, and/or decrease the incidence of drug resistance, and the drug moiety is any camptothecin, analog or derivative thereof. Said peptide or analog thereof is also called herein a Cell Penetrating Peptide (CPP).

The invention also relates to a pharmaceutical composition comprising such conjugate and therapeutic uses thereof, in particular for the treatment of various types of diseases, including cancers.

DETAILED DESCRIPTION OF THE INVENTION

Figure 1:
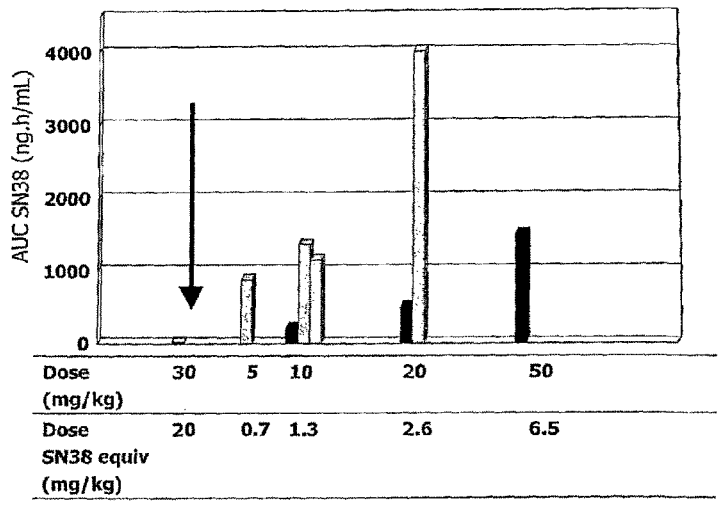
FIG. 1 shows the blood AUC of SN38 following infusion of DPV1047-MIC-SN38 (10, 20, 50 mg/kg, black bars), DPV1047-BCH-SN38 (5, 10 (n=2), 20 mg/kg, grey bars) and of irinotecan (at 30 mg/kg, white bar) in the dog.

According to a particular embodiment, the invention provides a conjugate comprising at least one camptothecin, analog or derivative thereof and more preferably the compound SN38, linked to a carrier moiety, preferably via a linker group.

The carrier moiety comprises a peptide or analog thereof facilitating penetration into a cell or tissue of a payload (e.g., a drug moiety), and having the ability to increase solubility of the drug moiety, modify the pharmacokinetics, metabolism and tissue distribution properties of the drug moiety, reduce inter-patient variability, and/or decrease the incidence of drug resistance.

The conjugates of the invention include their salts, optical and geometrical isomers or mixtures thereof.

The salts of the conjugates are in particular basic or acid addition salts, preferably compatible with a pharmaceutical use. Among the pharmaceutically acceptable inorganic acids, non-limiting examples include hydrochloric, hydrobromic, sulfuric, phosphoric, and nitric. Among the pharmaceutically acceptable organic acids, non-limiting examples include acetic, trifluoroacetic, lactic, pyruvic, malonic, succinic, glutaric, fumaric, tartaric, maleic, citric, benzoic, ascorbic, methane sulfonic, ethane sulfonic, 2-hydroxyethanesulfonic and camphoric acid. Among the pharmaceutically acceptable bases, non-limiting examples include sodium hydroxide, potassium hydroxide, triethylamine and tert-butylamine. Preferably, the conjugate of the invention is in a hydrochloric salt form.

Advantageously, the conjugation of the carrier moiety to the drug (i.e. camptothecin derivative) leads to modification of the pharmacokinetic behaviour of the drug, compared to the non-conjugated drug.

Advantageously, the carrier moiety comprises positively charged moieties (i.e. basic amino acids) inducing a low pH in aqueous solution (e.g. <6.5 pH value) of the conjugate. This acidic pH favours the stabilisation of the lactone group on the camptothecin derivative in the pharmaceutical composition (lactone form >95%) and, thus, allows a plasmatic equilibrium between lactone and carboxylate forms in favour of lactone form (>about 55% lactone form) after injection to a living animal or human individual (Kaneda et al., Biol. Pharm. Bull. 20: 992-996 (1997)).

Another advantage of the present invention is that the tissue distribution and thus the in vivo metabolism of the drug is also altered (i.e., modified) by its conjugation to the carrier moiety. Modification of the metabolism includes cleavage of the conjugate of the present invention by plasmatic as well as tissular esterases, as compared to hepatic carboxylesterases for irinotecan activation. Taken together, the modified tissue distribution (i.e. a decrease in hepatic uptake) and the delivery system of the invention avoiding the need for hepatic activation of the conjugate of the invention, lead to a decrease in the interindividual variability of the treatment and a decrease in intestinal toxicity (compared to irinotecan), with furthermore delivery of more than 60% the active metabolite (i.e., the drug in its therapeutic active form) e.g., SN38.

Advantageously, the conjugate of the invention presents sufficient stability to allow the delivery of a therapeutically effective amount of circulating and cellular camptothecin, analogs or derivatives thereof. Preferably, the conjugate of the invention comprises at least one camptothecin, analog or derivative thereof linked to a carrier moiety, via a linker group, wherein the carrier moiety is a cell penetrating peptide and wherein the half life time of the conjugate in human plasma at 37° C. in vitro (i.e. time to have 50% by mole of free camptothecin, analogs or derivatives thereof released by the conjugates of the invention) is equal or superior to 5 minutes.

The terms "conjugate" or "conjugated" refer to a covalent, ionic, or hydrophobic interaction whereby the moieties of a molecule are held together and preserved in proximity.

The term "reacted" has the ordinary meaning for one skilled in the art of chemistry.

The terms "linker" or "crosslinker" are used interchangeably herein and refer to a chain conjugating/linking two moieties together and comprising one or more atoms.

The term "in vitro" has its art recognized meaning, e.g., cell culture, involving purified reagents or extracts, e.g., cell extracts. The term "in vivo" also has its art recognized meaning, e.g., involving living cells in an organism, and/or any cells in an organism.

The term "pharmacokinetics" means the process by which a drug is absorbed, distributed, metabolized, and eliminated by the body. The pharmacokinetic behaviour is generally evaluated from the evolution of blood, plasma or serum concentration of a drug and its metabolites as a function of time. The observation time can be comprised between about 5 minutes and about 24 hours or more. The term "plasma pharmacokinetics" refers to the evolution of the blood, plasma or serum concentration of a drug and its metabolite over time.

The term "tissue distribution" is defined as the relative or absolute exposure of different tissues, namely liver, lung, stomach, intestine, pancreas, brain, bladder, ovary, testis, prostate, uterus, skin, muscle, spleen, lymph nodes, tumors, or any other relevant organ to a drug or its metabolites at a defined time. Tissue distribution is determined from the evolution of the drug or metabolite concentration in tissues as a function of time.

The term "peptide(s)" refer to a polymer of amino acids of which the written convention is N, or amino, terminus is on the left and the C, or carboxyl, terminus is on the right. The 20 most common, natural L-amino acids are alternatively designated by three-letter or one-letter codes. Peptides, as used herein, are considered to include "peptide analogs", structural modifications containing one or more modifications to L-amino acid side-chains or to the alpha-amino acid backbone. An example of a backbone modified peptide analog is the N-methyl glycine "peptoid" (Zuckermann et al., J. Amer. Chem. Soc. 114:10646-47 (1992)).

The term "cell penetrating peptide(s)" (CPP(s)) is defined as a carrier peptide that is capable of crossing biological membrane or a physiological barrier. Cell penetrating peptides are also called cell-permeable peptides, protein-transduction domains (PTD) or membrane-translocation sequences (MTS). CPPs have the ability to translocate in vitro and/or in vivo the mammalian cell membranes and enter into cells and/or cell nuclei, and directs a conjugated compound of interest, such as a drug or marker, to a desired cellular destination. Accordingly, the CPP can direct or facilitate penetration of a compound of interest across a phospholipid, mitochondrial, endosomal or nuclear membrane. The CPP can also direct a compound of interest from outside the cell through the plasma membrane, and into the cytoplasm or cytosol or to a desired location within the cell, e.g., the nucleus, the mitochondria, the endoplasmic reticulum, a lysosome, or a peroxisome. Alternatively or in addition, the CPP can direct a compound of interest across the blood-brain or hematoretinal, trans-mucosal, skin, gastrointestinal and/or pulmonary barriers. Several proteins and their peptide derivatives have been found to possess cell internalization properties including but not limited to the Human Immunodeficiency Virus type 1 (HIV-1) protein Tat (Ruben et al J. Virol. 63, 1-8 (1989)), the herpes virus tegument protein VP22 (Elliott and O'Hare, Cell 88, 223-233 (1997)), Penetratin (Derossi et al, J. Biol. Chem. 271, 18188-18193 (1996)), protegrin 1 (PG-1) anti-microbial peptide SynB (Kokryakov et al., FEBS Lett. 327, 231-236 (1993)) and the basic fibroblast growth factor (Jans, Faseb J. 8, 841-847 (1994)). These carrier peptides show little sequence homology with each other, but are all highly cationic and arginine or lysine rich. Indeed, synthetic poly-arginine peptides have been shown to be internalized with a high level of efficiency (Futaki et al., J. Mol. Recognit. 16, 260-264 (2003); Suzuki et al., J. Biol. Chem. (2001)).

Consequently, in a particular embodiment, the conjugate of the invention presents a CPP selected from Human Immunodeficiency Virus type 1 (HIV-1) protein Tat, the herpes virus tegument protein VP22, Penetratin, protegrin 1 (PG-1) antimicrobial peptide SynB, the basic fibroblast growth factor, synthetic poly-arginine peptide, or peptide derivative thereof possessing cell internalization properties.

According to a particular aspect of the invention, the CPP comprises an amino acid sequence having the following formula (I):

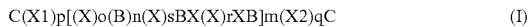

$$C(X1)_p[(X)_o(B)_n(X)_sBX(X)_rXB]_m(X2)_qC \qquad (I)$$

wherein

X1 and X2 are independently amino acid sequences of 1 to 20 amino acids; p and q independently are whole numbers between 0 and 5, preferably 0 or 1;

B is independently a basic amino acid, X is independently a non-basic amino acid;

C is independently nothing or any moiety comprising a thioether bond linked to the remainder of the conjugate, preferably the moiety is a cysteine or cysteamine;

m is 1 or 2;

n is 1, 2 or 3;

o is 0 or 1;

r is 0 or 1;

s is 0, 1, 2 or 3.

In a preferred embodiment, the CPP is derived from human proteins, thus avoiding the immunogenicity when administered to humans. According to said particular embodiment, the CPP is a peptide comprising an amino acid sequence represented by formula (I) as defined above.

In a more preferred embodiment, CPPs of the present invention are also able to solubilize highly lipophilic molecules and/or to modify their pharmacokinetics and tissue distribution compared to said molecule non-conjugated to a CPP of the present invention.

In a particular embodiment, the carrier moiety according to the invention comprises a CPP capable of reacting in vitro and/or in vivo with cell surface glycosaminoglycans. Such CPPs were described in the PCT patent applications No WO 01/64738 and No WO 05/016960 filed by DIATOS and in De Coupade et al. (Biochem J. 390:407-18 (2005)). These peptides are amino acid sequences originating from human heparin binding proteins and/or anti-DNA antibodies selected from the group comprising: the lipoproteins such as human apolipoprotein B or E (Cardin et al., Biochem. Biophys. Res. Com. 154: 741 (1988)), the agrine (Campanelli et al., Development 122: 1663-1672 (1996)), the insulin growth factor binding protein (Fowlkes et al., Endocrinol. 138: 2280-2285 (1997)), the human platelet-derived growth factor (Maher et al., Mol. Cell. Biol. 9: 2251-2253 (1989)), the human extracellular superoxide dismutase (EC-SOD) (Inoue et al., FEBS 269: 89-92 (1990)), the human heparin-binding epidermal growth factor-like growth factor (HB-EGF) (Arkonac et al., J. Biol. Chem. 273: 4400-4405 (1998)), the acid fibroblast growth factor (aFGF) (Fromm et al., Arch. Biochem. Bioph. 343: 92 (1997)), the basic fibroblast growth factor (bFGF) (Yayon et al., Cell 64: 841-848 (1991)), the human intestinal mucin 2 sequence (Xu et al., Glyconjug J. 13: 81-90 (1996)), the human gamma interferon (Lortat-Jacob & Grimaud, FEBS 280: 152-154 (1991)), the subunit p40 of human interleukin 12 (Hasan et al., J. Immunol. 162: 1064-1070 (1999)), the factor l-alpha derived from stromal cells (Amara et al., J. Biol. Chem. 272: 200-204 (1999)), the human neutrophil derived "heparin binding protein" (CAP 37/azurocidin) (Pohl et al., FEBS 272: 200-204 (1990)), an immunoglobulin molecule such as CDR2 and/or CDR3 regions of the anti-DNA monoclonal murine antibody F4.1 (Avrameas et al., Proc. Natl. Acad. Sci. 95: 5601 (1998)), the hyper variable CDR3 region of human anti-DNA monoclonal antibody RTT79 (Stevenson et al., J. Autoimmunity 6: 809 (1993)), the hyper variable area CDR2 and/or CDR3 of the human anti-DNA monoclonal antibody NE-1 (Hirabayashi et al., Scand. J. Immunol. 37: 533 (1993)), the hypervariable area CDR3 of the human anti-DNA monoclonal antibody RT72 (Kalsi et al., Lupus 4: 375 (1995)).

The capacity of the CPPs to react with/bind to glycosaminoglycans (GAGs) can be determined by direct or indirect glycosaminoglycan-binding assays known in the art, such as the affinity coelectrophoresis (ACE) assay for peptide glycosaminoglycan binding described in the PCT patent application WO 00/45831. Several other methods well known in the art are available for analyzing GAG-peptides interactions, for example the method described in the PCT patent application WO 01/64738 or by Weisgraber and Rall (J. Biol. Chem., 262(33):11097-103) (specific example with the apolipoprotein B-100); or by a modified ELISA test: 96-well plates are coated with specific GAG (chondroitin sulfate A, B and C, heparin, heparin sulfate, hyaluronic acid, keratin sulfate, syndecan), peptide conjugated to a marker is then added for a defined time; after extensive washing, peptide binding is determined using specific analysis related to the marker.

CPP can be of any length. For example CPP is less than or equal to 500, 250, 150, 100, 50, 25, 10, 6 or 4 amino acids in length. For example CPP is greater than or equal to 4, 6, 10, 25, 50, 100, 150, 250 or 500 amino acids in length. The suitable length and design of the CPP will be easily determined by those skilled in the art. As general references on CPPs it can be cited: CELL PENETRATING PEPTIDES: PROCESSES AND APPLICATIONS, edited by Ulo Langel (2002); or Advanced Drug Delivery Reviews 57:489-660 (2005).

In preferred embodiments, the CPP is 5, 6, 7, 8, 9, 10, 11, 12, 13, 14, 15, 16, 17, 18, 19, 20, 21, 22, 23, 24 or 25 amino acids in length.

In a preferred embodiment, the CPP comprises the amino acid sequence of formula (I) of less than 50 amino acids in length, preferably less than 25. Generally, the amino acid sequence of formula (I) has more than 8 amino acids, preferably more than 10.

According to particular embodiments, the carrier moiety is a peptide comprising an amino acid sequence of formula (I) wherein C is absent or is in any position of the amino acid sequence, or more preferably is at the C or N terminal position of said amino acid sequence. A moiety comprising a thiol group can be added at any position of the amino acid sequence of formula (I) to conjugate the peptide to camptothecin, derivative or analog thereof, via a thioether bond. More preferably, the moiety comprising a thiol group is either at the C or N terminal position of said amino acid sequence (i.e., the moiety is present at only one of C and N terminal positions, at the other C or N position C of formula (I) is absent). Specifically, the moiety is a cysteine or cysteamine.

Preferably, X1 and X2 independently are amino sequences from 2 to 15 amino acids, more preferably from 2 to 10 amino acids. They can comprise either basic or non basic amino acids. More particularly, X1 and X2 are devoid of cysteine amino acid.

The term "basic amino acid" means any amino acid positively charged at pH 7, particularly any amino acid having guanidyl, amidinyl or amino moieties. The terms "guanidyl" and "guanidine" are used interchangeably to refer to a moiety having the formula —HN=C(NH$_2$)NH (unprotonated form). As an example, arginine contains a guanidyl (guanidino) moiety, and is also referred to as 2-amino-5-guanidinovaleric acid or a-amino-6-guanidinovaleric acid. The terms "amidinyl" and "amidino" are used interchangeably and refer to a moiety having the formula —C(=NH)(NH2). Preferred highly basic amino acids are histidine (H), arginine (R) and/or lysine (K), and more preferably K and R.

The term "non basic amino acid" means any amino acid residue not positively charged at pH 7 or below. It includes consequently, any non polar amino acid (i.e., hydrophobic amino acid), polar uncharged amino acid and negatively charged amino acid at pH 7.

As used herein non polar amino acids are A, I, L, M, F, P, W, and V. Polar uncharged amino acids are N, C, Q, G, S, T and Y. Negatively charged amino acids are D and E.

According to a preferred embodiment, the non basic amino acids comprised in the BX(X)rXB moiety of formula (I) are selected in the group consisting of glutamic acid (E), glycine (G), glutamine (Q), serine (S), threonine (T), leucine (L), valine (V), proline (P), and citrulline.

Preferred amino acid sequences according to the invention are those wherein:
  o is 1, and/or
  p and/or q is 1, and/or
  X1 is a sequence of 3 to 12 amino acids, and/or
  X2 is a sequence of 2 to 10 amino acids, and/or
  r is 0 and/or
  m is 1.

Accordingly, preferred CPPs derived from human heparin binding proteins and capable of specifically penetrating into a cell are selected from the group consisting of:

DPV3 (SEQ ID NO: 1): CPP reacting with heparin and dimer of a peptide derived from the C-terminal part of the sequence of human extracellular superoxide dismutase (EC-SOD) (Inoue et al., FEBS 269: 89-92 (1990)).

DPV6 (SEQ ID NO: 2): CPP reacting with heparin and derived from the amino acid sequence of the C-terminal part of chain A of the human platelet-derived growth factor (Maher et al., Mol. Cell. Biol. 9: 2251-2253 (1989)).

DPV7 (SEQ ID NO: 3) and DPV7b (SEQ ID NO: 4): CPPs reacting with heparin and derived from the C-terminal part of the sequence of the human heparin-binding epidermal growth factor-like growth factor (HB-EGF) (Arkonac et al, J. Biol. Chem. 273: 4400-4405 (1998)).

DPV10 (SEQ ID NO: 5): CPP reacting with heparin and corresponding to the C-terminal part of the human intestinal mucin 2 sequence (Xu et al., Glyconjug J. 13: 81-90 (1996)).

DPV3/10 (SEQ ID NO: 6): CPP reacting with heparin and derived from the C-terminal part of the sequence of human extracellular superoxide dismutase (EC-SOD) (see above) and from C-terminal part of the human intestinal mucin 2 sequence (see above).

DPV10/6 (SEQ ID NO: 7): CPP reacting with heparin and derived from the C-terminal part of the human intestinal mucin 2 sequence (see above) and from the C-terminal part of chain A of the platelet-derived growth factor (see above).

DPV1047 (SEQ ID NO: 8) and DPV1048 (SEQ ID NO: 9): CPP reacting with heparin, 1O derived from the amino acid sequence (3358-3372) of the human lipoprotein B (Cardin et al., Biochem. Biophys. Res. Com. 154: 741 (1988)) and from the sequence of the peptide corresponding to the hypervariable area CDR3 of the human anti-DNA monoclonal antibody NE-1 (Hirabayashi et al., Scand. J. Immunol. 37: 533 (1993)).

DPV15 (SEQ ID NO: 10) and DPV15b (SEQ ID NO: 11): CPPs reacting with heparin and containing part of the sequence of the "heparin binding protein" CAP 37.

According to the invention, the cell penetrating peptide is more specifically selected from one peptide identified in Table 1a below.

TABLE 1a

| SEQ ID NO: | Cell Penetrating Peptides | Amino acid sequences (Nter to Cter) in one letter code |
|---|---|---|
| 1 | DPV3 | RKKRRRESRKKRRRES |
| 2 | DPV6 | GRPRESGKKRKRKRLKP |
| 3 | DPV7 | GKRKKKGKLGKKRDP |
| 4 | DPV7b | GKRKKKGKLGKKRPRSR |
| 6 | DPV3/10 | RKKRRRESRRARRSPRHL |
| 7 | DPV10/6 | SRRARRSPRESGKKRKRKR |
| 8 | DPV1047 | VKRGLKLRHVRPRVTRMDV |
| 9 | DPV1048 | VKRGLKLRHVRPRVTRDV |
| 5 | DPV10 | SRRARRSPRHLGSG |
| 10 | DPV15 | LRRERQSRLRRERQSR |
| 11 | DPV15b | GAYDLRRRERQSRLRRRERQSR |
| 12 | Buforin II | TRSSRAGLQFPVGRVHRLLRK |
| 13 | GALA | WEAALAEALAEALAEHLAEALAEALEALAA |
| | Haptotactic peptides: | |
| 14 | Cβ | KGSWYSMRKMSMKIRPFFPQQ |
| 15 | preCγ | KTRYYSMKKTTMKIIPFNRL |
| 16 | CαE | RGADYSLRAVRMKIRPLVTQ |
| 17 | hCT(9-32) | LGTYTQDFNKFHTFPQTAIGVGAP |
| 18 | HN-1 | TSPLNIHNGQKL |
| 19 | Influenza virus nucleoprotein (NLS) | NSAAFEDLRVLS |
| 20 | KALA | WEAKLAKALAKALAKHLAKALAKALKACEA |
| 21 | K-FGF | AAVALLPAVLLALLAP |
| 22 | Ku70 | VPMLKPMLKE |
| 23 | MAP | KLALKLALKALKAALKLA |
| 24 | MPG | GALFLGFLGAAGSTMGAWSQPKKKRKV |
| 25 | MPM (IP/K-FGF) | AAVALLPAVLLALLAP |

TABLE 1a-continued

| SEQ ID NO: | Cell Penetrating Peptides | Amino acid sequences (Nter to Cter) in one letter code |
|---|---|---|
| 26 | N50 (NLS of NF-κB P50) | VQRKRQKLM |
| 27 | Pep-1 | KETWWETWWTEWSQPKKKRKV |
| 28 | Pep-7 | SDLWEMMMVSLACQY |
| 29 | Penetratin | RQIKIWFQNRRMKWKK |
| 30 | Short Penetratin | RRMKWKK |
| 31 | Poly Arginine - $R_7$ | RRRRRRR |
| 32 | Poly Arginine - $R_9$ | RRRRRRRRR |
| 33 | pISL | RVIRVWFQNKRCKDKK |
| 34 | Prion mouse $PrPc_{1-28}$ | MANLGYWLLALFVTMWTDVGLCKKRPKP |
| 35 | pVEC | LLIILRRRIRKQAHAHSK |
| 36 | SAP | VRLPPPVRLPPPVRLPPP |
| 37 | SV-40 (NLS) | PKKKRKV |
| 38 | SynB1 | RGGRLSYSRRRFSTSTGR |
| 39 | SynB3 | RRLSYSRRRF |
| 40 | SynB4 | AWSFRVSYRGISYRRSR |
| 41 | $Tat_{47-60}$ | YGRKKRRQRRRPPQ |
| 42 | $Tat_{47-57}$ | YGRKKRRQRRR |
| 43 | $Tat_{49-57}$ | RKKRRQRRR |
| 44 | $Tat_{48-60}$ | GRKKRRQRRRPPQ |
| 45 | Transportan | GWTLNSAGYLLGKINLKALAALAKKIL |
| 46 | Transportan 10 | AGYLLGKINLKALAALAKKIL |
| 47 | Transportan derivatives: | GWTLNSAGYLLG |
| 48 | | INLKALAALAKKIL |
| 49 | VP22 | DAATATRGRSAASRPTERPRAPARSASRPRRPVD |
| 50 | VT5 | DPKGDPKGVTVTVTVTVTGKGDPKPD |
| 51 | DPV51 | KRGLKLRH |

As mentioned before, each of the peptides identified in Table 1a advantageously presents a cysteine at the C or N position of the amino acid sequence.

The cell penetrating peptides according to the invention can be, but not limited to, those described above or analogs thereof. An "analog" that is at least about 50%, preferably at least about 70%, more preferably at least about 80%-85%, preferably at least about 90% and most preferably at least about 95%-99% identical thereto. For example, peptides can have substitutions at 1, 2, 3, 4 or more residues. The CPP can be used in their monomeric form (such as described above) or polymeric form (dimer, trimer, etc.).

If necessary, several well known chemical strategies can be used by one skilled in the art for transforming a CPP into a drug candidate with increased stability in vivo and/or biological activity; such as:

N- and C-terminus modifications to prevent exopeptidase degradation: C-terminal amidation, or N-terminal acetylation, cyclization by forming a disulfide bridge, alkylation of amide nitrogen to prevent endopeptidase degradation, introduction of non-natural amino acids to modify the recognition site of the endopeptidase (2-methylalanine, alpha-dialkylated glycine, oligocarbamate, oligourea, guanidino or amidino backbones . . . ), incorporation of non-genetically encoded amino acids (methylation, halogenation or chlorination of glycine or phenylalanine) into the CPP amino acid sequence, replacement of some or even all the L-amino acids with their corresponding D-amino acids or beta-amino acid analogues. Such peptides may be synthesized as "inverso" or "retro-inverso" forms, that is, by replacing L-amino acids of the sequence with D-amino acids, or by reversing the sequence of the amino acids and replacing the L-amino acids with D-amino acids. Structurally, the retro-inverse peptide is much more similar to the original peptide than the simple D-analogue. D-peptides are substantially more resistant to peptidases, and therefore are more stable in serum and tissues compared to their L-peptide counterparts. In a preferred embodiment CPPs containing L-amino acids are capped with a single D-amino acid to inhibit exopeptidase destruction, synthesis of CPP-derived oligocarbamate; the oligocarbamate backbone consists of a chiral ethylene backbone linked through relatively rigid carbamate bonds (Cho et al., Science 261:1303-1305 (1993)).

The conjugate according to the invention further comprises a camptothecin, analog or derivative thereof.

As used herein, "camptothecin, analog or derivative thereof" refers to any biologically active compound having the property to bind in vitro and/or in particular in vivo to the enzyme DNA topoisomerase I and containing the camptothecin backbone as represented by the following formula (II):

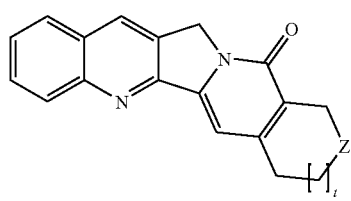

wherein t is 0, 1 or 2 and Z is a —COO— group (orientation of —COO— group is from bottom to top following the way formula (II) is written) or a substituted or unsubstituted divalent alkyl group.

More particularly, camptothecin, analog or derivative thereof contains the camptothecin backbone of formula (II) wherein any of the hydrocarbon groups represented therein may be substituted, preferably one, two, three or four hydrocarbon groups are substituted.

The substituents of formula (II) may vary over a large range to the extent that camptothecin, analog or derivative thereof presents the property to bind in vitro and/or in particular in vivo to the enzyme DNA topoisomerase I.

Substituents are independently the same or different and are preferably alkyl group, aryl group, halogen, —OR', =O, =NR', =N—OR', —NR'R", —SR', —SiR'R"R''', —OC(O) R', —C(O)R', —CO$_2$R', —CONR'R", —OC(O)NR'R", —NR"C(O)R', —NR'—C(O)NR"R''', —NR"C(O)$_2$R', —NR—C(NR'R")=NR''', —S(O)R', —S(O)$_2$R', —S(O)$_2$ NR'R", —NRSO$_2$R', —CN and —NO$_2$, —R', —N$_3$, —CH (Ph)$_2$, fluoro(C$_1$-C$_4$)alkoxy, fluoro(C$_1$-C$_4$)alkyl or two adjacent groups may form together with the carbon atoms carrying them a group of the formula —O(CH2)$_u$O—, wherein u represents the integer 1 or 2; and where R', R", R''' and R'''' are preferably independently selected from hydrogen, (C$_1$-C$_8$) alkyl, (C$_1$-C$_8$)heteroalkyl, aryl and heteroaryl, (unsubstituted aryl)-(C$_1$-C$_4$)alkyl, and (unsubstituted aryl)oxy-(C$_1$-C$_4$) alkyl. When a camptothecin analog of the present invention includes more than one R group, for example, each of the R groups is independently selected as are each R', R", R''' and R'''' groups when more than one of these groups is present. Said substituents can also be substituted. For instance, any group may be substituted by at least one alkyl group, aryl group, halogen, —OR', =O, =NR, =N—OR', —NR'R", —SR', —SiR'R"R''', —OC(O)R', —C(O)R', —CO$_2$R', —CONR'R", —OC(O)NR'R", —NR"C(O)R', —NR'—C(O) NR"R''', —NR"C(O)$_2$R', —NR—C(NR'R")=NR''', —S(O) R', —S(O)$_2$R', —S(O)$_2$ NR'R", —NRSO$_2$R', —CN and —NO$_2$, —R', —N$_3$, —CH (Ph)$_2$, fluoro(C$_1$-C$_4$)alkoxy, fluoro(C$_1$-C$_4$)alkyl.

In particular, substituents are selected from the group consisting of an alkyl group, preferably lower alkyl group; —OR', wherein R' is H; —OC(O)R', wherein R' is an alkyl group including heteroalkyl groups and more preferably heterocycloalkyl groups, such as piperidine or piperazine group; an alkyl group substituted by —NR'R" or heteroalkyl groups and more preferably heterocycloalkyl groups, such as piperidine or piperazine group; two adjacent groups may form together with the carbon atoms carrying them a group of the formula —O(CH2)$_u$O—, wherein u represents the integer 1 or 2, preferably 2.

The term "alkyl" by itself or as part of another substituent, means, unless otherwise stated, a straight or branched chain, or cyclic hydrocarbon radical, optionally interrupted by at least one heteroatom including O, N, Si and S (as defined below), or combination thereof, which may be fully saturated, mono-or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl) methyl, cyclopropylmethyl, homologs and isomers of, for example, n-pentyl, n-hexyl, n-heptyl, n-octyl, and the like. An unsaturated alkyl group is one having one or more double bonds (e.g., alkenyl groups) or triple bonds (e.g., alkynyl groups). Examples of unsaturated alkyl groups include, but are not limited to, vinyl, 2-propenyl, crotyl, 2-isopentenyl, 2-(butadienyl), 2,4-pentadienyl, 3 (1,4-pentadienyl), ethynyl, 1- and 3-propynyl, 3-butynyl, and the higher homologs and isomers. The term "alkyl" unless otherwise noted, is also meant to include those derivatives of alkyl defined in more detail below, such as "heteroalkyl". Alkyl groups, which are limited to hydrocarbon groups are termed "homoalkyl".

The term "alkyl" by itself or as part of another substituent includes mono- or divalent radical derived from an alkane. Among the divalent radical, one can cite, but not limited, —CH$_2$—, —CH$_2$CH$_2$—, —CH$_2$CH$_2$CH$_2$—, —CH$_2$CH$_2$CH$_2$CH$_2$—.

Typically, an alkyl group will have from 1 to 24 carbon atoms, with those groups having 10 or fewer carbon atoms being preferred in the present invention. A "lower alkyl" is a shorter chain alkyl group, generally having eight or fewer carbon atoms.

The term "heteroalkyl" by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen, carbon and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —S(O)—CH$_3$, —CH$_2$—CH$_2$—S (O)$_2$—CH$_3$, —CH=CH—O—CH$_3$, —Si (CH$_3$)$_3$, —CH$_2$—CH=N—OCH$_3$ and CH=CH—N(CH$_3$)—CH$_3$. A silicon group refers to a Si placed at any interior position of the heteroalkyl group or at the position at which the alkyl group is attached to the remainder of the molecule. Up to two heteroatoms may be consecutive, such as, for example, —CH$_2$—NH—OCH$_3$ and —CH$_2$—O—S—(CH$_3$)$_3$.

Similarly, the term "heteroalkyl" by itself or as part of another substituent includes divalent radicals derived from heteroalkyl, as exemplified, but not limited by, —CH$_2$—CH$_2$—S—CH$_2$—CH$_2$—and —CH$_2$—S—CH$_2$—CH$_2$—NH—CH$_2$—. The terms "heteroalkyl" may encompass poly (ethylene glycol) and its derivatives. Still further, for divalent alkyl and heteroalkyl groups, no orientation of the linking group is implied by the direction in which the formula of the group is written. For example, the formula —C(O)$_2$R'— represents both —C(O)$_2$R'— and —R'C(O)$_2$—.

The term "lower" in combination with the terms "heteroalkyl" refers to a moiety having from 1 to 8 carbon atoms.

The terms "alkoxy", "alkylamino" and "alkylthio" (or thioalkoxy) are used in their conventional sense, and refer to those alkyl groups attached to the remainder of the molecule via an oxygen atom, an amino group, or a sulfur atom, respectively.

In general, an "acyl substituent" is also selected from the group set forth above. As used herein, the term "acyl substituent" refers to groups attached to, and fulfilling the valence of a carbonyl carbon that is either directly or indirectly attached to the compounds of the present invention.

The terms "cycloalkyl" and "heterocycloalkyl", by themselves or in combination with other terms, represent, unless otherwise stated, cyclic versions of substituted or unsubstituted "alkyl" (more preferably C$_1$-C$_{10}$ cycloalkyl) and substituted or unsubstituted "heteroalkyl" (more preferably C$_1$-C$_{10}$ heterocycloalkyl), respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The heteroatoms and carbon atoms of the cyclic structures are optionally oxidized.

The terms "halo" or "halogen" by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$) alkyl" is mean to include, but not be limited to, trifluoromethyl, 2,2,2-trifluoroethyl, 4-chlorobutyl, 3-bromopropyl, and the like.

The term "aryl" means, unless otherwise stated, a substituted or unsubstituted polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen, carbon and sulfur atoms are optionally oxidized, and the nitrogen atom (s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2pyrrolyl, 3-pyrrolyl, 3-pyrazolyl, 2-imidazolyl, 4-imidazolyl, pyrazinyl, 2-oxazolyl, 4oxazolyl, 2-phenyl-4-oxazolyl, 5-oxazolyl, 3-isoxazolyl, 4-isoxazolyl, 5-isoxazolyl, 2thiazolyl, 4-thiazolyl, 5-thiazolyl, 2-furyl, 3-furyl, 2-thienyl, 3-thienyl, 2-pyridyl, 3-pyridyl, 4-pyridyl pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

Substituents for each of the above noted aryl and heteroaryl ring systems are selected from the group of acceptable substituents described below. "Aryl" and "heteroaryl" also encompass ring systems in which one or more non-aromatic ring systems are fused, or otherwise bound, to an aryl or heteroaryl system.

For brevity, the term "aryl" when used in combination with other terms (e.g., aryloxy, arylthioxy, arylalkyl) includes both aryl and heteroaryl rings as defined above.

Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Among camptothecin, analogs and derivatives thereof, one can cite more preferably the compounds described in the following patents/patent applications: WO 99/09996, WO 99/65493, WO 00/53607, EP 1 101 765, EP 137,145, EP 074,256, U.S. Pat. No. 4,604,463, EP 56,692, EP 88,642, EP 296,612, EP 321,122, EP 325,247, EP 540,099, EP 737,686, WO 90/03169, WO 96/37496, WO 96/38146, WO 96/38449, WO 97/00876, U.S. Pat. No. 7,104,894, the disclosure of each of these is incorporated herein by reference.

In a preferred embodiment, camptothecin backbone is of formula (II) wherein t is 0 and Z is a COO group as defined above, which can be represented by the following formula (III):

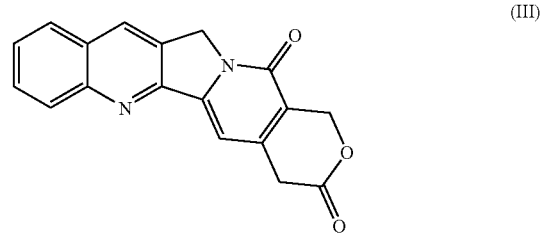 [SMILES: O=C1Cc2cc3n(c(=O)c2CO1)Cc1cc2ccccc2nc1-3]

According to a more preferred embodiment, camptothecin backbone is represented by the following formula (IV):

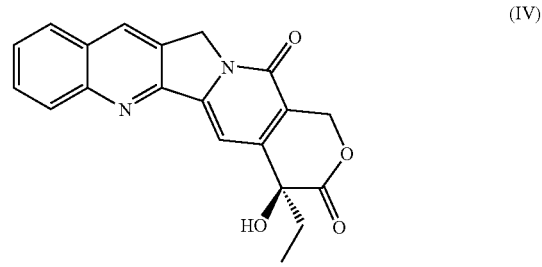 [SMILES: CC[C@@]1(O)C(=O)OCc2c1cc1n(c2=O)Cc2cc3ccccc3nc2-1]

More particularly, camptothecin, analog or derivative thereof contains the camptothecin backbone of formula (III) and more preferably formula (IV) wherein any of the hydrocarbon groups represented therein may be substituted as defined above.

In particular, camptothecin, analogs and derivatives thereof are selected from irinotecan, topotecan, GI-147211C, SN38, 7-hydroxymethyl camptothecin, 9-aminocamptothecin (9-AC), 7-aminomethyl camptothecin, 10-hydroxycamptothecin and (20S)-camptothecin (called camptothecin). The structures of said compounds are the following:

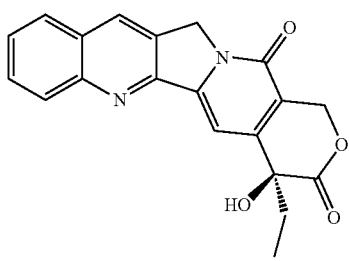
(20S)-camptothecin

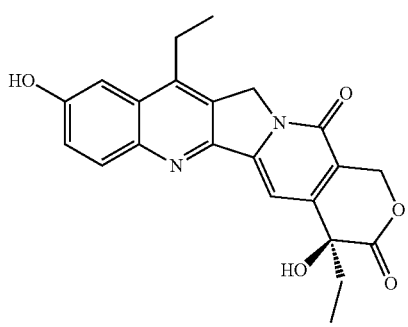
SN-38

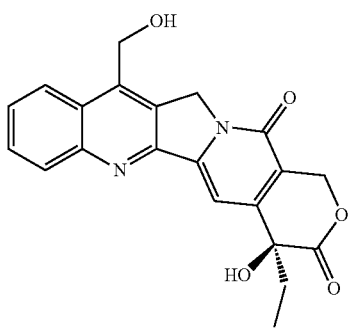
7-hydroxymethyl camptothecin

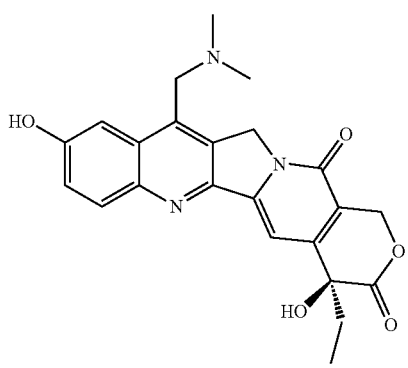
Topotecan

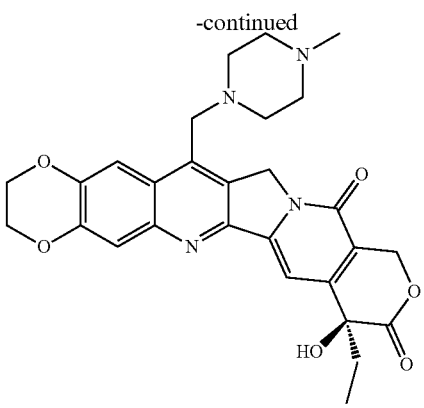
GI-147211C

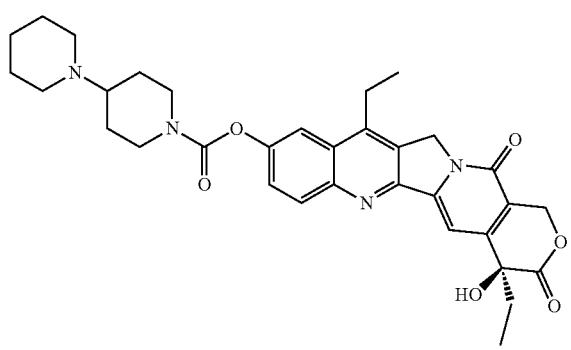
Irinotecan

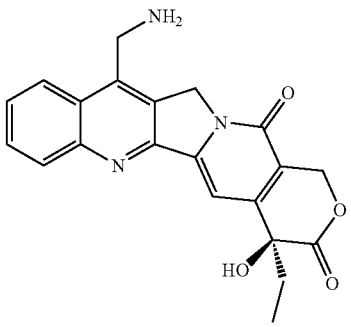
7-aminomethyl camptothecin

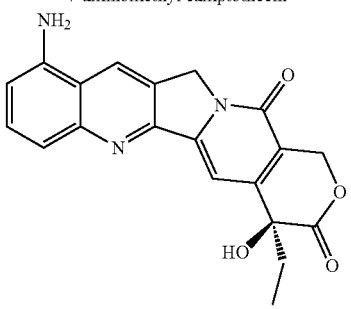
9-aminocamptothecin

The drug moiety may be directly or indirectly linked to the carrier moiety. In the preferred embodiment wherein the drug moiety is indirectly linked to the carrier, the linkage may be an intermediary bonding group such as described below, all such linking groups and others described below, are hereinafter referred to as linker moieties, or are derived from the crosslinking reagents defined below.

In accordance with the present invention, each carrier moiety is linked to at least one drug moiety and more preferably to one drug moiety.

In a particular embodiment, the carrier moiety is prepared such as to facilitate linkage to more than one drug moiety, each drug moiety being the same or different. For example, the carrier moiety may comprise components that themselves facilitate the attachment of more than one drug moiety such as derivatives of naturally occurring amino acids, such as cysteine, or insertion of a multi-valent synthetic amino acid or a linker with multiple active sites. In this manner, a single carrier moiety may carry between 2 and 10 or more preferably between 4 and 5 drug moieties. In this further embodiment each drug moiety may be directly or indirectly linked to the carrier moiety by the same or different linker moiety. When more than one different type of drug moiety is attached, it is possible to co-ordinate the ratios and dosages of the individual drugs to facilitate the administration of specific drug combinations.

Direct linkage may occur through any convenient functional group on the drug moiety such as a hydroxy, carboxy or amino group.

Indirect linkage which is preferable, will occur through a linking moiety. Linking moieties may also provide intramolecular flexibility or adjust intramolecular distances between conjugated domains and thereby may help preserve biological activity. Suitable linking moieties include bi and multifunctional organic radicals independently selected from substituted or unsubstituted alkyl, substituted or unsubstituted heteroalkyl, substituted or unsubstituted aryl, substituted or unsubstituted heteroaryl, aldehydes, acids, esters, anhydrides, sulphydryl or carboxyl groups, such as maleimido derivatives as defined below, maleimido cyclohexane derivatives, maleimido benzoic acid derivatives, maleimidocaproic acid derivatives and succinimido derivatives or may be derived from cyanogen bromide or chloride, succinimidyl esters or sulphonic halides and the like or combinations thereof.

Each of the above terms (e.g., "alkyl", "heteroalkyl", "aryl" and "heteroaryl") include both substituted and unsubstituted forms of the indicated radical. Preferred substituents for each type of radical are provided below.

Substituents for the alkyl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generally referred to as "alkyl substituents" and "heteroalkyl substituents", respectively, and they can be one or more of a variety of groups selected from, but not limited to —OR', =O, =NR', 'N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR"", —NR—C(NR'R")'NR'", —S(O)R', —S(O)$_2$R', —S(O)$_2$NR'R", —NRSO$_2$R', NRR'SO$_2$R", —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the present invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, C(O)CH$_2$OCH$_3$, and the like).

Similar to the substituents described for the alkyl radical, the aryl substituents and heteroaryl substituents are generally referred to as "aryl substituents" and "heteroaryl substituents", respectively and are varied and selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, (C$_1$-C$_8$) alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a linking moiety of the present invention includes more than one R group, for example, each of the R groups is independently selected as are each R', R", R'" and R"" groups when more than one of these groups is present.

Two of the aryl substituents on adjacent atoms of the aryl or heteroaryl ring may optionally be replaced with a substituent of the formula -T-C(O)—(CRR')$_v$—U—, wherein T and U are independently NR—, —O—, —CRR'— or a single bond, and v is an integer of from 0 to 3. Alternatively, two of the substituents on adjacent atoms of the aryl or heteroaryl ring may optionally be replaced with a substituent of the formula -A-(CH2)x-B—, wherein A and B are independently —CRR'—, —O—, —NR—, —S—, —S(O)—, —S(O)$_2$—, —S(O)$_2$NR'— or a single bond, and x is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula-(CRR')b-X—(CR'R'")d-, where b and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$) alkyl.

As used herein, the term "heteroatom" includes oxygen (O), nitrogen (N), sulfur (S) and silicon (Si).

As used before, the symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

The functional groups (i.e. reactive groups) on the linker moiety used to form covalent bonds between linker and drugs on the one hand, as well as linker and carrier moiety on the other hand, may be the same (i.e., homofunctional groups) or preferably different types of functional groups (i.e., heterofunctional groups), including more particularly amino, hydrazino, hydroxyl, thiol, maleimido, carbonyl, and carboxyl groups. According to a preferred embodiment, the functional groups are selected from carboxyl (—COOH) and maleimido groups. The linker moiety may include a short sequence of from 1 to 4 amino acid residues that optionally includes a thiol group through which the linker moiety bonds to the carrier moiety.

In specific embodiments, coupling of the carrier moiety and the drug moiety can be accomplished via a cross-linking reagent. There are several intermolecular cross-linking reagents which can be utilized, see for example, Means and Feeney, CHEMICAL MODIFICATION OF PROTEINS, Holden-Day, 1974, pp. 39-43. Among these reagents are, for example, N-succinimidyl 3-(2-pyridyldithio) propionate (SPDP) or N,N'-(1,3-phenylene) bismaleimide (both of which are highly specific for sulfhydryl groups and form irreversible linkages); N,N'-ethylene-bis-(iodoacetamide) or other such reagent having 6 to 11 carbon methylene bridges (which are relatively specific for sulfhydryl groups); and 1, 5-difluoro-2,4-dinitrobenzene (which forms irreversible linkages with amino and tyrosine groups). Other cross-linking reagents useful for this purpose include: p,p'-difluoro-N,N'-dinitrodiphenylsulfone (which forms irreversible cross-linkages with amino and phenolic groups); dimethyl adipimidate (which is specific for amino groups); phenol-1,4-disulfonyl-chloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine); N-3-Maleimidopropanoic acid; N-6-Maleimidocaproic acid; N-11-Maleimidoundecanoic acid, 4-(N-maleimidomethyl)cyclohexane-1-carboxy-6-amidocaproic acid; 4-[(N-maleimidoethyl)carboxamidoethyl(Peg)$_4$ carboxamidomethyl]cyclohexanecarboxylic acid.

As mentioned before, cross-linking reagents may be homobifunctional, ie., having two functional groups that undergo the same reaction. An example of a homobifunctional cross-linking reagent is bismaleimidohexane ("BMH"). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible cross-linking of polypeptides that contain cysteine residues. Cross-linking reagents may also be heterobifunctional. Heterobifunctional cross-linking reagents have two different functional groups, for example an amine-reactive group and a thiol-reactive group, that will cross-link two moieties having free amines and thiols, respectively. Preferred heterobifunctional cross-linking reagents are succinimidyl 4-(N-maleimidomethyl)cyclohexane-1 -carboxylate ("SMCC"), Succinimidyl-4-(N-maleimidomethyl)-cyclohexane-1-carboxy(6-amidocaproate) ("LC-SMCC"), N-maleimidobenzoyl-N-hydroxysuccinimide ester ("MBS"), and succinimide 4-(p-maleimidophenyl)butyrate ("SMPB"), an extended chain analog of MBS. The succinimidyl group of these cross-linking reagents reacts with a primary amine forming an amide bond, and the thiol-reactive maleimide forms a covalent thioether bond with the thiol group (e.g., of a cystein).

Cross-linking reagents often have low solubility in water. A hydrophilic moiety, such as a sulfonate group, may be added to the cross-linking reagent to improve its water solubility. Sulfo-MBS and sulfo-SMCC are examples of cross-linking reagents modified for water solubility.

Many cross-linking reagents yield a conjugate that is essentially non-cleavable under cellular conditions. However, some cross-linking reagents contain a covalent bond, such as a disulfide, that is cleavable under cellular conditions. For example, Traut's reagent, dithiobis(succinimidylpropionate) ("DSP"), and N-succinimidyl 3-(2-pyridyldithio)propionate ("SPDP") are well-known cleavable cross-linking reagents. Direct disulfide linkage may also be useful.

Numerous cross-linking reagents, including the ones discussed above, are commercially available. Detailed instructions for their use are readily available from the commercial suppliers. A general reference on protein cross-linking and conjugate preparation is: Wong, CHEMISTRY OF PROTEIN CONJUGATION AND CROSS-LINKING, CRC Press (1991).

The linkers that can be used according to the present invention may differ between each other by their stability in biological fluids (e.g. human plasma) when conjugated. The term "stability" is defined as the half-life time of release of the camptothecin derivative from the conjugate of the invention, which is dependent on the chosen linker. Advantageously, the conjugate of the present invention is stable, in particular it presents a half-life time of 1, 2, 3, 4, 5, 6, 7, 8, 9, or 10 hours. An unstable conjugate will release the drug moiety with shorter half-life time, e.g. <5 minutes. A highly stable conjugate has a plasma half-life time above 11 hours. Preferably, the conjugate is stable in human plasma in vitro with a half-life time of about 1 to 6.5 hours at 37° C. The half life time of the conjugate is determined as described in Example II.

Preferred heterobifunctional cross-linking reagents of the present invention comprise a free —COOH group and a free maleimide group. Among such cross-linking reagents, one can cite the following compound:

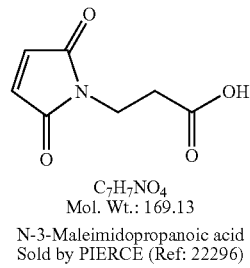 [SMILES: O=C(O)CCN1C(=O)C=CC1=O]

$C_7H_7NO_4$
Mol. Wt.: 169.13

N-3-Maleimidopropanoic acid
Sold by PIERCE (Ref: 22296)

And more particularly, the conjugate of the invention derives from the following crosslinking reagents:

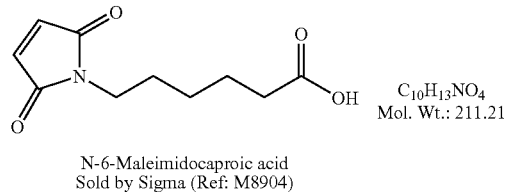

$C_{10}H_{13}NO_4$
Mol. Wt.: 211.21

N-6-Maleimidocaproic acid
Sold by Sigma (Ref: M8904)

-continued

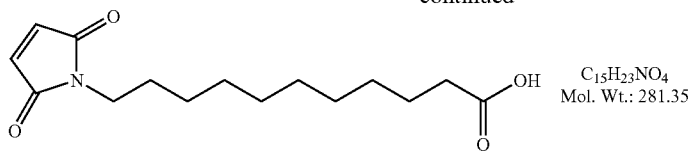

N-11-Maleimidoundecanoic acid
sold by PIERCE (Ref: 22211)

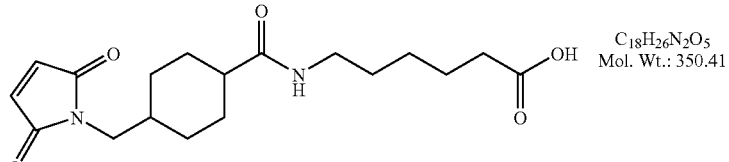

4-(N-maleimidomethyl)cyclohexane-1-carboxy-6-amidocaproic acid

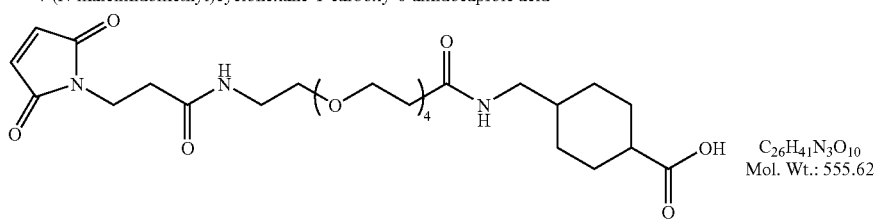

4-[(N-maleimidoethyl)carboxamidoethyl(Peg)$_4$
carboxamidomethyl]cyclohexanecarboxylic acid

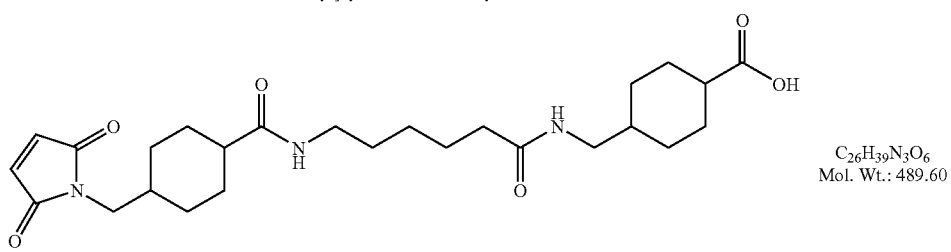

4-[(N-maleimidomethyl)cyclohexane-1-carboxy-6-amidohexanecarboxamido
methyl]cyclohexanecarboxylic acid

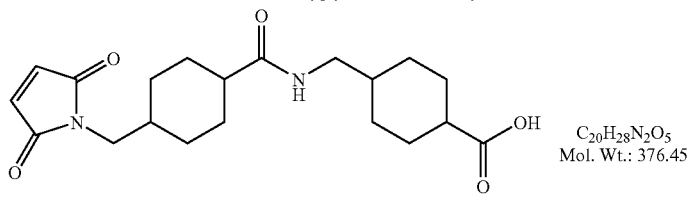

4-[((N-maleimidomethyl)cyclohexanecarboxamido)methyl]
cyclohexanecarboxylic acid In this context, another object of the present invention deals with novel compounds, particularly suitable as cross-linking reagents, represented by the following formula (V):

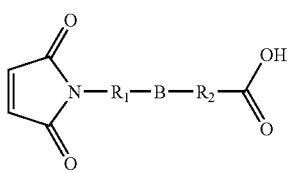

(V)

wherein B is a substituted or unsubstituted cycloalkyl group, and R1 and R2 independently are nothing (i.e. a covalent bond) or a substituted or unsubstituted divalent alkyl, heteroalkyl, aryl or heteroaryl group;

salts and/or isomers thereof.

Such cross-linking reagents are very useful since the conjugates obtained therefrom are advantageously stable in human plasma in vitro with a half life time of more than 5 minutes at 37° C.

The cited groups of formula (V) are as defined above.

In a particular embodiment, the compounds are represented by formula (V) wherein R1 is a substituted or unsubstituted divalent alkyl, heteroalkyl, aryl or heteroaryl group and R2 is nothing or a substituted or unsubstituted divalent alkyl, heteroalkyl, aryl or heteroaryl group.

In another particular embodiment, the compounds are represented by formula (V) wherein at least one R1 and R2 is interrupted by at least one divalent radical selected from —O—, —NR'—, —SR'—, —SiR'R"—, —OC(O)—, —C(O)—, —CO₂—, —CONR'—, —NR'CO—, —OC(O)NR'—, —NR"OC(O)—, and —NR"C(O)₂—, wherein R' and R" independently are as defined above, in particular R' and R" are selected from hydrogen, $(C_1-C_8)$alkyl, $(C_1-C_8)$heteroalkyl, aryl and heteroaryl group as defined above.

When R1 and/or R2 are interrupted by at least one divalent radical, said interruption may be placed at any interior position of the R1 and/or R2 group or at the position at which R1 and/or R2 group is attached to the remainder of compound of formula (V).

In particular embodiments, the present invention relates to compounds of formula (V) wherein:
- B is a cyclo(C3-C8)alkyl, preferably unsubstituted cycloalkyl, including cyclopentyl or cyclohexyl radical, and/or
- R1 is an heteroalkyl group, in particular encompassing poly(ethylene glycol) (i.e., PEG) and its derivatives, such PEG-3, -4, -5, or -6, and/or
- R1 is a straight (C1-C8) alkyl chain, in particular —CH₂—, or —CH₂CH₂—, and/or
- R1 is a (C1-C8) alkyl chain, optionally interrupted by at least one, preferably one or two, divalent radical selected from —OC(O)—, —CO₂—, —CONR'—, —NR'CO—, —OC(O)NR'—, and —NR"C(O)₂—, preferably —CONR'— or —NR"OC(O)—, wherein R' and R" independently from each other are preferably selected from hydrogen and $(C_1-C_8)$alkyl, and optionally said (C1-C8) alkyl chain comprises at least one cycloalkyl chain as defined above, and/or
- R2 is nothing, and/or
- R2 is an heteroalkyl group, in particular encompassing poly(ethylene glycol) (i.e., PEG) and its derivatives, such PEG-3, -4, -5, or -6, and/or
- R2 is a straight (C1-C8) alkyl chain, in particular —CH₂—, or —CH₂CH₂—, and/or
- R2 is a (C1-C8) alkyl chain, optionally interrupted by at least one, preferably one or two, divalent radical selected from —OC(O)—, —CO₂—, —CONR'—, —NR'CO—, —OC(O)NR'—, and —NR"C(O)₂—, preferably —CONR'— or —NR"OC(O)—, wherein R' and R" independently from each other are preferably selected from hydrogen and $(C_1-C_8)$alkyl, and optionally said (C1-C8) alkyl chain comprises at least one cycloalkyl chain as defined above.

In particular, compounds of formula (V) can be illustrated by the compounds identified above, i.e.:
4-(N-maleimidomethyl)cyclohexane-1-carboxy-6-amidocaproic acid,
4-[(N-maleimidoethyl)carboxamidoethyl(Peg)4carboxamidomethyl]cyclohexanecarboxylic acid,
4-[(N-maleimidomethyl)cyclohexane-1-carboxy-6-amidohexanecarboxamidomethyl]cyclohexanecarboxylic acid, or
4-[((N-maleimidomethyl)cyclohexanecarboxanido)methyl]cyclohexanecarboxylic acid.

The compound of formula (V) can be prepared by different methods well known in the art. In particular, compound of formula (V) is prepared by the methods described in the examples. According to a particular aspect of the invention, the conjugate comprises a drug moiety linked to a carrier moiety as defined above, wherein the drug moiety is linked covalently to the carrier moiety with a linker resulting from a compound (cross-linking reagent) of formula (V) as defined above.

According to this particular embodiment, the conjugate of the present invention presents more particularly the following formula (VI):

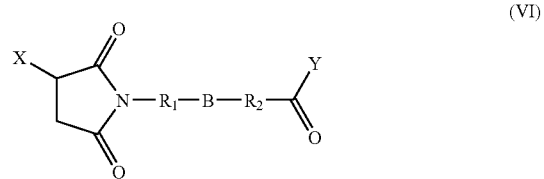

(VI)

wherein X is the carrier moiety (CPP) as defined above, in particular represented by formula (I), which is attached to the remainder of the compound by a thioether bond, and
B, R1, R2 are groups as defined above,
and Y is the drug moiety as defined above, in particular SN38 moiety, In a further particular embodiment, the conjugate is represented by formula (VI) wherein Y is attached to the remainder of the conjugate through a thioether, hydrazone, amide, ester, ether, carbamate, or thiocarbamate bond, more particularly through an ether bond (—O—), disulfide or thioether bond.

The conjugates described herein, including those of formula (VI), are novel chemical entities. In a particular aspect of the invention, the conjugate of the invention include those wherein the carrier moiety is represented by formula (I) (including any preferred embodiment identified above) and optionally wherein the linker group is derived from a cross-linking reagent comprising a free —COOH group and a free maleimide group, in particular from N-6-Maleimidocaproic acid and 4-[((N-maleimidomethyl)cyclohexanecarboxamido)methyl]cyclohexanecarboxylic acid.

Specific chemical entities disclosed herein include, but are not limited to:

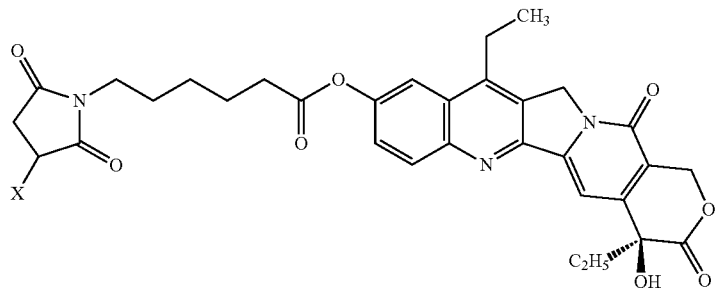

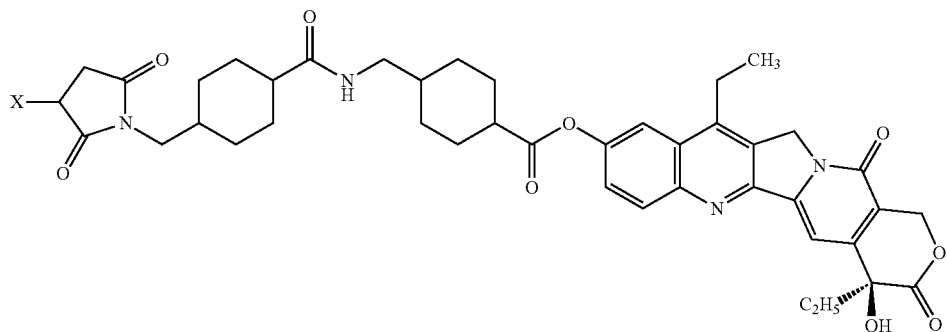
wherein X is as defined above, in particular DPV3, DPV3.10, DPV6, DPV7, DPV7b, DPV15, DPV15b, DPV1047, DPV1048, DPV10, or DPV10/6, and even more preferably DPV3, DPV15, DPV15b, or DPV1047.
Embodiments of the invention include the following:
(SEQ ID NO:53)
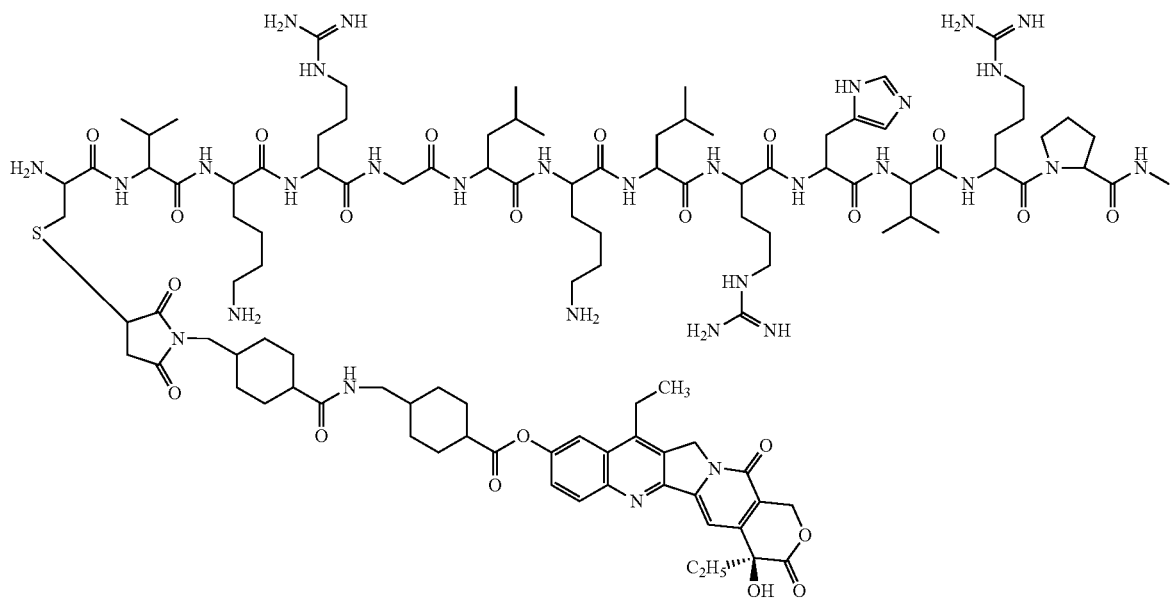
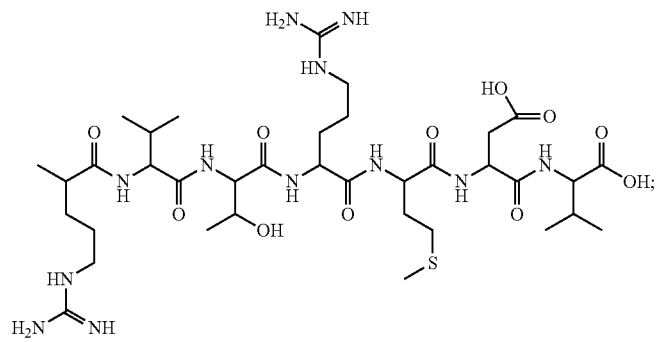

-continued
(SEQ ID NO:53)
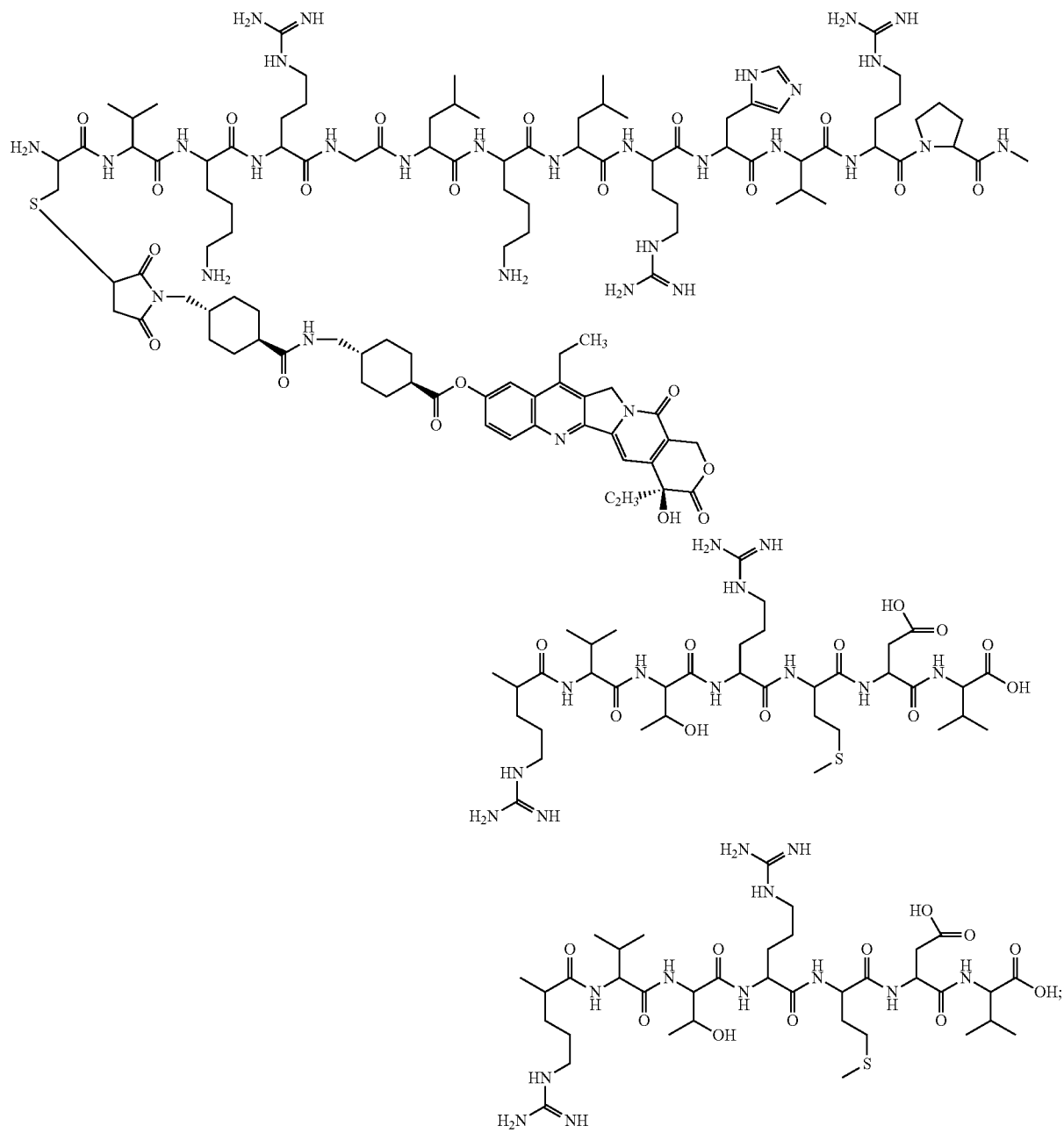
(SEQ ID NO:54)
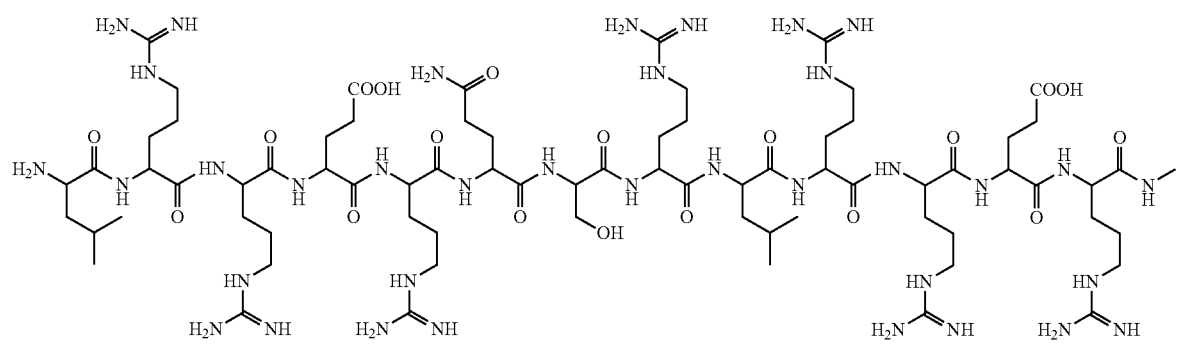

-continued

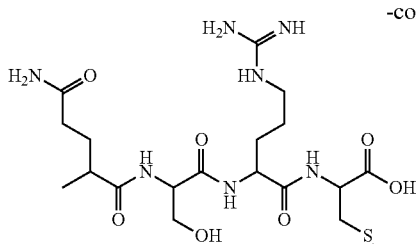
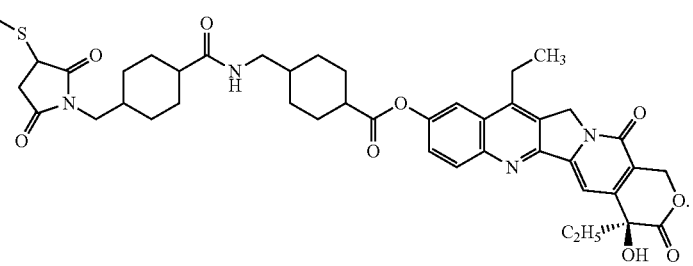

The present invention also relates to methods for preparing the same.

The conjugate of the invention may be prepared by any method known in the art.

For example, the carrier moiety (or peptide) can be prepared using conventional solution- or solid-phase peptide synthesis methods. This peptide can then be reacted directly with the drug moiety, a suitable reactive derivative of a drug moiety, or a cross-linking reagent.

A drug moiety or a derivative thereof may be attached to the carrier moiety through e.g. thioether, hydrazone, amide, ester, ether, carbamate, thiocarbamate or disulphide bond formation.

Alternatively, a linker group, as described above, and in particular is used to prepare a conjugate of formula (VI), is introduced by reaction of a cross-linking reagent, and in particular a cross-linking reagent of formula (V), with an appropriate function of the carrier moiety, in particular a thiol group, followed by formation of a covalent bond between the linker group and the drug moiety. In the particular embodiment of conjugate of formula (VI), the drug presents an appropriate function to form a covalent bond with the linker. Said appropriate function is more preferably an hydroxyl group so as to form an ester bond between the linker group and the drug moiety. Multivalent drug-delivery conjugates may be obtained, inter alia, by successive extension of an appropriate function of the carrier moiety with, for instance, bivalent or trivalent chemical groups.

According to another preferred embodiment, the cross-linking reagent is coupled to the drug moiety prior to reaction with the carrier moiety.

Using these methods, the skilled person will be capable of preparing a wide variety of drug-carrier conjugates utilising a variety of linker moieties. As exemplified below, an appropriate group on the drug moiety may be selected for attachment to the carrier moiety and if desired a linker joined to the drug or carrier moiety, or both prior to their coupling. Alternatively, drug may also be modified so as to allow conjugation.

The conjugates of the present invention may be formulated with a physiologically acceptable support, vehicle or excipient for use as pharmaceuticals for both veterinary, for example in mammals, and particularly human use by a variety of methods.

The invention pertains to uses of the conjugates of the present invention for therapeutic treatments as described infra. Thus, the scope of the invention extends to the use of a compound of the invention for the manufacture of a medicament (or pharmaceutical) for treating or preventing a disorder as described supra. Accordingly, the conjugates of the present invention can be incorporated into compositions, preferably pharmaceutical compositions, suitable for administration. Such compositions typically comprise at least one conjugate according to the present invention or a mixture of conjugates and optionally, a pharmaceutically acceptable vehicle.

As used herein "pharmaceutically acceptable vehicle" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with an active conjugate of the invention, use thereof in the compositions is contemplated. Supplementary active compounds can also be incorporated into the compositions.

A composition of the invention, preferably pharmaceutical composition, is formulated to be compatible with its intended route of administration. Examples of routes of administration include intravenous bolus or infusion, intradermal, subcutaneous, intraperitoneal, intramuscular, oral (e.g., inhalation), transdermal (e.g., topical), intra-cranial, intra-spinal, and transmucosal administration. Solutions or suspensions used for these routes of administration can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable vehicles include physiological saline, bacteriostatic water, Cremophor EL™

(BASF, Parsippany, N.J.) or phosphate buffered saline (PBS). In all cases, the composition must be sterile and should be fluid to the extent that it can be administered. It must be stable under the conditions of manufacture and storage and must be preserved against the contaminating action of microorganisms such as bacteria and fungi. The vehicle can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the conjugate of the invention in the required amount in an appropriate solvent with one or a combination of ingredients enumerated above, as required, followed by sterilizing filtration. Generally, dispersions are prepared by incorporating the active conjugate of the invention into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible vehicle. They can be enclosed in gelatin capsules or compressed into tablets. For the purpose of oral therapeutic administration, the active conjugate of the invention can be incorporated with excipients and used in the form of tablets, troches, or capsules. Oral compositions can also be prepared using a fluid vehicle for use as a mouthwash, wherein the conjugate of the invention in the fluid vehicle is applied orally, swished, expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

For administration by inhalation, the conjugates of the invention are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active conjugates of the invention are formulated into ointments, salves, gels, or creams as generally known in the art.

The conjugates of the invention can also be prepared in the form of suppositories (e.g., with conventional suppository bases such as cocoa butter and other glycerides) or retention enemas for rectal delivery.

In one embodiment, the active conjugates of the invention are prepared with vehicles that will protect the conjugate of the invention against rapid elimination from the body, such as a controlled release formulation, including implants and micro- or macroencapsulated delivery systems. Biodegradable, biocompatible polymers can be used, such as ethylene vinyl acetate, polyanhydrides, polyglycolic acid, collagen, polyorthoesters, polyethylene glycols, and polylactic acid, or combination thereof.

Methods for preparation of such formulations will be apparent to those skilled in the art. The materials can also be obtained commercially from Alza Corporation for example and can also be used as pharmaceutically acceptable vehicles. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active conjugate of the invention calculated to produce the desired therapeutic effect in association with the required pharmaceutical vehicle. The specification for the dosage unit forms of the invention are dictated by and directly dependent on the unique characteristics of the active conjugate of the invention and the particular therapeutic effect to be achieved, and the limitations inherent in the art of compounding such an active conjugate of the invention for the treatment of individuals.

Toxicity and therapeutic efficacy of such conjugates of the invention can be determined by standard pharmaceutical procedures in cell cultures or experimental animals models, e.g., for determining the MTD (Maximum Tolerated Dose), TGI (tumor growth inhibition (TGI %) defined as 100-T/C (%)) and the T/C (ratio of mean tumor volume in treated animals to mean tumor volume in control groups). The dose ratio between therapeutic effects and toxic is the therapeutic index and it can be expressed as the ratio ED50/LD50. Conjugates of the invention that exhibit larger therapeutic indices are preferred. Although conjugates of the invention that exhibit toxic side effects may be used, care should be taken to design a delivery system that targets such conjugates of the invention to the site of affected tissue in order to minimize potential damage to non-tumor cells and, thereby, reduce side effects.

The data obtained from the animal studies can be used in formulating a range of dosage for use in humans. The dosage of such conjugates of the invention lies preferably within a range that includes the effective dose level with acceptable or no toxicity. The dosage may vary within this range depending upon the dosage form employed and the route of administration utilized. For any conjugate of the invention used in the method of the invention, the therapeutically effective dose can be estimated initially from assays on animal models. Such information can be used to more accurately determine useful doses in humans.

A therapeutically effective amount (i.e., an effective dosage) of a composition containing a conjugate of the invention is easily determined by one skilled in the art. For example, a therapeutically effective amount is an amount that inhibits tumor growth of xenografted human cancers by at least 20 percent. Higher percentages of inhibition, e.g., 45, 50, 75, 85, 90 percent or higher may be preferred in certain embodiments. Exemplary doses include milligram or microgram amounts of the compound of the present invention per kilogram of subject weight (e.g., about 1 microgram per kilogram to about 1 gram per kilogram, about 1 microgram per kilogram to about 50 micrograms per kilogram, or about 50 micrograms per kilogram to about 5 milligrams per kilogram). The compositions can be administered at least once per week, but also once every day or every 2, 3, 4, 5 or 6 days, for between about 1 to 10 weeks, e.g., between 2 to 8 weeks, or between about 3 to 7 weeks, or for about 4, 5, or 6 weeks.

One skilled in the art will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments.

It is furthermore understood that appropriate doses of a composition depend upon the potency of composition with respect to the expression or activity to be modulated.

When one or more of these compounds of the invention is to be administered to an animal (e.g., a human), a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound of the invention employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration.

In a particular embodiment, the compounds of the present invention may be administered simultaneously or sequentially with other therapeutic regimens or agents (e.g. multiple drug regimens), in a therapeutically effective amount. In particular, other therapeutic regimens or agents correspond to anti-cancer treatments or drugs, such as 5-fluorouracil, leucovorin, oxaliplatine, capecitabine, vincristine, celebrex, temozolomide, oligoelements (e.g., selenium), thalidomide, cetuximab, gemcitabine, docetaxel, 3-AP (Triapine®), carboplatine, bortezomib, bevacizumab, sorafenib, cisplatin, gefitinib, flavopiridol, elvorine, carboplatin, amrubicin, trastuzumab, pemetrexed, erlotinib, mitomycin C, AMG706, panitumumab, paclitaxel, raltitrexed, imatinib, abciximab, infliximab, palivizumab, rituximab, gemtuzumab ozogamicin, alemtuzumab or ibritumomab tiuxetan.

When simultaneous administration is performed, the active agents can be administered in the same or different compositions. This cotreatment aims to increase the therapeutic benefit and/or decreasing the toxicity.

In another particular embodiment, the present invention relates to the combination of radiotherapy and the compounds of the invention administered either concurrently or sequentially.

According to another aspect, the present invention relates to a use of an effective amount of at least one compound of the invention as defined above for the preparation of a pharmaceutical composition for the treatment of a disease, in particular cancers.

Preferred compounds for use according to the invention include any sub-group as defined above and any specific compounds as identified above.

A further object of this invention is a method for the treatment of a cancer, comprising administering to a patient in need of such treatment an effective amount of at least one compound as described above.

Because of the drug moiety comprised in the conjugate of the present invention, the conjugates of this invention are suitable for treating a variety of diseases in a variety of conditions. In this regard, "treatment" or "treating" include both therapeutic and prophylactic treatments. Accordingly, the conjugates may be used at very early stages of a disease, or after significant progression, including metastasis. The term "treatment" or "treating" designates in particular a reduction of the burden in a patient, such as a reduction in cell proliferation rate, a destruction of diseased proliferative cells, a reduction of tumor mass or tumor size, a reduction in tumor metastases, a delaying of tumor progression, as well as a complete tumor suppression, improvement of survival or any other appropriate clinical enpoint.

The conjugates of this invention are particularly suited for the treatment of cancers, such as solid tumors or lymphoid tumors. Specific examples include colon cancer, lung cancer (i.e. small cell, non-small cell, bronchic cancers), pancreas cancer, ovarian cancer, breast cancer, prostate cancer, liver cancer, head, stomach and neck cancer, bladder cancer, non-Hodgkin's lymphoma, melanoma, leukaemia, neuroblastoma and glioblastoma.

The conjugates may be administered according to various routes, typically by injection, such as systemic injection(s). The preferred route of administration is intravenously, either by bolus or by infusion, during 15 minutes to as long as 1 or 2 days. However, other administration routes may be used as well, such as intramuscular, intradermic, subcutaneous, intratumoral, etc. Furthermore, repeated injections can be performed, if needed.

A further object of this invention is a method for reducing cancer cell proliferation by administering in a subject having cancer an effective amount of conjugate according to the invention.

A further object of this invention is a method for treating metastatic cancers by administering in a subject in need of such treatment an effective amount of conjugate according to the invention.

A further object of this invention is the use of a conjugate as defined above for the preparation of a pharmaceutical composition for treating metastatic cancers or for reducing cancer cell proliferation.

Further aspects and advantages of this invention will be disclosed in the following examples, which should be regarded as illustrative and not limiting the scope of this application.

EXAMPLES

I. Material and Methods
I.1a Cell-Penetrating Peptides (CPPs)

```
DPV3:   Arg Lys Lys Arg Arg Arg Glu Ser Arg Lys Lys Arg Arg Arg Glu    (SEQ ID NO. 1)
Ser

DPV1047: Val Lys Arg Gly Leu Lys Leu Arg His Val Arg Pro Arg Val Thr   (SEQ ID NO. 8)
Arg Met Asp Val

DPV15:  Leu Arg Arg Glu Arg Gln Ser Arg Leu Arg Arg Glu Arg Gln Ser    (SEQ ID NO. 10)
Arg

DPV15b: Gly Ala Tyr Asp Leu Arg Arg Arg Glu Arg Gln Ser Arg Leu Arg    (SEQ ID NO. 11)
Arg Arg Glu Arg Gln Ser Arg

DPV7:   Gly Lys Arg Lys Lys Lys Gly Lys Leu Gly Lys Lys Arg Asp Pro    (SEQ ID NO. 3)

Tat48-60: Gly Arg Lys Lys Arg Arg Gln Arg Arg Arg Pro Pro Gln          (SEQ ID NO. 44)

Penetratin: Arg Gln Ile Lys Ile Trp Phe Gln Asn Arg Arg Met Lys Trp    (SEQ ID NO. 29)
Lys Lys DPV51(D): D-Lys D-Arg Gly D-Leu D-Lys D-Leu D-Arg D-His                (SEQ ID NO. 51)

DPV1047(D): Val Lys Arg Gly Leu Lys Leu Arg His Val Arg Pro            (SEQ ID NO. 8 in a D conformation)
Arg Val Thr Arg Met Asp Val
```

In order to allow the conjugation between the CPP and the linker-SN38 moiety (see example I.4):

- DPV3, DPV15, DPV7 and Tat48-60 further contain a cysteine (Cys) at the C terminal position of the amino acid sequence.
- DPV1047, DPV15b, Penetratin and DPV51 further contain a cysteine (Cys) at the N terminal position of the amino acid sequence.

The amino acid sequences were synthesized by Neosystem, France.

I.1b Non Cell-Penetrating Peptide

PolyE$_{(16)}$: Glu Glu Glu Glu Glu Glu Glu Glu Glu Glu Glu Glu Glu Glu Glu Glu (SEQ ID NO. 52)

In order to allow the conjugation between the PolyE$_{(16)}$ and the linker-SN38 moiety (see example I.4), PolyE$_{(16)}$ further contains a cysteine (Cys) at the N terminal position of the amino acid sequence.

The amino acid sequence was synthesized by Neosystem, France.

I.2 Linking Moieties (Linkers)

Linker #1:

N-3-Maleimidopropanoic acid (PIERCE, France, product Ref: 22296)

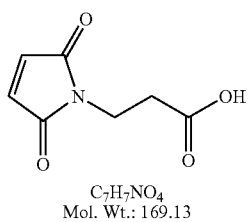 [SMILES: O=C(O)CCN1C(=O)C=CC1=O]

$C_7H_7NO_4$
Mol. Wt.: 169.13

Linker #2 (Also Named "MIC"):

N-6-Maleimidocaproic acid (SIGMA, France, Product Ref: M8904)

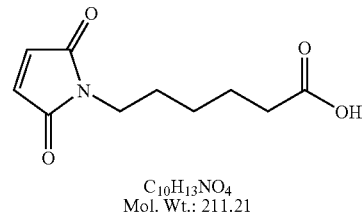 [SMILES: O=C(O)CCCCCN1C(=O)C=CC1=O]

$C_{10}H_{13}NO_4$
Mol. Wt.: 211.21

Linker #3:

P N-11-Maleimidoundecanoic acid (PIERCE, France, Product Ref: 22211)

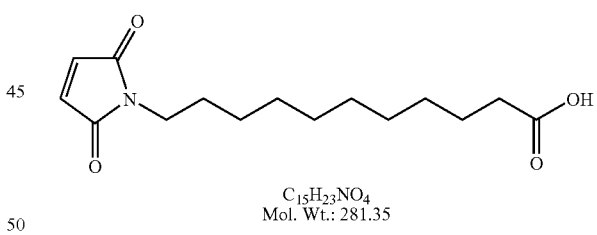

$C_{15}H_{23}NO_4$
Mol. Wt.: 281.35

Linker #4:

4-(N-maleimidomethyl)cyclohexane-1-carboxy-6-amidocaproic acid

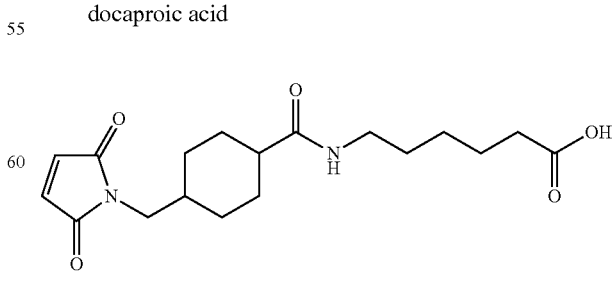

$C_{18}H_{26}N_2O_5$
Mol. Wt.: 350.41

Linker #5 (Also Named "BCH")
4-[((N-maleimidomethyl)cyclohexanecarboxamido)methyl]cyclohexanecarboxylic acid

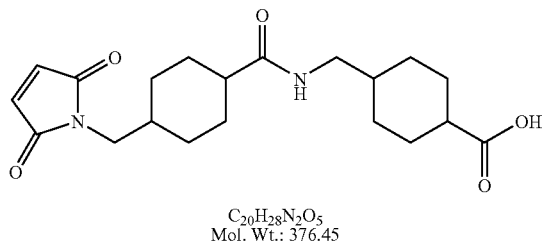 [SMILES: O=C(O)C1CCC(CNC(=O)C2CCC(CN3C(=O)C=CC3=O)CC2)CC1]

C$_{20}$H$_{28}$N$_2$O$_5$
Mol. Wt.: 376.45

Linker #6:
4-[(N-maleimidoethyl)carboxamidoethyl(Peg)$_4$carboxamidomethyl]cyclohexanecarboxylic acid

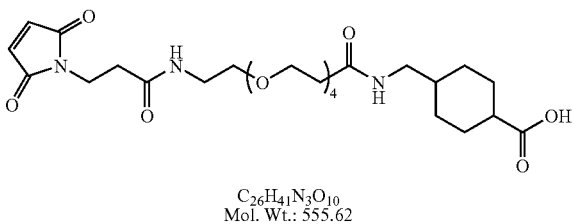

C$_{26}$H$_{41}$N$_3$O$_{10}$
Mol. Wt.: 555.62

Linker #7:
4-[(N-maleimidomethyl)cyclohexane-1-carboxy-6-amidohexanecarboxamidomethyl]cyclohexanecarboxylic acid

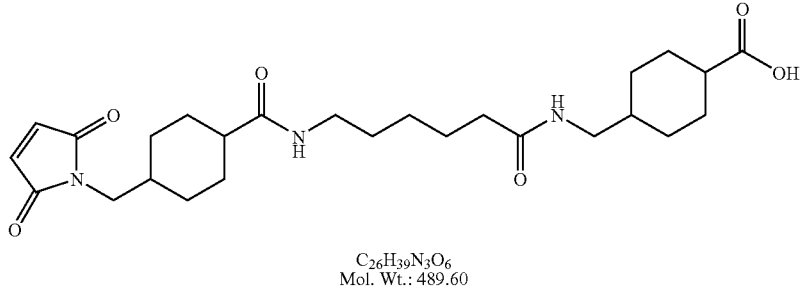 [SMILES: O=C(CCCCCNC(=O)C1CCC(CN2C(=O)C=CC2=O)CC1)NCC1CCC(C(=O)O)CC1]

C$_{26}$H$_{39}$N$_3$O$_6$
Mol. Wt.: 489.60

I.3 Synthesis of the Linkers 4 to 7

I.3.1 Synthesis of Linker #4

A solution of succinimidyl 4-[N-maleimidomethyl]cyclohexane-1-carboxylate (PIERCE Ref: 22360) (25 mmol) in DMF (100 mL) was stirred for 5 min, and was added at room temperature to a solution of 6-aminohexanoic acid (50 mmol) (SIGMA Ref: A2504) in H$_2$O (50 mL). The mixture was stirred for 4 h at room temperature. Dichloromethane was added (100 mL) and the organic layer was washed with water (3×150 mL) and then with 5% aqueous citric acid (3×150 mL) to remove 6-aminohexanoic acid excess. The organic layer was dried under vacuum and the resulting white powder was stored at −20° C.

I.3.2 Synthesis of Linker #5 ("BCH")

A solution of succinimidyl 4-[N-maleimidomethyl]cyclohexane-1-carboxylate (PIERCE Ref: 22360) (25 mmol) in DMF (100 mL) was stirred for 5 min, and was added at room temperature to a solution of trans-4-(aminomethyl)cyclohexanecarboxylic acid (50 mmol) (SIGMA ref: 08455) in H$_2$O (50 mL). The mixture was stirred for 4 h at room temperature. Dichloromethane was added (100 mL) and the organic layer was washed with water (3×150 mL) and then with 5% aqueous citric acid (3×150 mL) to remove trans-4-(aminomethyl)cyclohexanecarboxylic acid excess. The organic layer was dried under vacuum and the resulting white powder was stored at −20° C.

I.3.3 Synthesis of Linker #6

A solution of Mal-dPeg$_4$-NHS (Quanta BioDesign Ref: 10214) (25 mmol) in DMF (100 mL) was stirred for 5 min, and was added at room temperature to a solution of trans-4-(aminomethyl)cyclohexanecarboxylic acid (50 mmol) (SIGMA ref: 08455) in H$_2$O (50 mL). The mixture was stirred for 4 h at room temperature. Dichloromethane was added (100 mL) and the organic layer was washed with water (3×150 mL) and then with 5% aqueous citric acid (3×150 mL) to remove trans-4-(aminomethyl)cyclohexanecarboxylic acid excess. The organic layer was dried under vacuum and the resulting white powder was stored at −20° C.

I.3.4 Synthesis of Linker #7

A solution of succinimidyl 4-[N-maleimidomethyl]cyclohexane-1-carboxy-[6-amidocaproate]) (PIERCE Ref: 22362) (25 mmol) in DMF (100 mL) was stirred for 5 min, and was added at room temperature to a solution of trans-4-(aminomethyl)cyclohexanecarboxylic acid (50 mmol) (SIGMA ref: 08455) in H$_2$O (50 mL). The mixture was stirred for 4 h at room temperature. Dichloromethane was added (100 mL) and the organic layer was washed with water (3×150 mL) and then with 5% aqueous citric acid (3×150 mL) to remove trans-4-(aminomethyl)cyclohexanecarboxylic acid excess. The organic layer was dried under vacuum and the resulting white powder was stored at −20° C.

I.4 Camptothecin and Derivatives Thereof

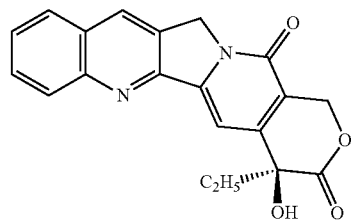

Camptothecin
C$_{20}$H$_{16}$N$_2$O$_4$
Mol. Wt.: 348.35

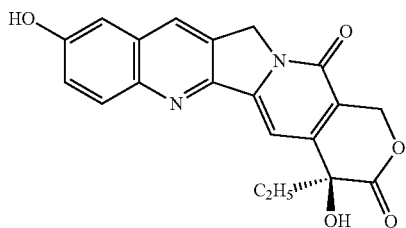

10-hydroxycamptothecin
$C_{20}H_{16}N_2O_5$
Mol. Wt.: 364.35

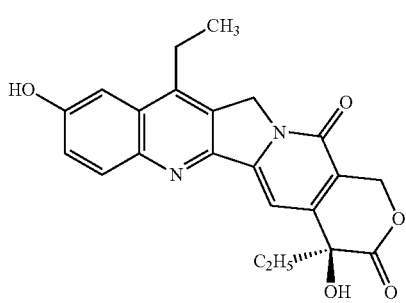

7-ethyl-10-hydroxycamptothecin
$C_{22}H_{20}N_4O_5S$
Mol. Wt.: 956.72

I.5 Method for the Preparation of the CPP-Linker-SN38 Conjugates

The CPP-linker-SN38 conjugates were prepared following the method described below. The same method has been used to conjugate the different CPPs to SN38 using the different linkers described above.

Preparation of 10-O-Linker-SN38

SN38 and "linker" undergo condensation mediated by O-(1H-6Chlorobenzotriazole-1-yl)-1,1,3,3-tetramethyluronium in N-methyl-2-pyrrolidinone. After extraction with dichloromethane and N-methyl-2-pyrrolidinone removal by aqueous washes, the intermediate linker-SN38 was isolated and purified by precipitation from dichloromethane/methyl tert-butyl ether.

Example of Synthesis Pathway:

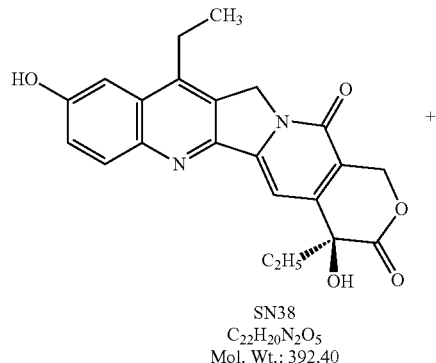

SN38
$C_{22}H_{20}N_2O_5$
Mol. Wt.: 392.40

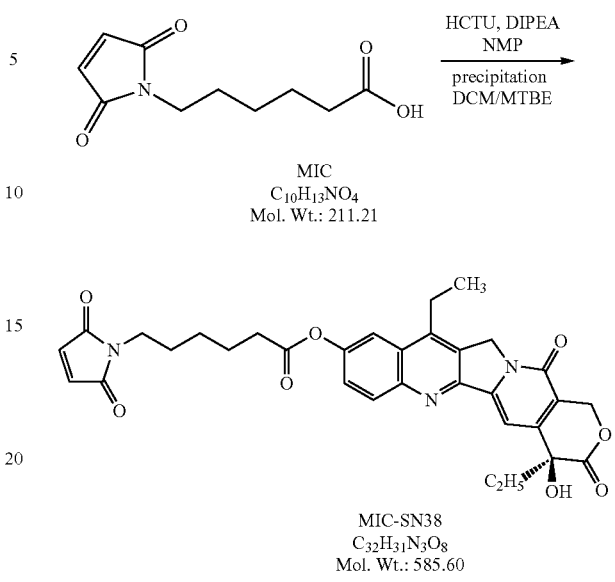

MIC
$C_{10}H_{13}NO_4$
Mol. Wt.: 211.21

MIC-SN38
$C_{32}H_{31}N_3O_8$
Mol. Wt.: 585.60

A solution of linker (15.29 mmol, for example 3.23 g for MIC) and O-(1H-6-Chlorobenzotriazole-1-yl)-1,1,3,3-tetramethyluronium (HCTU) (6.1 g, 14.74 mmol) and diisopropylethylamine (DIPEA) (5.4 mL, 30.9 mmol) in N-methyl-2-pyrrolidinone (NMP) (50 mL) at 0° C. was stirred for 15 min. To this reaction mixture was added SN38 (5 g, 12.75 mmol) as yellow solid powder. The mixture was stirred for 2 hours at 0° C. The solution was taken up in dichloromethane (130 mL), extracted successively with NaCl 1M (3×130 mL) and then with 5% aqueous citric acid (3×130 mL). The organic layer was added slowly (over a minimum of 30 minutes) to methyl tert-butyl ether (MTBE) (600 mL) at 0° C. The yellow precipitate that formed was then filtered and dried under vacuum (200 mBar) overnight.

Coupling of CPPs to 10-O-Linker-SN38

The linker-SN38 moiety was conjugated to the CPP to give a mixture of the CPP-linker-SN38 conjugate in DMF (dimethyl formamide). The product was extracted in water and lyophilised to give a yellow solid.

Example of Synthesis Pathway:

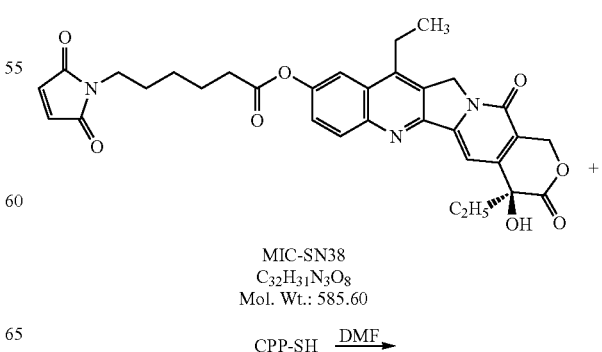

MIC-SN38
$C_{32}H_{31}N_3O_8$
Mol. Wt.: 585.60

CPP-SH $\xrightarrow{DMF}$

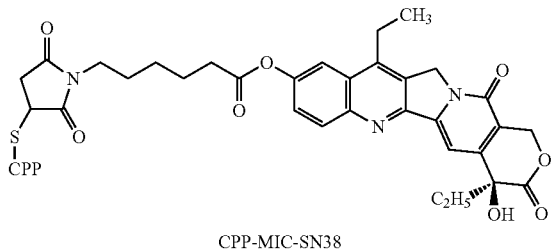

CPP-MIC-SN38

A solution of CPP-SH (5.69 mmol), for example DPV1047 containing a cysteine at N-ter position (21.49 g), in dimethylformamide (DMF) (200 mL) was stirred for 5 min, at room temperature. Then, 10-O-linker-SN38 (5 g, 8.54 mmol) was added as yellow solid powder. The mixture was stirred for 3 h at room temperature. Water was added (200 mL) and the aqueous layer was extracted with dichloromethane (5×150 mL) to remove 10-O-linker-SN38 excess. The aqueous layer was stored at −80° C. 4 h and then lyophilized. CPP-linker-SN38 conjugate was stored at −20° C. The net content of CPP-linker-SN38 was determined by HPLC. Comparison with a SN38 standard curve (364 nm) allowed the net content to be calculated.

Preparation of 10-O-Linker-Hydroxycamptothecin

10-Hydroxycamptothecin and "linker" undergo condensation mediated by O-(1H-6-Chlorobenzotriazole-1-yl)-1,1,3,3-tetramethyluronium in N-methyl-2-pyrrolidinone. After extraction with dichloromethane and N-methyl-2-pyrrolidinone removal by aqueous washes, the intermediate 10-O-linker-Hydroxycamptothecin was isolated and purified by precipitation from dichloromethane/methyl tert-butyl ether.

Example of Synthesis Pathway:

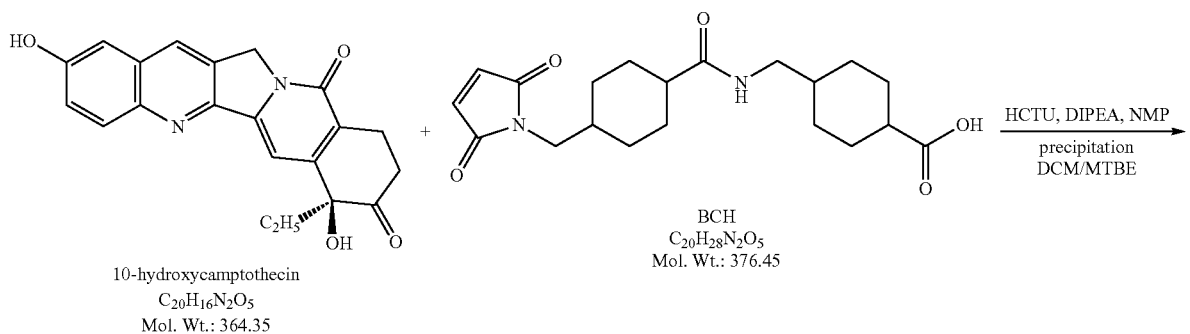

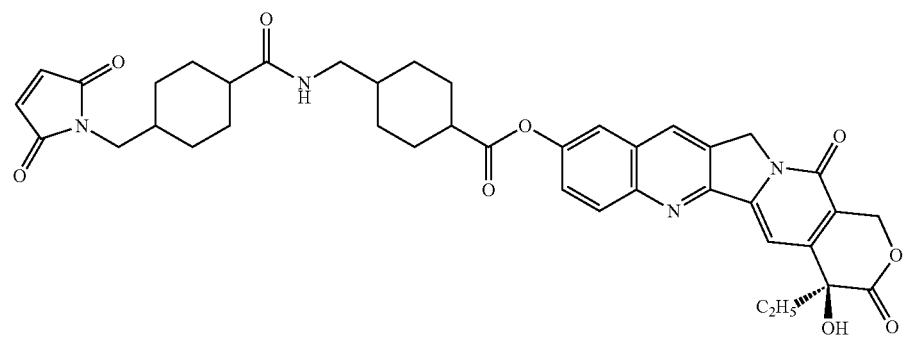

A solution of linker (16.47 mmol, e.g., 6.20 g for BCH) and O-(1H-6-Chlorobenzotriazole-1-yl)-1,1,3,3-tetramethyluronium (HCTU) (6.53 g, 15.78 mmol) and diisopropylethylamine (DIPEA) (5.74 mL, 32.94 mmol) in N-methyl-2-pyrrolidinone (NMP) (50 mL) at 0° C. was stirred for 15 min. To this reaction mixture was added 10-Hydroxycamptothecin (5 g, 13.72 mmol) as yellow solid powder. The mixture was stirred for 2 hours at 0° C. The solution was taken up in dichloromethane (130 mL), extracted successively with NaCl 1M (3×130 mL) and then with 5% aqueous citric acid (3×130 mL). The organic layer was added slowly (over a minimum of 30 minutes) to methyl tert-butyl ether (MTBE) (600 mL) at 0° C. The yellow precipitate that formed was then filtered and dried under vacuum (200 mBar) overnight.

Coupling of CPPs to 10-O-Linker-Hydroxycamptothecin

The 10-O-linker-Hydroxycamptothecin was conjugated to the CPP to give a mixture of the CPP-10-O-linker-Hydroxycamptothecin conjugate in dimethylformamide. The product was extracted in water and lyophilised to give a yellow solid.

Example of Synthesis Pathway:

HPLC. Comparison with a 10-Hydroxycamptothecin standard curve (364 nm) allowed the net content to be calculated.

Preparation of 20-O-Linker #1-Camptothecin

Example of Synthesis Pathway:

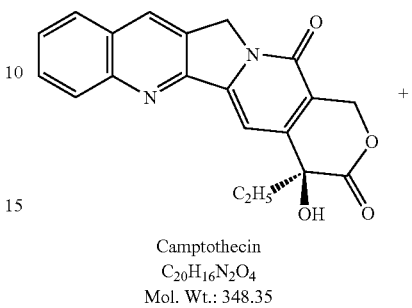

Camptothecin
$C_{20}H_{16}N_2O_4$
Mol. Wt.: 348.35

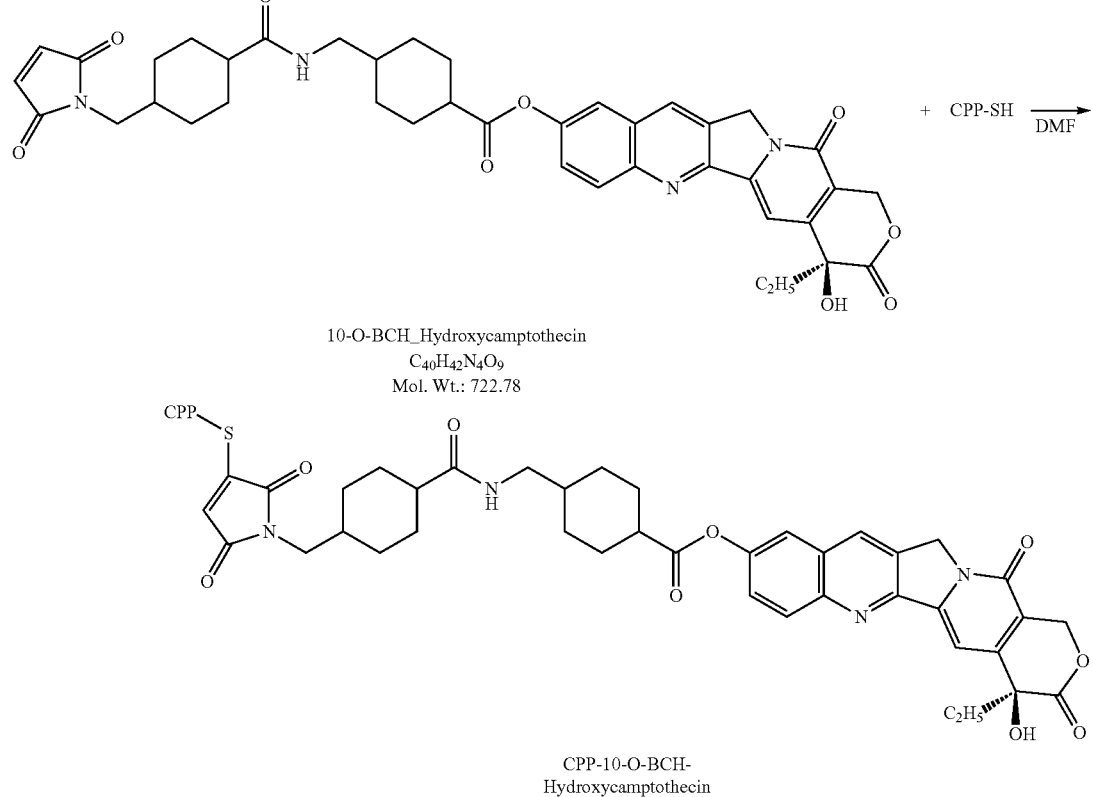

10-O-BCH_Hydroxycamptothecin
$C_{40}H_{42}N_4O_9$
Mol. Wt.: 722.78

CPP-10-O-BCH-Hydroxycamptothecin

A solution of CPP-SH (4.61 mmol), for example DPV1047 containing a cysteine at N-terminal position (17.42 g), in dimethylformamide (200 mL) was stirred for 5 min, at room temperature. Then, 10-O-linker-Hydroxycamptothecin (5.0 g, 6.92 mmol) was added as yellow solid powder. The mixture was stirred for 3 h at room temperature. Water was added (200 mL) and the aqueous layer was extracted with dichloromethane (5×150 mL) to remove 10-O-linker-Hydroxycamptothecin excess. The aqueous layer was stored at −80° C. 4 h and then lyophilized. CPP-10-O-linker-Hydroxycamptothecin conjugate was stored at −20° C. The net content of CPP-10-O-linker-Hydroxycamptothecin was determined by -continued

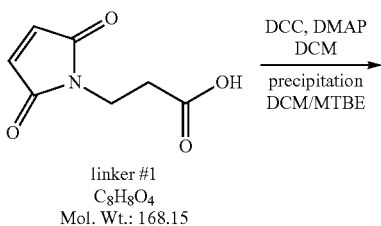

linker #1
$C_8H_8O_4$
Mol. Wt.: 168.15

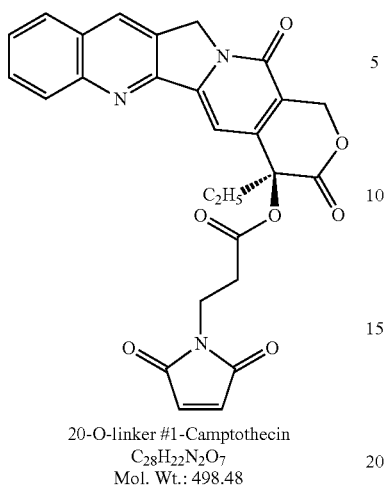

20-O-linker #1-Camptothecin
$C_{28}H_{22}N_2O_7$
Mol. Wt.: 498.48

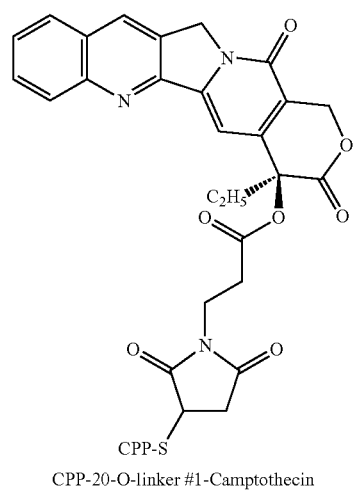

CPP-S
CPP-20-O-linker #1-Camptothecin

A solution of linker #1 (16.47 µmol, 2.78 mg) and dicyclohexylcarbodiimide (6.8 mg, 33 µmol) in 1 mL of dichloromethane at 0° C. was stirred for 12 hours. The formed precipitate (DCU, N,N'-dicyclohexylurea) was removed by filtration and the filtrate was added to Camptothecin (3.4 mg, 9.7 µmol) and DMAP (2 mg, 16.47 µmol), at +0° C. The mixture was stirred for 4 hours at 0° C. and then was extracted successively with NaCl 1M (3×1 mL) and with 5% aqueous citric acid (3×1 mL). The organic layer was added slowly to methyl tert-butyl ether (10 mL) at 0° C. The yellow precipitate that formed (20-O-linker #1-Camptothecin) was then filtered and dried under vacuum (200 mBar) overnight.

Coupling of CPPs to 20-O-Linker #1-Camptothecin

Example of Synthesis Pathway:

A solution of CPP-SH (4.61 µmol), for example DPV1047 containing a cysteine at N-terminal position (16.6 mg), in dimethylformamide (1 mL) was stirred for 5 min, at room temperature. Then, 20-O-linker #1-Camptothecin (3.4 mg, 7 µmol) was added as yellow solid powder. The mixture was stirred for 3 h at room temperature. Water was added (1 mL) and the aqueous layer was extracted with dichloromethane (5×1 mL) to remove 20-O-linker-Camptothecin excess. The aqueous layer was stored at −80° C. 2 h and then lyophilized. CPP-20-O-linker-Camptothecin conjugate was stored at −20° C. The net content of CPP-20-O-linker-Camptothecin was determined by HPLC. Comparison with a Camptothecin standard curve (364 nm) allowed the net content to be calculated.

Preparation of 20-O-Linker #5-Camptothecin

Example of Synthesis Pathway:

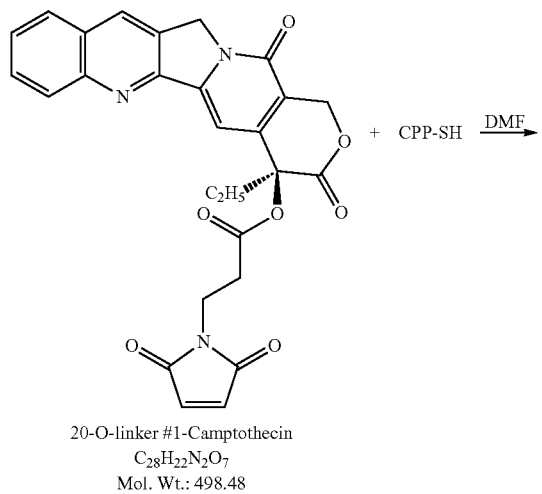

20-O-linker #1-Camptothecin
$C_{28}H_{22}N_2O_7$
Mol. Wt.: 498.48

+ CPP-SH $\xrightarrow{DMF}$

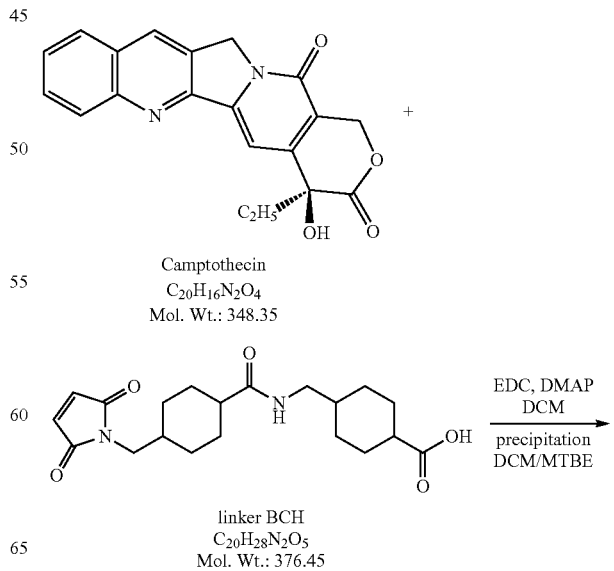

Camptothecin
$C_{20}H_{16}N_2O_4$
Mol. Wt.: 348.35 linker BCH
$C_{20}H_{28}N_2O_5$
Mol. Wt.: 376.45

$\xrightarrow[\text{precipitation DCM/MTBE}]{\text{EDC, DMAP DCM}}$

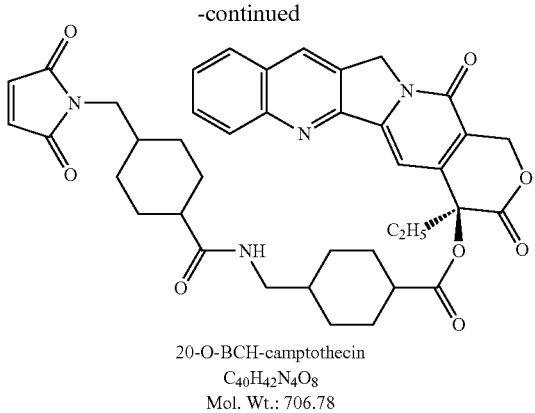

20-O-BCH-camptothecin
$C_{40}H_{42}N_4O_8$
Mol. Wt.: 706.78

To a solution of Camptothecin (10 mg, 28.7 µmol) in dichloromethane (10 mL) was added DMAP (10.5 mg, 86.2 µmol) and linker #5 (BCH, 21.6 mg, 57.7 µmol). The solution was stirred 5 minutes and then a solution of EDC (11.1 mg, 57.7 µmol) and triethylamine (12 µl, 86.2 µmol) in dichloromethane (50.5 mL) was added. The mixture was stirred for 18 hours at room temperature. The solution was extracted successively with NaCl 1M (3×10 mL) and then with 5% aqueous citric acid (3×10 mL). The organic layer was evaporated until a volume of 1 mL was obtained, and the solution was added slowly (over a minimum of 5 minutes) to methyl tert-butyl ether (20 mL) at 0° C. The yellow precipitate that formed was then filtered and dried under vacuum (200 mBar) overnight.

Coupling of CPPs to 20-O-Linker #5-Camptothecin
Example of Synthesis Pathway:

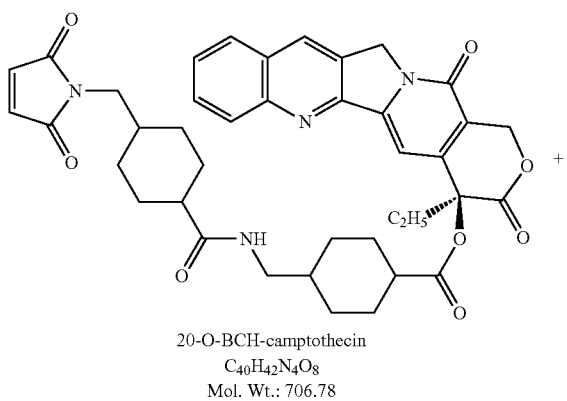

A solution of CPP-SH (4.61 µmol), for example DPV1047 containing a cysteine at N-terminal position (16.6 mg), in dimethylformamide (1 mL) was stirred for 5 min, at room temperature. Then, 20-O-linker-Camptothecin (5 mg, 7 µmol) was added as yellow solid powder. The mixture was stirred for 3 h at room temperature. Water was added (1 mL) and the aqueous layer was extracted with dichloromethane (5×1 mL) to remove 20-O-BCH-Camptothecin excess. The aqueous layer was stored at −80° C. for 2 h and then lyophilized. CPP-20-O-BCH-Camptothecin conjugate was stored at —20° C. The net content of CPP-20-O-linker-Camptothecin was determined by HPLC. Comparison with a Camptothecin standard curve (364 nm) allowed the net content to be calculated.

II Stability Study

In order to test the impact of the linker on the conjugate stability, different conjugates were synthesized with the same CPP but with different linkers.

CPP-Linker #1-SN38

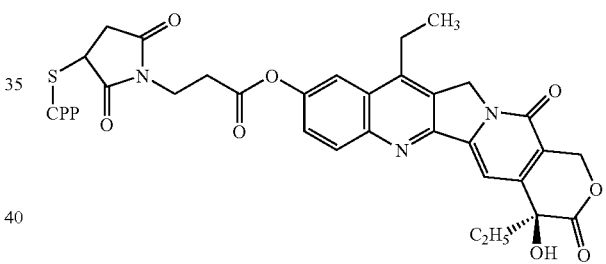

CPP-Linker #2-SN38

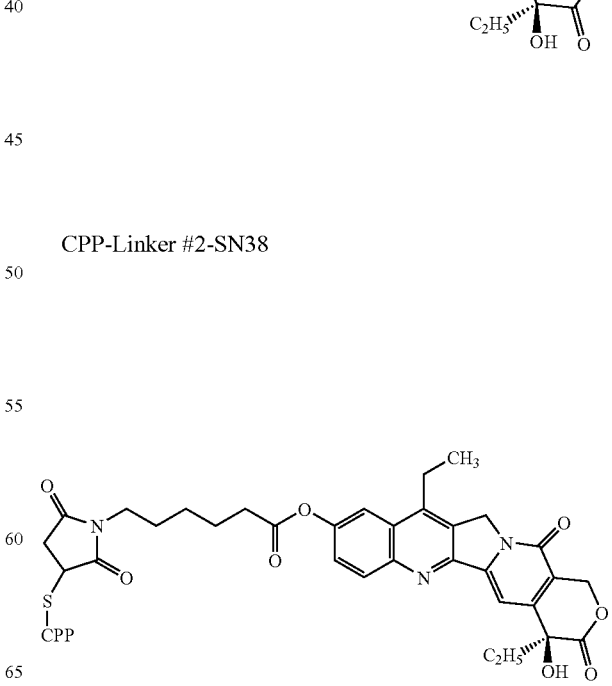

CPP-Linker #3-SN38
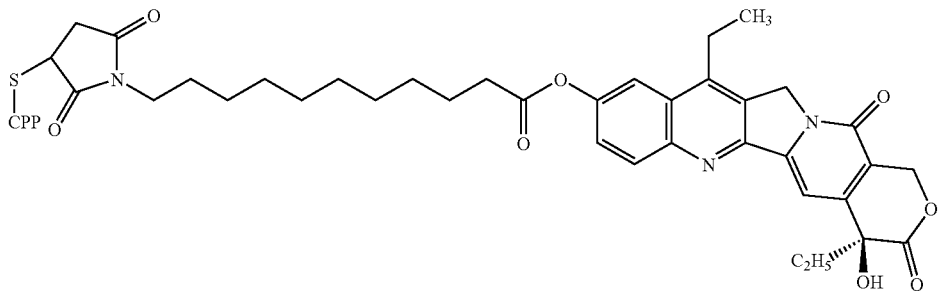
CPP-Linker #4-SN38
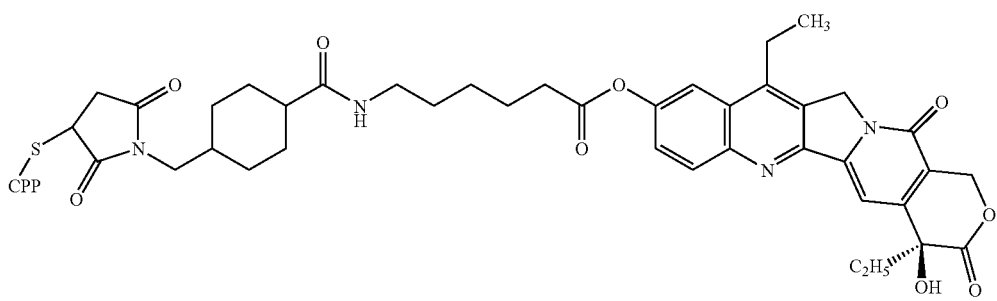
CPP-Linker #5-SN38
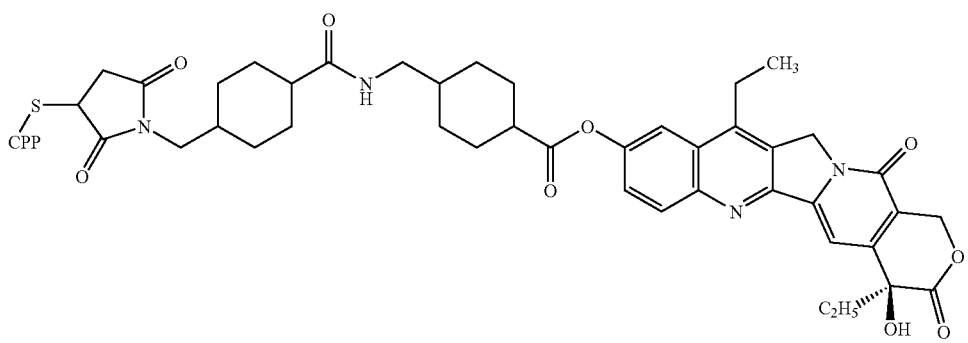
CPP-Linker #6-SN38
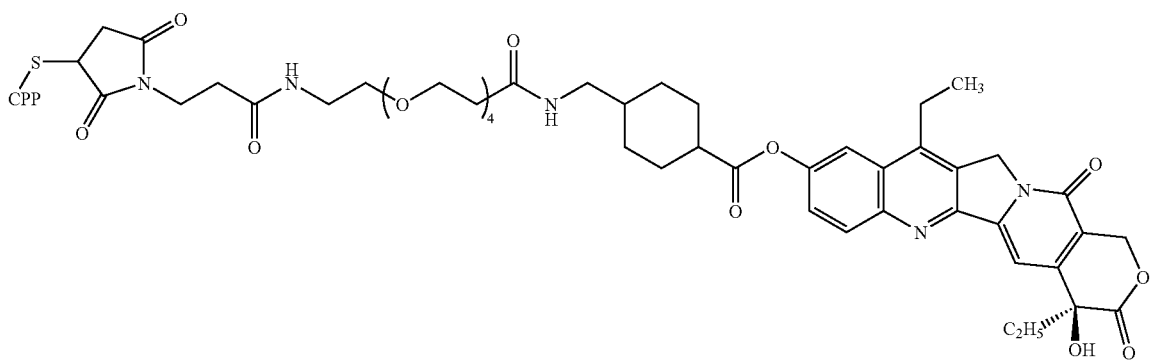

CPP-Linker #7-SN38

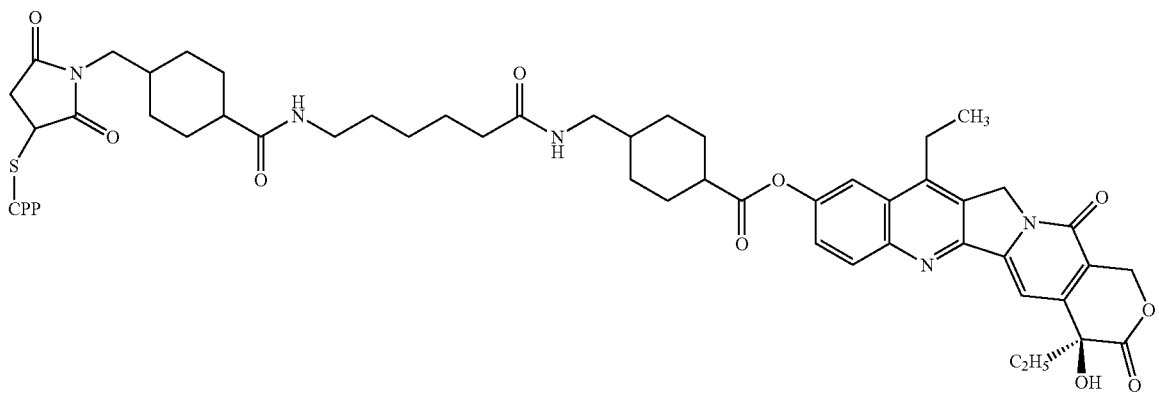

The stability of the conjugates was tested in citrated plasma (10% (v/v) sodium citrate buffer, 0.106M) from different species (see Table 1 below). The conjugates at 2.55 µM were incubated at 37° C. in plasma. Samples were analysed using the HPLC fluorescence method described below (see chromatographic equipment and conditions) following TFA/acetonitrile extraction and the amount of free camptothecin, analogs or derivatives thereof (e.g. SN38) released by the conjugates was measured.

Chromatographic equipment and conditions: 150 µL of each sample were placed in 1.5 mL micro-centrifuge tubes. 450 µL of 5% (v/v) TFA in $H_2O$ was added to each tube and the mixture was vortexed for 5 seconds. Samples were then centrifuged at 16000 g, 3 minutes at +4° C. 100 µL of supernatant were placed in 1.5 mL micro-centrifuge tubes. Methanol (100 µL) was then immediately added and vortexed for 5 seconds. Samples were then centrifuged at 16000 g, 3 minutes at room temperature. 150 µL of supernatant were recovered for HPLC analysis. Conjugates, metabolites and camptothecin derivative (i.e. SN38) were separated by high-performance liquid chromatography (HPLC; Agilent 1100 series equipped with a fluorescence detector) using a 4.6×100 mm (3 ηm particle size) Luna C18(2) column (Phenomenex ref. 00D-4251-E0, Le Pecq, France). The aqueous component of the mobile phase (A) was 0.1% (v/v) TFA in water. The organic modifier (B) was acetonitrile containing 0.1% (v/v) TFA. For the conjugate and its metabolites an elution gradient increasing linearly the proportion of B from 15 to 37% in 2 min, from 37 to 47% in 6 min, followed by 2 min at 90% was applied with a constant flow rate of 1.2 mL/min. The proportion of B was then returned to the initial condition for 3.0 min.

TABLE 1

Half life time (in minutes) of DPV1047-linker-SN38 in plasma at 37° C.

| DPV1047-linker-SN38 | Plasma origin and half life time | | | | |
|---|---|---|---|---|---|
| | Mouse | Rat | Human | Dog | Monkey |
| linker #1 | nd | nd | <5 min | nd | nd |
| linker #2 | <3 min | 3 min | 6-7 min | 36 min | 8 min |
| linker #3 | nd | nd | 8-9 min | nd | nd |
| linker #4 | <3 min | 3 min | 40 min | 105 min | 30 min |
| linker #5 | <3 min | 14 min | 400 min | 270 min | 290 min |
| linker #6 | nd | nd | 30 min | nd | nd |
| linker #7 | <3 min | 9 min | 150 min | 165 min | 90 min |

The half life time of conjugate corresponds to the time necessary to have 50% by mole of free camptothecin, analogs or derivatives thereof released by the conjugates of the invention. In human plasma, the half life time of conjugate DPV1047-linker #1-SN38 (less than 5 mins) was shorter than that of conjugate DPV1047-linker #2-SN38 (6-7 mins), which, in turn, was shorter than that of conjugate DPV1047-linker #3-SN38 (12 mins). The most stable conjugate was found to be DPV1047-linker #5-SN38 (400 mins), its half life time being 60 times longer than the DPV1047-linker #2-SN38 conjugate. The conjugate comprising linker #5 is also the most stable in rat plasma.

III Determination of the Efficacy of Four CPP-MIC-SN38 Conjugates in Human HCT 116 Xenograft Colon Tumor Model Implanted in Nude Mice An antitumor efficacy study was undertaken to identify CPP-linker #2-SN38 conjugates of interest (conjugates were generated as defined in Example I.4), using a Q4D×3 administration schedule (one injection every four days repeated three times) in female NMRi nude mice (6 weeks old) (Janvier, France) that carried HCT 116 tumors of human origin. HCT 116 tumor cells (ATCC Number: CCl-247) were established by an intradermal implantation of cell suspensions in the right flank of the mice. The first injection of drug was performed on day 3 after tumor cell implantation when the tumors had reached a size of roughly 100 mm³ (calculated with the following formula: [length×width²]/2), mice were randomized in groups of 6 and were treated with the CPP-MIC-SN38 at their previously determined Maximal Administrable Dose (MAD) by bolus intravenous injection at 10 µL/g in the lateral tail vein following a Q4D×3 administration schedule.

The minimal T/C % reflects the maximal tumor growth inhibition achieved.

During and following treatment clinical signs, body weight and tumor size were recorded in order to evaluate the efficacy and toxicity of the injected conjugates. The percentage ratio of the mean tumor volumes of drug treated versus vehicle treated groups (T/C×100) and the tumor growth inhibition (TGI %) defined as 100−T/C(%) were used to evaluate treatment efficacy.

The therapeutic parameters of four CPP-MIC-SN38 conjugates are summarized in Table 2 below.

TABLE 2

Efficacy of four CPP-MIC-SN38 conjugates in a model of HCT 116 human colorectal carcinoma tumor intradermaly implanted into nude mice

| CPP-MIC-SN38 conjugates | Injected dose (cumulative dose) µmol/kg | Schedule | Minimal T/C (%) (D) | TGI (%) |
|---|---|---|---|---|
| DPV3-MIC-SN38 | 10 (30) | Q4Dx3 | 68 (D11) | 32 |
| DPV15b-MIC-SN38 | 50 (150) | | 30 (D18) | 60*** |
| DPV15-MIC-SN38 | 30 (90) | | 27 (D13) | 63*** |
| DPV1047-MIC-SN38 | 40 (120) | | 28 (D14) | 62*** |

***p < 0.001 versus control (Dunnett test)
D = day when minimal T/C is reached

Three of the CPP-MIC-SN38 conjugates (DPV15b-MIC-SN38, DPV15-MIC-SN38 and DPV1047-MIC-SN38) exhibited significant anti-tumoral activity (TGI=60 to 63%) compared to the saline control, whilst the DPV3-MIC-SN38 conjugate exhibited only a moderate antitumoral activity (TGI=32%) in the HCT 116 tumor model.

No clinical signs of toxicity such as body weight loss, diarrhea or alopecia were observed during the study when the CPP-MIC-SN38 conjugates were administered at their MADs.

The conjugates administrable at high dose levels (30 to 50 µmol/kg) exhibited the greatest anti-tumoral activity compared to the saline control as demonstrated with DPV15b-MIC-SN38, DPV15-MIC-SN38 and DPV1047-MIC-SN38.

IV Evaluation of the Influence of the Linker Stability on the Therapeutic Efficacy of CPP-Linker-SN38 Conjugates in the Human HCT 116 Xenograft Colon Tumor Model Implanted in Nude Mice or in the Human LS 174T Xenograft Tumor Colon Model Implanted in Nude Rats The influence of linker stability on the efficacy of CPP-linker-SN38 was evaluated in two xenograft models. The linkers were selected based on their in vitro plasma stability: the MIC linker (linker #2) was relatively unstable in human plasma, whilst the BCH linker (linker #5) showed high human plasma stability. Four conjugates, DPV15-MIC-SN38, DPV1047-MIC-SN38, DPV15-BCH-SN38 and DPV1047-BCH-SN38, were characterised in mice. Two conjugates, DPV1047-MIC-SN38 and DPV1047-BCH-SN38, were characterised in rats.

Implantation and HCT 116 tumor growth was performed as described in example III. On the day of the first injection mice were randomized in groups of 6 and were treated with the CPP-linker-SN38 conjugates at the same equimolar dose (30 µmol/kg) by bolus intravenous injection at 10 µL/g in the lateral tail vein following a Q4Dx3 (one injection every four days three times) administration schedule.

The LS 174T study was performed using female nude rats (8 weeks old) purchased from Harlan breeding center (Gannat, France). LS 174T tumors were established by a subcutaneously implantation of cell (ATCC Number: CCl-188) suspensions in the right flank of the animals. The first injection of drugs was performed when the tumors reached a size of about 1000 mm$^3$. The tumor volume was calculated using the following formula: [length×width$^2$]/2. On the day of the first injection, rats were randomized in groups of 8 and were treated with the CPP-linker-SN38 conjugates at their previously determined MAD by bolus intravenous injection at 10 µL/g in the lateral tail vein following a Q3/4Dx5 (every three or four days five times) administration schedule.

During the course of the experiment, clinical signs, body weight and tumor size were controlled twice a week. The percentage ratio of the mean tumor volumes of treated versus vehicle (control) treated groups (T/C×100%) and the tumor growth inhibition (TGI %) defined as 100−T/C were used to evaluate treatment efficacy.

The minimal T/C % reflects the maximal tumor growth inhibition achieved.

The therapeutic parameters of the four CPP-linker-SN38 conjugates in HCT 116 tumor-bearing mice are summarized in Table 3.

TABLE 3

Influence of the two chemical linkers on the efficacy of CPP-linker-SN38 conjugates in a model of HCT 116 human colorectal carcinoma tumor intradermaly implanted into nude mice

| CPP-linker-SN38 conjugates | Dose (cumulative) µmol/kg | Schedule | Minimal T/C (%) (D) | TGI (%) |
|---|---|---|---|---|
| DPV1047-MIC-SN38 | 30 (90) | Q4Dx3 | 29 (D19) | 61*** |
| DPV15-MIC-SN38 | | | 27 (D17) | 63*** |
| DPV1047-BCH-SN38 | | | 10 (D14) | 80*** |
| DPV15-BCH-SN38 | | | 30 (D19) | 60*** |

***p < 0.001 versus control (Dunnett test)
D = day when minimal T/C is reached

All four conjugates showed significant anti-tumoral efficacy in the HCT 116 tumor model. DPV1047-BCH-SN38 (TGI=80%) was significantly more active than DPV1047-MIC-SN38 (TGI=60%), DPV15-BCH-SN38 (TGI=61%) and more active than DPV15-MIC-SN38 (TGI=63%).

No clinical signs of toxicity such as body weight loss, diarrhoea or alopecia were detected during the study when the CPP-MIC-SN38 or CPP-BCH-SN38 conjugates were administered at their MADs.

The efficacy of the two DPV1047-linker-SN38 conjugates in LS 174T tumor-bearing rats is presented in Table 4.

TABLE 4

Influence of the two chemical linking moieties on the efficacy of CPP-linker-SN38 conjugates in the LS 174T human colorectal carcinoma tumor model subcutaneously implanted into nude rats

| CPP-linker-SN38 conjugates | Dose (cumulative) µmol/kg | Schedule | Minimal T/C (%) (D) | TGI (%) |
|---|---|---|---|---|
| DPV1047-MIC-SN38 | 20 (100) | Q3/4Dx5 | 44 (D35) | 56*** |
| DPV1047-BCH-SN38 | | | 43 (D35) | 57*** |

***p < 0.001 versus control (Dunnett test)
D = day when minimal T/C is reached

Both DPV1047-MIC-SN38 and DPV1047-BCH-SN38 (TGI=56 to 57%) showed the same significant anti-tumoral activity in the LS 174T tumor model.

No clinical signs of toxicity such as body weight loss, diarrhea or alopecia were detected during the study when the CPP-MIC-SN38 or CPP-BCH-SN38 were administered at their MADs.

In the tumor-bearing mice, DPV1047-BCH-SN38 was the most active of the four conjugates tested. In tumor-bearing rats DPV1047-MIC-SN38 and DPV1047-BCH-SN38 exhibited the same activity.

V Comparative Efficacy of the DPV1047-BCH-SN38 Conjugate and Other SN38-Derivatives in Human HCT 116 Colon Tumor Model Implanted in Nude Mice The activity of the DPV1047-BCH-SN38 (=DPV 1047-linker #5-SN38) conjugate and SN38 derivatives using others delivery systems that allowed solubilization of the active molecule were compared. DPV1047-BCH-SN38 (shown above to have the greatest in vivo efficacy of all CPPs and linkers tested), was compared with: irinotecan, commercial soluble prodrug of SN38 (Campto®, Aventis) and a (Glutamic acid)$_{16}$Cys-MIC-SN38 conjugate ((Glutamic acid)$_{16}$Cys is SEQ ID NO:55) (PolyE$_{(16)}$-MIC- SN38) Pol E $_{16}$ )is SEQ ID NO:52). The PolyE $_{(16)}$ peptide (SEQ ID NO:52) was chosen as a non cell-penetrating-peptide according to the present invention and because of its biocompatibility, nontoxic properties, hydrophilicity and solubilization properties.

Implantation and HCT 116 tumor growth was performed as described above. The day of the first injection mice were randomized in groups of 6 and were treated with different conjugates following their optimal administration conditions (see Table 5) by bolus intravenous injection at 10 μL/g in the lateral tail vein.

During the course of the experiment clinical, signs, body weight and tumor size were controlled twice a week. The percentage ratio of the mean tumor volumes of drug treated versus vehicle treated groups (T/C×100%) and the tumor growth inhibition (TGI %) defined as 100−T/C(%) were used to evaluate treatment efficacy.

The minimal T/C % reflects the maximal tumor growth inhibition achieved.

The therapeutic parameters of the different SN38 conjugates are summarized in Table 5.

TABLE 5

Comparative efficacy of DPV1047-BCH-SN38 conjugate and other SN38-derivatives in a model of HCT 116 human colorectal carcinoma tumor intradermaly implanted into nude mice

| Therapeutic molecules | Doses (cumulative) μmol/kg | Schedule | Minimal T/C (%) (D) | TGI (100-T/C %) |
|---|---|---|---|---|
| DPV1047-BCH-SN38 | 18 (90) | Q1D5 | 7 (D18) | 93*** |
|  | 30 (90) | Q4Dx3 | 10 (D14) | 90*** |
|  | 25 (225) | Q2D3x3W | 3 (D28) | 97*** |
| PolyE$_{(16)}$-MIC-SN38 | 40 (120) | Q4Dx3 | 70.0 (D18) | 30 |
| irinotecan | 18 (90) | Q1D5 | 10 (D18) | 90*** |
|  | 48 (144) | Q4Dx3 | 10 (D18) | 90*** |
|  | 48 (432) | Q2D3x3W | 1 (D28) | 99*** |

***p > 0.001 versus control (Dunnett test)
D = day when minimal T/C is reached

The DPV1047-BCH-SN38 exhibited a similar TGI whatever the administration schedule in the HCT 116 tumor model. The Q2D3×3W schedule induced a more prolonged activity than two other schedules.

The PolyE$_{(16)}$-MIC-SN38 although administered at a high dose level (40 μmol/kg) using the Q4D×3 administration schedule, was not active in this model. The solubilization of SN38 by conjugation with the hydrophilic peptidic sequence PolyE$_{(16)}$ was not sufficient to allow effective delivery of SN38 in an active form in vivo.

DPV1047-BCH-SN38 and irinotecan exhibited the best efficacy following a Q2D3×3W schedule that resulted in a prolonged tumor growth inhibition with a minimal T/C % after 28 days.

In the efficacy studies in mice irinotecan showed a similar activity to that of DPV1047-BCH-SN38 whatever the administration schedule. In mice the conversion of irinotecan to SN38 is significantly higher than in humans, due to interspecies variation in carboxylesterases, thus the efficacy of irinotecan is overestimated in mice models (J. Thompson et al., BBA 1998; 1400: 301-319).

No clinical signs of toxicity such as body weight loss, diarrhea or alopecia were observed during the study when the DPV1047-BCH-SN38 conjugate was administered at its MADs.

VI Comparative Toxicity and Pharmacokinetic Studies of DPV1047-BCH-SN38, DPV1047-MIC-SN38 and Irinotecan in the Dog The intestinal and hematological toxicities of the DPV1047-linker-SN38 conjugates compared to irinotecan, were evaluated in the beagle dog. The dog is an appropriate model as the metabolism of irinotecan in this species is similar to that of humans (M. Inaba et al., Cancer Chem. Pharmacol. 41: 130-108 (1998)) and because the dog displays the same symptoms of delayed diarrhea as observed in humans.

Adult female and male beagle dogs were individually housed with free access to tap water. A pellet diet was distributed daily.

Dogs (1 dog for each drug and dose) were infused intravenously through the cephalic or saphenous vein. These intravenous infusions were made using a single-use catheter (Intraflon®) and a plastic syringe connected to a syringe pump. During the injection, the animals were restrained in a hammock.

DPV1047-BCH-SN38 (DPV1047-linker #5-SN38) was administered at 5, 10 and 20 mg/kg by a 45 min infusion (0.3 to 0.4 mL/min). DPV1047-MIC-SN38 (DPV1047-linker #2-SN38) was administered at 10 and 20 mg/kg by a 20 min infusion and at 50 and 70 mg/kg by a 45 min infusion (0.3 to 0.4 mL/min). Irinotecan (clinical grade) was injected at its Maximal Tolerated Dose (MTD), i.e. 30 mg/kg (F. Lavelle et al., Seminar in Oncology (1996)) by a 20 min infusion (0.3 to 0.4 mL/min). Conjugates were dissolved in water for injection (10% of final volume) and diluted with 0.9% NaCl to their final concentration. The volume administered to each animal was adjusted according to body weight.

Clinical signs, hematological and intestinal toxicities were monitored during a period of 15 days after infusion. Each animal was checked at least twice a day for mortality or signs of morbidity.

The body weight of each animal was recorded on the day −1, 4, 10 and 13.

Peripheral blood samples were taken into EDTA tubes for the determination of following parameters on days −1, 5, 11 and 14: erythrocytes, hemoglobin, mean cell volume, packed cell volume, mean cell hemoglobin concentration, mean cell hemoglobin, thrombocytes, leucocytes, differential white cell count with cell morphology.

The dog treated with irinotecan exhibited the classical clinical signs of irinotecan toxicity (F. Lavelle I, Seminar in Oncology, 1996): early (Day 1) and late diarrhea (Days 4 to 6), body weight loss (−8.5%), emesis and a severe but reversible hematoxicity were reported on Day 5 (92% of white blood cells depletion, see Table 6 below).

The dogs treated with DPV1047-BCH-SN38 at 5 and 10 mg/kg showed no clinical signs and only a moderate but non-dose dependent decrease in white blood cell (WBC) counts, as has been observed for many cytotoxic molecules below their MTD. At 20 mg/kg of DPV1047-BCH-SN38 a significant decrease in white blood cells (93% reduction in WBCs) was observed, together with a decrease in food intake suggesting that the maximum tolerated dose (MTD) had been reached. At 30 mg/kg DPV1047-BCH-SN38 displayed clear toxicological signs including diarrhea and a severe hematoxicity.

The dogs treated with DPV1047-MIC-SN38 at 10, 20, 40 and 50 mg/kg showed no clinical signs and only a moderate reduction in white blood cells (WBC). DPV1047-MIC-SN38 at 70 mg/kg displayed signs of toxicity that included: gastrointestinal toxicity, diarrhea and emesis. A severe hematoxicity was reported (94% of WBC depletion).

These results indicate that the MTD for DPV1047-BCH-SN38 is around 20 mg/kg (2.6 mg equivalent of SN38) and between 50 and 70 mg/kg (6.5-9.1 mg equivalent of SN38) for DPV1047-MIC-SN38. DPV1047-BCH-SN38 is consequently more toxic than DPV1047-MIC-SN38.

The toxicity studies in the beagle dog of two different SN38 conjugates are summarized in Table 6.

TABLE 6

Toxicity studies in the beagle dog following infusion of irinotecan, DPV1047-BCH-SN38 and DPV1047-MIC-SN38

| Drug | Dose (mg/kg) | Toxic signs Day 1 | Following Days | Reduction in WBC at D5 (%) |
|---|---|---|---|---|
| irinotecan | 30 | Loss of balance Tremors (marked) Ptyalism Liquid feces (marked) Vomit | Vomit: D4 Liquid feces: D5&6 | −92 |
| DPV1047-BCH-SN38 | 5 | None | None | −60 |
|  | 10 | None | None | −50 |
|  | 10 | None | None | −57 |
|  | 20 | None | Decrease in food intake | −93 |
|  | 30 | None | Liquid faeces D4 | −96 |
| DPV1047-MIC-SN38 | 10 | None | None | −44 |
|  | 20 | None | None | −57 |
|  | 40 | None | None | −69 |
|  | 50 | None | None | −53 |
|  | 70 | Vomit | Liquid feces D4 | −94 |

WBC white blood cell, D day

As part of these studies, the pharmacokinetics of DPV1047-BCH-SN38, DPV1047-MIC-SN38, irinotecan, and their major metabolites were compared. Peripheral blood samples were taken at different times following infusion for pharmacokinetic analysis. For irinotecan and DPV1047-MIC-SN38 at 10 and 20 mg/kg, blood was sampled at time 0 (before infusion), just before the end of infusion (20 minutes) and 10, 20, 40, 220, 460 minutes after the end of infusion. For all other groups, blood was sampled at time 0 (before infusion), just before the end of infusion (45 minutes) and 10, 20, 40, 120, 220 minutes after the end of infusion.

Blood samples (2.5 mL) were collected in 5 mL in trisodium citrate tubes (Sarstedt S-Monovette® 9NC) containing 2.5 mL of 5% TFA (v/v) and vortexed for 5 seconds before storage at −80° C. (for less than two weeks).

Samples were then analyzed after a TFA and acetonitrile extraction by an HPLC fluorescence method, described below. They were thawed in a room temperature water bath for 5 minutes, diluted two fold with five milliliters of $H_2O$, containing 2.5% TFA (v/v). Whole blood samples were acidified with TFA to protect the ester link of the conjugate against hydrolysis and allow protein precipitation to improve conjugate and SN38 recovery.

Five hundred microliters of each sample were then placed in 1.5 mL micro-centrifuge tubes to and centrifuged at 16000×g 3 min at +4° C. One hundred microliters of supernatant were placed in 1.5 mL micro-centrifuge tubes followed by 20 μL of freshly prepared 1.12 μg/mL camptothecin solution (internal standard; kept at +4° C. in an ice-water bath no more than 4 hours). Methanol (100 μL) was then immediately added and the mixture stirred vigorously (vortex) for 5 seconds. Samples were then centrifuged at 16000×g, 3 min at room temperature.

One hundred and fifty microliters of the supernatant was recovered for HPLC analysis.

HPLC Analysis

DPV1047-BCH-SN38 and its metabolite SN38 were separated by high-performance liquid chromatography (HPLC Agilent 1100 with a fluorescence detector) using the following method:

Solvent A: 0.1% (v/v) TFA in $H_2O$
Solvent B: 0.1% (v/v) TFA in acetonitrile
Column: Luna, C18(2), 3 μM, 100×4.6 mm (Phenomenex ref. 00D-4251-E0)
Elution: 15-37% of B in 2 min, 37-47 in 6 min, to 90% of B in 0.5 min, followed by 2 min at 90% of B. 15% of B for 2 min.
Volume injected: 100 μL
Flow rate: 1.2 mL/min
Detection: fluorescence; excitation 375 nm, emission 560 nm (sensitivity 18)

DPV1047-MIC-SN38, irinotecan and their metabolite SN38 were separated by high-performance liquid chromatography (HPLC Agilent 1100 with a fluorescence detector) using the following method:

Solvent A: 0.1% (V/V) TFA in $H_2O$
Solvent B: 0.1% (V/V) TFA in acetonitrile
Column: Luna, C18(2), 3 μt, 100×4.6 mm (Phenomenex ref. 00D-4251-E0)
Elution: 15-50% of B in 10 min, to 90% of B in 0.5 min, followed by 2 min at 90% of B. 15% of B for 2 min.
Volume injected: 100 μL
Flow rate: 1.2 mL/min
Detection: fluorescence; excitation 375 nm, emission 560 nm (sensitivity 18)

FIG. 1 compares the blood exposure (AUC) to SN38 following DPV1047-BCH-SN38 and DPV1047-MIC-SN38 infusion at different doses compared to irinotecan at 30 mg/kg. At non-toxic doses of DPV1047-BCH-SN38 (doses ≦20 mg/kg) and DPV1047-MIC-SN38 (dose ≦%50 mg/kg), both the SN38 $C_{max}$ and AUC increased linearly with the dose of the conjugate. Following irinotecan infusion at 30 mg/kg (its MTD), the AUC of SN38 (irinotecan's active metabolite) is more than 80 fold lower than the AUC of SN38 following DPV1047-MIC-SN38 or DPV1047-BCH-SN38 infusion at doses around their respective MTDs. In contrast to irinotecan, DPV1047-linker-SN38 conjugates delivered significantly higher quantities of the active metabolite, SN38, in the blood at non-toxic doses. The AUC of SN38 is significantly greater following DPV1047-BCH-SN38 infusion compared to DPV1047-MIC-SN38 at an equimolar dose (FIG. 1).

Figure 2:
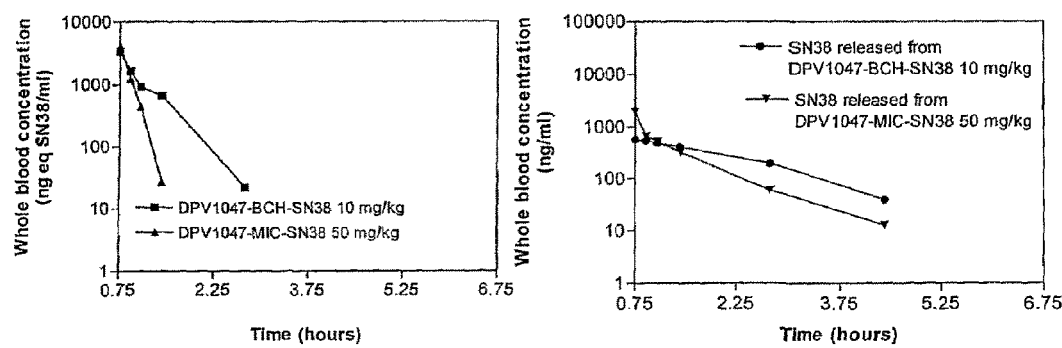
FIG. 2 shows the blood AUC of DPV1047-MIC-SN38, DPV1047-BCH-SN38 and SN38 following infusion of DPV1047-MIC-SN38 (50 mg/kg) and DPV1047-BCH-SN38 (10 mg/kg). ▲: DPV1047-MIC-SN38; ▼: SN38 from DPV1047-MIC-SN38; ■: DPV1047-BCH-SN38; ●: SN38 from DPV1047-BCH-SN38. AUC were measured from the end of infusion to the limit of quantification (7.8 ng/mL eq SN38); for DPV1047-MIC-SN38 and DPV1047-BCH-SN38 at their respective doses AUC=AUC 0-4.42 h.

The circulating half life time of DPV1047-BCH-SN38 in the blood is longer than for DPV1047-MIC-SN38 and as a consequence the AUC of SN38 delivered by DPV1047-BCH- SN38 is greater than that released by DPV1047-MIC-SN38 (FIG. 2). The increased toxicity observed with DPV1047-BCH-SN38 correlates well with the increased AUC of the active (cytotoxic) molecule, SN38.

Toxicity studies in dogs have shown that the DPV1047-BCH-SN38 conjugate is more toxic than the DPV1047-MIC-SN38 conjugate. Both the BCH and MIC conjugates exhibit the same toxicity profile characterized by gastrointestinal toxicity and hematoxicity. The MTD of the BCH conjugate is approximately three times lower than for the MIC conjugate, but correlates well with the liberation of significantly more SN38 from the BCH conjugate. A dose dependent increase in the AUC of SN38 was observed when DPV1047-BCH-SN38 was injected at doses between 5-20 mg/kg and when DPV1047-MIC-SN38 is injected between 10-50 mg/kg.

These results demonstrate that DPV1047-linker-SN38 conjugates are able to deliver significantly more circulating SN38 than irinotecan with significantly reduced toxicity. This is extremely important because it is well known that dose intensification with irinotecan in humans improves response to treatment due to higher exposure to active metabolite, SN38, (de Jonge M. J., et al., J Clin Oncol, 18: 195-203, 2000; Ychou, M., et al., Cancer Chemotherapy And Pharmacology, 50: 383-391, (2002)), and because such dose intensification is seldom possible due to the dose-limiting toxicity of irinotecan.

VII Evaluation of the in Vivo Efficacy of the DPV1047-BCH-SN38 Conjugate in a Range of Human Tumor Models Implanted in Rodents The activity of the DPV1047-BCH-SN38 conjugate was assessed in a number of different tumor models in order to determine the applicability of this conjugate to a wide range of tumor types. Five human tumor models were selected: the HCT 116 colorectal carcinoma model (ATCC Number: CCl-247), the LS 174T colorectal carcinoma model (ATCC Number: CCl-188), the HT-29 colorectal carcinoma model (ATCC Number: HTB-38), the NCI-H460 lung carcinoma (ATCC Number: HTB-177) and the MDA-MB-231 mammary carcinoma models (ATCC Number: HTB-26).

HCT 116, HT-29, NCI-H460 and MDA-MB-231 tumors were established by an intradermal or subcutaneous implantation of cells in the right flank of 7 week old female NMRi nude mice ($1 \times 10^7$, $1 \times 10^7$, $3 \times 10^6$ and $3 \times 10^6$ cells injected, respectively) (Janvier, France). LS 174T tumor cells were implanted into Rh rnu/rnu nude rats ($2 \times 10^7$ cells). Treatments were initiated when the tumors had reached a size of 100 mm$^3$ in mice or 1000 mm$^3$ in rats (calculated using the following formula: [length×width$^2$]/2). The day of the first injection animals were randomized into different groups (6 or 8 animals per group) and DPV1047-BCH-SN38 dissolved in saline was delivered by bolus intravenous injection (i.v.) in the lateral tail vein at 10 µL/g (Table 7).

During the course of the experiment clinical signs, body weight and tumor size were controlled twice a week. The percentage ratio of the mean tumor volume of drug treated versus vehicle treated groups (T/C×100%) and the tumor growth inhibition (TGI %) defined as 100−T/C(%) were used to evaluate treatment efficacy.

The minimal T/C % reflects the maximal tumor growth inhibition achieved.

The efficacy of the DPV1047-BCH-SN38 conjugate in the different tumor models is summarized in Table 7.

TABLE 7

Assessment of the efficacy of the DPV1047-BCH-SN38 conjugate in different human tumor models intradermaly or subcutaneously implanted into rodents.

| Tumor type | Tumor model | Route/Schedule | Doses (µmol/kg) | Optimal T/C % (Day) | TGI % |
|---|---|---|---|---|---|
| Breast | MDA-MB-231 (mice) | i.v. Q2D3 × 3 W | 12.5 | 34.1 (58)* | 65.9 |
|  |  |  | 25 | 30.1 (51)*** | 69.9 |
| Lung | NCI-H460 (mice) | i.v. Q2D3 × 3 W | 12.5 | 47.5 (24)*** | 52.5 |
|  |  |  | 25 | 22.9 (24)*** | 77.1 |
| Colon | HCT 116 (mice) | i.v. Q2D3 × 3 W | 25 | 3.4 (25)*** | 96.6 |
|  | HT-29 (mice) | i.v. Q4D × 3 | 12.5 | 66.8 (38) | 33.2 |
|  |  |  | 25 | 39.2 (31)*** | 60.8 |
|  | LS 174T (rats) | i.v. Q4D × 5 | 10 | 47.2 (35)*** | 52.8 |
|  |  |  | 20 | 42.8 (35)*** | 57.2 |

*$p < 0.05$,
***$p < 0.001$ versus control (Dunnett test)
Day = day when minimal T/C is reached The DPV1047-BCH-SN38 (=DPV1047-linker #5-SN38) conjugate exhibited a significant level of antitumoral activity in all colorectal, lung and breast cancer models tested, demonstrating that DPV1047-BCH-SN38 has activity in a wide range of human tumors. Moreover, when different doses were tested, a dose dependent efficacy was observed.

VIII Evaluation of the in Vivo Efficacy of the DPV1047-BCH-SN38 Conjugate in Combination with Bevacizumab or 5-Fluorouracil Clinically irinotecan has been shown to have synergistic effects with agents such as 5-fluorouracil (5-FU) (Teva® Pharma) and bevacizumab (Avastin®, Roche) Combination studies were therefore performed to assess the action of DPV1047-BCH-SN38 in combination with these agents. Mice were implanted with HT-29 tumors and treated by intraperitoneal administration (bevacizumab) or bolus intravenous injection (5-FU or DPV1047-BCH-SN38) at 10 µL/g. Experimentally defined suboptimal doses of DPV1047-BCH-SN38, 5-FU and 25 bevacizumab, were administered following the schedules established by Prewett et al., Clin Cancer Res. May; 8(5):994-1003 (2002) and Azrak et al., Clin Cancer Res. February 1;10(3):1121-9. (2004). The T/C ratio was calculated following treatment with either bevacizumab, 5-FU or DPV1047-BCH-SN38. These T/C ratios were used to evaluate the expected T/C for combined treatment with bevacizumab and DPV1047-BCH-SN38, or 5-FU and DPV1047-BCH-SN38 (T/C of DPV1047-BCH-SN38×T/C of bevacizumab or 5-FU). The observed T/C following combination treatment was defined experimentally. The combination index of the two molecules was calculated by dividing the expected T/C by the observed T/C. An index >1 demonstrates a synergistic effect, an index of approximately 1 indicates an additive effect and an index <1 indicates an antagonistic effect. The results of these experiments are summarized in Table 8.

TABLE 8

Assessment of synergistic effect of DPV1047-BCH-SN38 in combination with 5-FU or bevacizumab in the HT-29 tumor model.

| Single treatment | | Reference drug | | Combination therapy | | |
|---|---|---|---|---|---|---|
| DPV1047-BCH-SN38 | | | | | | Optimal |
| Doses (µmol/kg) | T/C % (Day) | Drug (dose, mg/kg) | T/C % | Expected T/C* | Observed T/C | combination index$ |
| 12.5 | 68% (31) | 5-FU (40) | 90% | 61% | 36% | 1.69 |
| 25 | 50% (38) | 5-FU (40) | 94% | 47% | 33% | 1.42 |
| 12.5 | 77% (28) | bevacizumab (2) | 67% | 52% | 48% | 1.08 |
| 25 | 69% (28) | bevacizumab (2) | 67% | 46% | 44% | 1.05 |

*Expected T/C = DPV1047-BCH-SN38 T/C x reference drug T/C;
$Combination index = expected T/C/observed T/C In these experiments, DPV1047-BCH-SN38 increased antitumoral efficacy in combination with either 5-FU or bevacizumab. For 5-FU the combination effect was synergistic (combination index >1), whilst for bevacizumab the combination effect was additive (combination index is approximately 1).

IX Evaluation of the in Vitro and in Vivo Activity of DPV1047-BCH-SN38.TFA Compared with DPV1047-BCH-SN38.HCl The efficacy and toxicity of both DPV1047-BCH-SN38.TFA and DPV1047-BCH-SN38.HCl compounds were then compared.

DPV1047-BCH-SN38 hydrochloride (DPV1047-BCH-SN38.HCl) was formed by ion-exchange chromatography of DPV1047-BCH-SN38.TFA. Amberlite IRA-410 ion-exchange resin (475 g) (Fluka) was suspended in HCl 2N for 30 min. The resin was then packed on a column and washed with water. 24 g of DPV1047-BCH-SN38.TFA were dissolved in 125 mL of water, loaded onto the column and eluted with water. The concentration of DPV1047-BCH-SN38.HCl in the different fractions was determined by UV absorbance at 364 nm, using an HIACHI U-2000 Spectrophotometer. Relevant fractions were then pooled, frozen and lyophilized. DPV1047-BCH-SN38.HCl conjugate was then stored at −20° C. under argon.

No difference in efficacy was observed between the two salt forms of DPV1047-BCH-SN38; in vitro cytotoxicity and in vivo efficacy studies in the NCI-H460 lung adenocarcinoma model (ATCC Number: HTB-177) confirmed that DPV1047-BCH-SN38.HCl retained activity with an in vivo optimal T/C of 22.9% and 18.4% for DPV1047-BCH-SN38.TFA and DPV1047-BCH-SN38.HCl respectively (see Table 9).

TABLE 9

Assessment of in vitro ($IC_{50}$) and in vivo efficacy of DPV1047-BCH-SN38•TFA and DPV1047-BCH-SN38•HCl

| | In vitro cytotoxicity $IC_{50}$ (µM) | In vivo efficacy (25 µmol/kg) | |
|---|---|---|---|
| Compound | NCI-H460 1 h exposure + 48 h post-incubation | Optimal T/C % (Day) | TGI % |
| DPV1047-BCH-SN38•TFA | 165 | 18.4 (27)*** | 81.6 |
| DPV1047-BCH-SN38•HCl | 173 | 22.9 (24)*** | 77.1 |

**p < 0.01,
***p < 0.001 versus control (Dunnett test)

X Evaluation of DPV1047-BCH-SN38 Solubility

The solubility of DPV1047-BCH-SN38 (=DPV1047-linker #5-SN38), in water, was found to be much greater than that of either SN38 or irinotecan: DPV1047-BCH-SN38.HCl≧1 g/mL, irinotecan≦2.5 mg/mL and SN38≦5 µg/mL.

XI Evaluation of the Stability and in Vitro Efficacy of a Range of CPP-Linker Camptothecin Derivatives Comparative toxicokinetic studies in the dog have shown that the stability of the linker between the DPV1047 and SN38 correlates with an increase in the plasma AUC of SN38 (See Example VI).

Studies have therefore been performed to evaluate the in vitro stability of different CPP-linker-camptothecin derivatives. Conjugates were synthesized with different CPPs, different linkers and two camptothecins: either SN38 or 10-Hydroxycamptothecin.

CPP-Linker-SN38 Conjugates:
DPV1047-linker #5-SN38
DPV1047-linker #1-SN38
Penetratin-linker #5-SN38
Penetratin-linker #1-SN38
DPV7-linker #5-SN38
Tat-linker #5-SN38
$DPV1047_D$-linker #5-SN38
$DPV51_D$-linker #5-SN38
CPP-Linker-10-Hydroxycamptothecin Conjugates:
Penetratin-linker #5-10-Hydroxycamptothecin
Penetratin-linker #1-10-Hydroxycamptothecin (described in PCT patent application No WO 00/01417)
DPV1047-linker #5-10-Hydroxycamptothecin
DPV1047-linker #1-10-Hydroxycamptothecin
Tat-linker #4-10-Hydroxycamptothecin
Tat-linker #7-10-Hydroxycamptothecin As in Example II, the stability of these conjugates was tested in either human or dog plasma. Following incubation at 37° C., samples were analyzed after a TFA acetonitrile extraction by the HPLC fluorescence method described in Example II. The in vitro cytotoxicity ($IC_{50}$) of these compounds was also evaluated.

Cytotoxic evaluation was performed by seeded cells for 24 h prior to the addition of the therapeutic compound. Cells were incubated for 48 h (37° C.) with different dilutions of the therapeutic compound. Cell viability was then assessed using the WST-1 assay (Roche). The results are expressed as mean cytotoxic concentrations (IC$_{50}$ value or molar concentration that inhibits 50% of cell viability) that were estimated from sigmoid regression, using Graph Pad Prism 3.02 software.

Two Cell Lines Were Used in the Study:

HCT 116 (ATCC #: CCL-247): human epithelial colon carcinoma cells. Cells were cultured in Mc Coy's 5a medium+1.5 mM L-glutamine and 10% fetal bovine serum. Cells were plated at a density of 8000 cells/well in 96-well plates.

NCI-H460 (ATCC#: HTB-177): human epithelial lung carcinoma cells. Cells were cultured in RPMI 1640+ glutamax and 10% of fetal bovine serum. Cells were plated at a density of 10,000 cells/well in 96-well plates.

CPP-Linker-SN38 Conjugates:

As shown in Table 10, DPV1047-linker #5-SN38 was the most stable conjugate (half life time of 360 mins and 260 mins in human and dog plasma, respectively), with a stability consistent with that observed earlier (See Example II). In both the dog and human plasma, which ever CPP was coupled to SN38, the CPP-linker #5-SN38 conjugate was always more stable than the CPP-linker #1-SN38 conjugate, confirming that the linker #5 (=BCH) was more stable than linker #1.

TABLE 10

Half life time (in minutes) of SN38 conjugates in plasma at 37° C.

| CPP-linker-SN38 conjugates | Human Plasma Half life time (min) | Dog Plasma Half life time (min) |
|---|---|---|
| DPV1047-linker #5-SN38 | 360 | 260 |
| DPV1047-linker #1-SN38 | <3 | 11.3 |
| Penetratin-linker #5-SN38 | 60 | 150 |
| Penetratin-linker #1-SN38 | <3 | 16.5 |
| DPV7-linker #5-SN38 | 162 | 112 |
| Tat-linker #5-SN38 | 335 | 122 |

The in vitro cytotoxicity of the most stable compounds (containing linker #5) was evaluated to determine whether the cytotoxic nature of these compounds was retained. Table 11 confirms that all the CPP-linker #5-SN38 conjugates retain cytotoxic activity equivalent to that of SN38, in the two cell lines tested.

TABLE 11

Drug concentration that inhibits 50% of cell viability (IC$_{50}$) in two different cell lines after a 48-h of continuous exposure. Data are expressed in nM and represent the mean value of three independent experiments.

| Cell lines | DPV1047-linker #5-SN38 | Penetratin-linker #5-SN38 | Tat-linker #5-SN38 | DPV7-linker #5-SN38 | SN38 |
|---|---|---|---|---|---|
| HCT 116 | 24 | 57 | 29 | 71 | 7 |
| NCI-H460 | 40 | 53 | 42 | 53 | 22 |

The in vitro plasma stability and cytotoxicity of CPP-linker #5-SN38 conjugates with the CPP in a D conformation was also evaluated. As shown in Table 12 the stability of both CCP-linker #5-SN38 D-isoform conjugates is significantly higher than that observed for CPP-linker #1-SN38 conjugates (see Table 10). The stability of the CCP-linker #5-SN38 D-isoform conjugates although having a half life time greater than 100 minutes in human plasma are less stable that the DPV1047-linker #5-SN38 conjugate. Results are shown in Table 12 below.

TABLE 12

Half life time (in minutes) of SN38 conjugates in plasma at 37° C.

| CPP-linker #5-SN38 conjugates | Human Plasma Half life time (min) | Dog Plasma Half life time (min) |
|---|---|---|
| DPV1047-linker #5-SN38 | 382 | 240 |
| DPV51(D)-linker #5-SN38 | 267 | 175 |
| DPV1047(D)-linker #5-SN38 | 110 | 165 |

The in vitro cytotoxicity of these conjugates was evaluated to determine whether the cytotoxic nature of these compounds was retained. Table 13 confirms that the two CPP-linker #5-SN38 D-isoform conjugates retain cytotoxic activity equivalent to that of DPV 1047-linker #5-SN38. Results are shown in Table 13 below.

TABLE 13

Drug concentration that inhibits 50% of cell viability (IC$_{50}$) after a 48 h of continuous exposure. Data are expressed in nM.

| Cell lines | DPV1047-linker #5-SN38 | DPV51$_{(D)}$-linker #5-SN38 | DPV1047$_{(D)}$-linker #5-SN38 |
|---|---|---|---|
| HCT 116 | 29 | 61 | 23 |

CPP-Linker-10-Hydroxycamptothecin Conjugates:

The stability of different CPP-linker combinations was also tested with 10-Hydroxycamptothecin. As with the CPP-linker #5-SN38 conjugate CPP-linker #5-10-Hydroxycamptothecin conjugates were always more stable than CPP-linker #1-10-Hydroxycamptothecin conjugates. As observed for DPV1047-linker #5-SN38, the stability of the DPV1047-linker #5-10-Hydroxycamptothecin conjugate was greater than the other CPP-linker #5-10-Hydroxycamptothecin conjugates in both human and dog plasma. Results are shown in Table 14 below.

TABLE 14

Half life time (in minutes) of 10-Hydroxycamptothecin conjugates in plasma at 37° C.

| CPP-linker-10-Hydroxycamptothecin conjugates | Human Plasma Half life time (min) | Dog Plasma Half life time (min) |
|---|---|---|
| DPV1047-linker #5-10 Hydroxycamptothecin | 214 | 180 |
| DPV1047-linker #1-10 Hydroxycamptothecin | <3 | 3 |
| Penetratin-linker #5-10 Hydroxycamptothecin | 32 | 110 |
| Penetratin-linker #1-10 Hydroxycamptothecin | <3 | 6 |
| Tat-linker #4-10 Hydroxycamptothecin | 7.3 | 20 |

The in vitro cytotoxicity of the most stable compounds (containing linker #5) was evaluated to determine whether the cytotoxic nature of these compounds was retained. Table 15 confirms that all the CPP-linker #5-10 Hydroxycamptothecin conjugates showed a similar activity, slightly lower, but equivalent to that of 10 Hydroxycamptothecin, for both cell lines tested.

TABLE 15

Drug concentration that inhibits 50% of cell viability ($IC_{50}$) in two different cell lines after a 48 h of continuous exposure. Data are expressed in nM and represent the mean value of three independent experiments.

| Cell lines | DPV1047-linker #5-10 Hydroxycamptothecin | Penetratin-linker #5-10 Hydroxycamptothecin | Tat-linker #4-10 Hydroxycamptothecin | Tat-linker #7-10 Hydroxycamptothecin | 10-Hydroxycamptothecin |
|---|---|---|---|---|---|
| HCT 116 | 185 | 194 | 238 | 158 | 64 |
| NCI-H460 | 112 | 161 | 87 | 127 | 21 |

Linker #4 and #5 show greater stability than linker #1 with all the CPP conjugates tested. The stability of these linker #5 was also greater than linker #1 for both SN38 and 10-Hydroxycamptothecin derivatives.

---

The invention claimed is:
1. A conjugate comprising at least one camptothecin, wherein said conjugate has the following formula (VI):

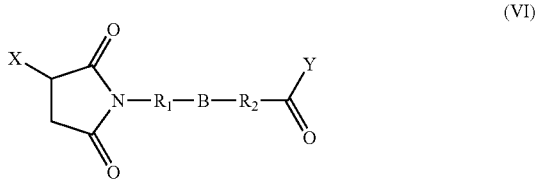

wherein X represents a cell penetrating peptide (CPP), which is attached to the remainder of the conjugate by a thioether bond, wherein the cell penetrating peptide comprises an amino acid sequence selected from the group consisting of:
DPV3 (SEQ ID NO: 1): Arg Lys Lys Arg Arg Arg Glu Ser Arg Lys Lys Arg Arg Arg Glu Ser
DPV6 (SEQ ID NO: 2): Gly Arg Pro Arg Glu Ser Gly Lys Lys Arg Lys Arg Lys Arg Leu Lys Pro
DPV7 (SEQ ID NO: 3): Gly Lys Arg Lys Lys Lys Gly Lys Leu Gly Lys Lys Arg Asp Pro
DPV7b (SEQ ID NO: 4): Gly Lys Arg Lys Lys Lys Gly Lys Leu Gly Lys Lys Arg Pro Arg Ser Arg
DPV10 (SEQ ID NO: 5): Ser Arg Arg Ala Arg Arg Ser Pro Arg His Leu Gly Ser Gly
DPV3/10 (SEQ ID NO: 6): Arg Lys Lys Arg Arg Arg Glu Ser Arg Arg Ala Arg Arg Ser Pro Arg His Leu
DPV10/6 (SEQ ID NO: 7): Ser Arg Arg Ala Arg Arg Ser Pro Arg Glu Ser Gly Lys Lys Arg Lys Arg Lys Arg
DPV1047 (SEQ ID NO: 8): Val Lys Arg Gly Leu Lys Leu Arg His Val Arg Pro Arg Val Thr Arg Met Asp Val
DPV1048 (SEQ ID NO: 9): Val Lys Arg Gly Leu Lys Leu Arg His Val Arg Pro Arg Val Thr Arg Asp Val
DPV15 (SEQ ID NO: 10): Leu Arg Arg Glu Arg Gln Ser Arg Leu Arg Arg Glu Arg Gln Ser Arg and
DPV15b (SEQ ID NO: 11): Gly Ala Tyr Asp Leu Arg Arg Arg Glu Arg Gln Ser Arg Leu Arg Arg Arg Glu Arg Gln Ser Arg;
Y represents the camptothecin and is represented by:

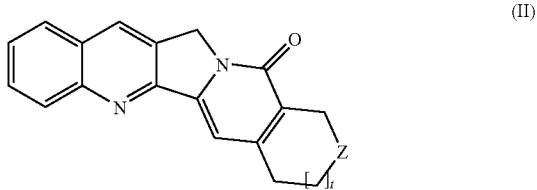

wherein t is 0, 1 or 2 and Z is a —COO— group or a substituted or unsubstituted divalent alkyl group;
Y is attached to the remainder of the conjugate by an ester bond, a carbonyl-disulfide bond or a carboxy-thioester bond;
B is a cyclo($C_3$—$C_8$)alkyl,
$R_1$ is a ($C_1$—$C_8$) alkyl, optionally interrupted by at least one cycloalkyl group, and optionally interrupted by at least one divalent radical selected from —CONR'— and —NR"OC(O)—, wherein R' and R" independently from each other are selected from hydrogen and ($C_1$—$C_8$) alkyl;

and $R_2$ is a ($C_1$—$C_8$) alkyl interrupted by at least one cycloalkyl group, said ($C_1$—$C_8$) alkyl optionally interrupted by at least one divalent radical selected from —OC(O)—, —$CO_2$—, —CONR'—, —NR'CO—, —OC(O)NR'—, and —NR"C(O)$_2$—, wherein R' and R" independently from each other are selected from hydrogen and ($C_1$—$C_8$) alkyl.

2. The conjugate according to claim 1, wherein Y is represented by the following formula (III):

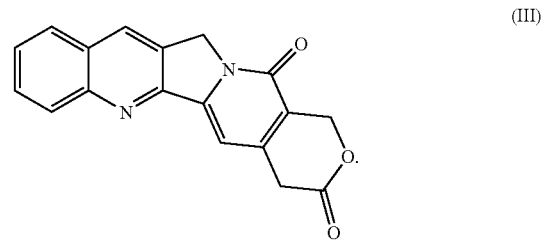 [SMILES: O=C1Cc2cc3n(c(=O)c2CO1)Cc1cc2ccccc2nc1-3]

3. The conjugate according to claim 2, wherein Y is represented by the following formula (IV):

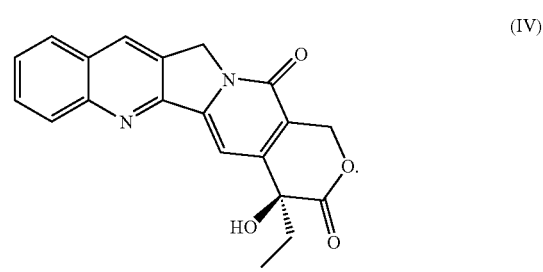 [SMILES: CC[C@@]1(O)C(=O)OCc2c1cc1n(c2=O)Cc2cc3ccccc3nc2-1]

4. The conjugate according to claim 1, wherein the camptothecin is selected from the group consisting of irinotecan, topotecan, GI-1472 11C, SN38, 7-hydroxymethyl camptothecin, 9-aminocamptothecin, 7-aminomethyl camptothecin, 10-hydroxycamptothecin and (20S)-camptothecin.

5. The conjugate according to claim 1, wherein —$R_1$ is —$CH_2$— or —$CH_2CH_2$—.

6. The conjugate according to claim 1, wherein camptothecin is linked covalently to the cell penetrating peptide with a linker resulting from a compound selected from:
4-[(N-maleimidomethyl)cyclohexane-1-carboxy-6-amidohexanecarboxamido methyl]cyclohexanecarboxylic acid and
4-[((N-maleimidomethyl)cyclohexanecarboxamido)methyl]cyclohexanecarboxylic acid.

7. The conjugate according to claim 1, wherein the peptide is derived from a human heparin binding protein and capable of penetrating into a cell or tissue and comprises:
- DPV1047 (SEQ ID NO: 8): Val Lys Arg Gly Leu Lys Leu Arg His Val Arg Pro Arg Val Thr Arg Met Asp Val.

8. The conjugate according to claim 7, wherein the peptide presents a cysteine at the C or N position.

9. The conjugate according to claim 1, which is selected from the group consisting of:

(SEQ ID NO:53)
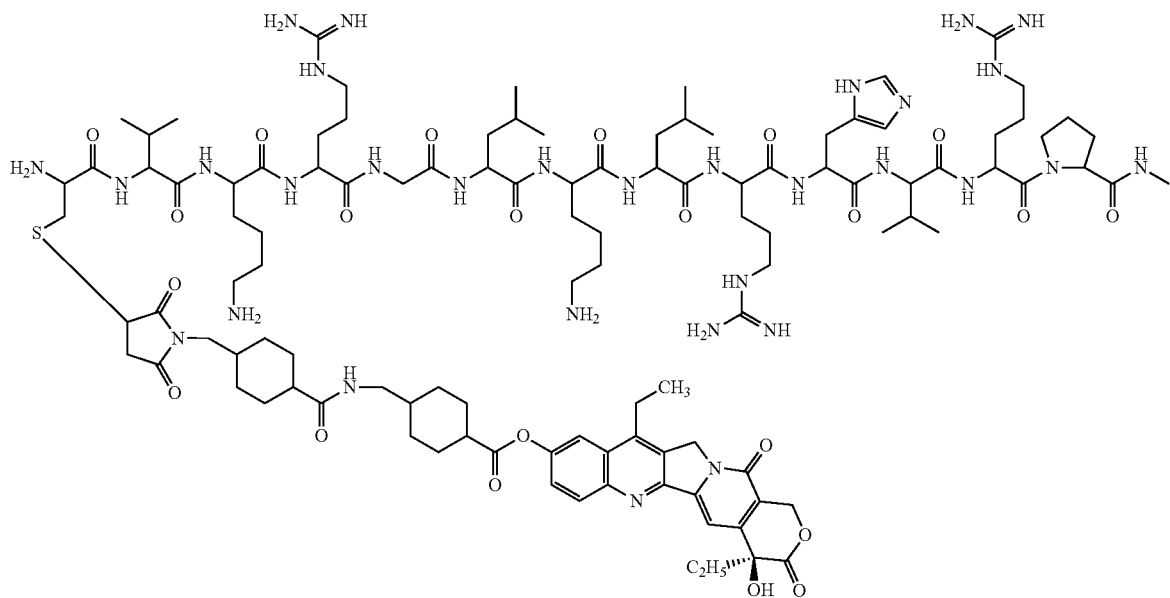
(SEQ ID NO:53)
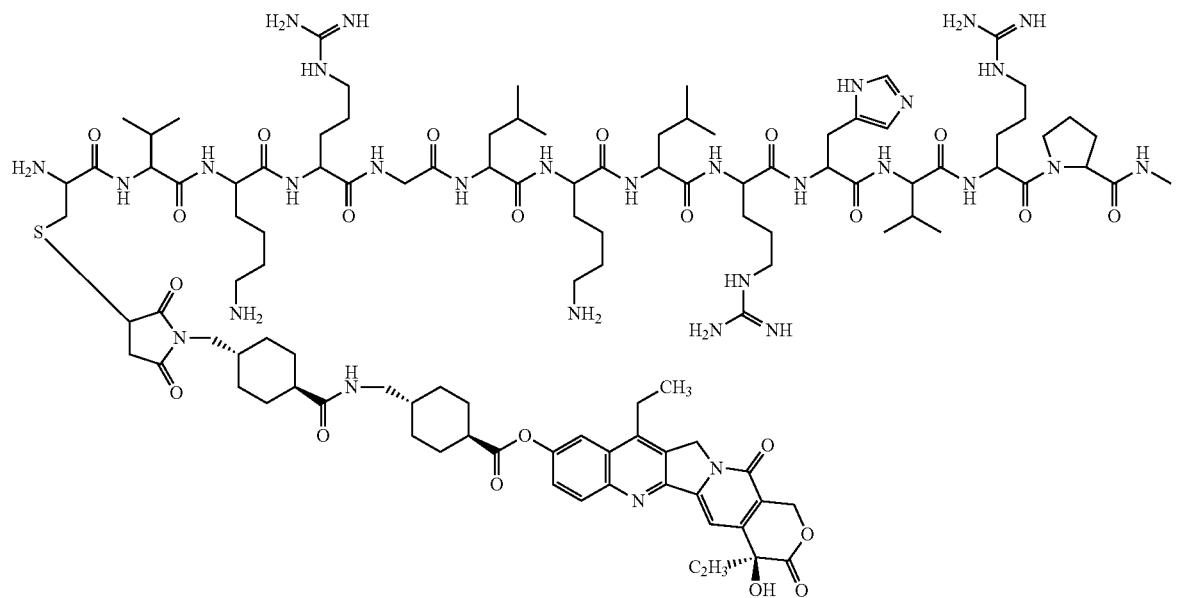

-continued

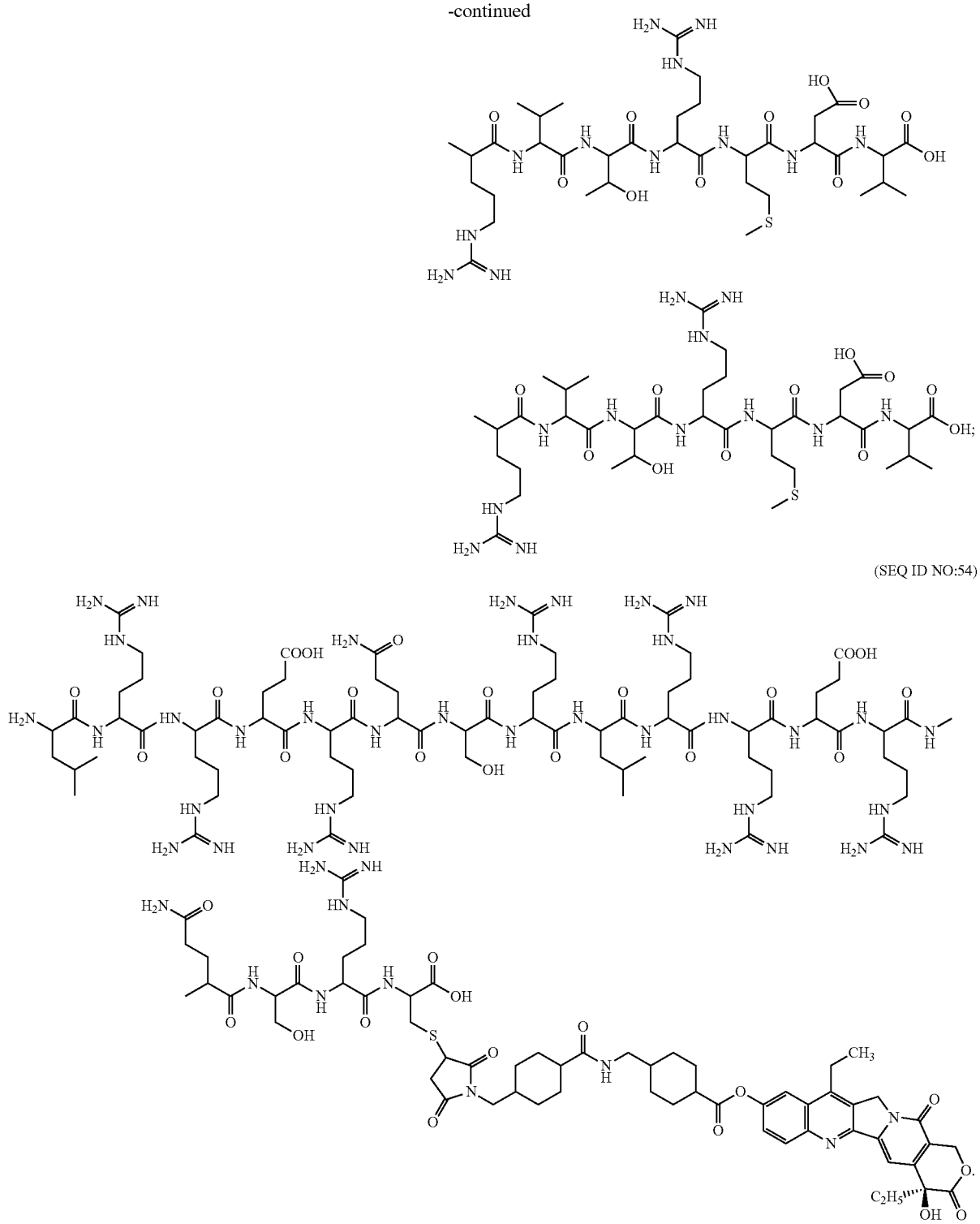

(SEQ ID NO:54)

10. A pharmaceutical composition comprising a pharmaceutically acceptable carrier and at least one conjugate of claim 1.

11. A method for treating cancer comprising administering an effective amount of the pharmaceutical composition according to claim 10 to a subject in need thereof, wherein said cancer is colon cancer, small cell lung cancer, non-small cell lung cancer, bronchic cancer, pancreatic cancer, ovarian cancer, breast cancer, prostate cancer, liver cancer, head cancer, stomach cancer, neck cancer, bladder cancer, non-Hodgkin's lymphoma, melanoma, leukaemia, neuroblastoma, or glioblastoma.

12. The method of claim 11, wherein the composition is administered orally, intra-cranially, intra-spinally, enterally or parenterally.

13. The method of claim 11, wherein the composition is administered simultaneously or sequentially with other therapeutic regimens or agents.

14. The method of claim 11, comprising a simultaneous or sequential administration with other therapeutic regimens or agents, selected from the group consisting of 5-fluorouracil, leucovorin, oxaliplatine, capecitabine, vincristine, celebrex, temozolomide, selenium, thalidomide, cetuximab, gemcitabine, docetaxel, 3-AP, carboplatine, bortezomib, bevacizumab, sorafenib, cisplatin, gefitinib, flavopiridol, elvorine, carboplatin, amrubicin, trastuzumab, pemetrexed, erlotinib, mitomycin C, AMG706, panitumumab, paclitaxel, raltitrexed, imatinib, abciximab, infliximab, palivizumab, rituximab, gemtuzumab ozogamicin, alemtuzumab, and ibritumomab tiuxetan.

* * * * *

UNITED STATES PATENT AND TRADEMARK OFFICE
CERTIFICATE OF CORRECTION

PATENT NO. : 8,410,045 B2  
APPLICATION NO. : 12/295508  
DATED : April 2, 2013  
INVENTOR(S) : Matthieu Michel et al.

It is certified that error appears in the above-identified patent and that said Letters Patent is hereby corrected as shown below:

In the Claims:

At the top of column 90, delete the second instance of the structure

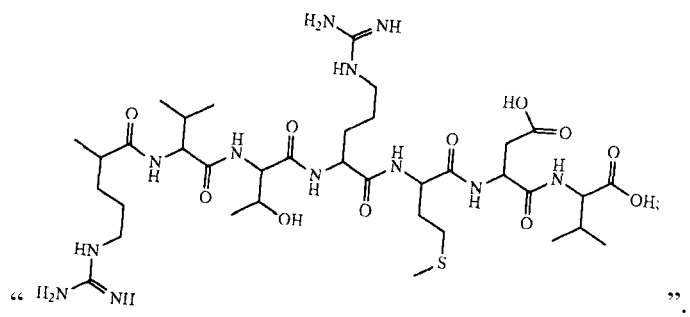

" ".

At column 91, line 4, delete "a" before the word "simultaneous".

Signed and Sealed this  
Sixteenth Day of July, 2013

Teresa Stanek Rea  
*Acting Director of the United States Patent and Trademark Office*

SEQUENCE LISTING

```
<160> NUMBER OF SEQ ID NOS: 55

<210> SEQ ID NO 1
<211> LENGTH: 16
<212> TYPE: PRT
<213> ORGANISM: Homo sapiens

<400> SEQUENCE: 1

Arg Lys Lys Arg Arg Arg Glu Ser Arg Lys Arg Arg Arg Glu Ser
1               5                   10                  15

<210> SEQ ID NO 2
<211> LENGTH: 17
<212> TYPE: PRT
<213> ORGANISM: Homo sapiens

<400> SEQUENCE: 2

Gly Arg Pro Arg Glu Ser Gly Lys Lys Arg Lys Arg Lys Arg Leu Lys
1               5                   10                  15
Pro

<210> SEQ ID NO 3
<211> LENGTH: 15
<212> TYPE: PRT
<213> ORGANISM: Homo sapiens

<400> SEQUENCE: 3

Gly Lys Arg Lys Lys Lys Gly Lys Leu Gly Lys Lys Arg Asp Pro
1               5                   10                  15

<210> SEQ ID NO 4
<211> LENGTH: 17
<212> TYPE: PRT
<213> ORGANISM: Homo sapiens

<400> SEQUENCE: 4

Gly Lys Arg Lys Lys Lys Gly Lys Leu Gly Lys Lys Arg Pro Arg Ser
1               5                   10                  15
Arg

<210> SEQ ID NO 5
<211> LENGTH: 14
<212> TYPE: PRT
<213> ORGANISM: Homo sapiens

<400> SEQUENCE: 5

Ser Arg Arg Ala Arg Arg Ser Pro Arg His Leu Gly Ser Gly
```

```
<210> SEQ ID NO 6
<211> LENGTH: 18
<212> TYPE: PRT
<213> ORGANISM: Homo sapiens

<400> SEQUENCE: 6

Arg Lys Lys Arg Arg Glu Ser Arg Arg Ala Arg Arg Ser Pro Arg
1               5                   10                  15

His Leu

<210> SEQ ID NO 7
<211> LENGTH: 19
<212> TYPE: PRT
<213> ORGANISM: Homo sapiens

<400> SEQUENCE: 7

Ser Arg Arg Ala Arg Arg Ser Pro Arg Glu Ser Gly Lys Lys Arg Lys
1               5                   10                  15

Arg Lys Arg

<210> SEQ ID NO 8
<211> LENGTH: 19
<212> TYPE: PRT
<213> ORGANISM: Homo sapiens

<400> SEQUENCE: 8

Val Lys Arg Gly Leu Lys Leu Arg His Val Arg Pro Arg Val Thr Arg
1               5                   10                  15

Met Asp Val

<210> SEQ ID NO 9
<211> LENGTH: 18
<212> TYPE: PRT
<213> ORGANISM: Homo sapiens

<400> SEQUENCE: 9

Val Lys Arg Gly Leu Lys Leu Arg His Val Arg Pro Arg Val Thr Arg
1               5                   10                  15

Asp Val

<210> SEQ ID NO 10
<211> LENGTH: 16
<212> TYPE: PRT
<213> ORGANISM: Homo sapiens

<400> SEQUENCE: 10

Leu Arg Arg Glu Arg Gln Ser Arg Leu Arg Arg Glu Arg Gln Ser Arg
1               5                   10                  15

<210> SEQ ID NO 11
<211> LENGTH: 22
<212> TYPE: PRT
<213> ORGANISM: Homo sapiens

<400> SEQUENCE: 11

Gly Ala Tyr Asp Leu Arg Arg Glu Arg Gln Ser Arg Leu Arg Arg
1               5                   10                  15

Arg Glu Arg Gln Ser Arg
            20
```

```
<210> SEQ ID NO 12
<211> LENGTH: 21
<212> TYPE: PRT
<213> ORGANISM: Homo sapiens

<400> SEQUENCE: 12

Thr Arg Ser Ser Arg Ala Gly Leu Gln Phe Pro Val Gly Arg Val His
1               5                   10                  15

Arg Leu Leu Arg Lys
            20

<210> SEQ ID NO 13
<211> LENGTH: 30
<212> TYPE: PRT
<213> ORGANISM: Homo sapiens

<400> SEQUENCE: 13

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 14
<211> LENGTH: 21
<212> TYPE: PRT
<213> ORGANISM: Homo sapiens

<400> SEQUENCE: 14

Lys Gly Ser Trp Tyr Ser Met Arg Lys Met Ser Met Lys Ile Arg Pro
1               5                   10                  15

Phe Phe Pro Gln Gln
            20

<210> SEQ ID NO 15
<211> LENGTH: 20
<212> TYPE: PRT
<213> ORGANISM: Homo sapiens

<400> SEQUENCE: 15

Lys Thr Arg Tyr Tyr Ser Met Lys Lys Thr Thr Met Lys Ile Ile Pro
1               5                   10                  15

Phe Asn Arg Leu
            20

<210> SEQ ID NO 16
<211> LENGTH: 20
<212> TYPE: PRT
<213> ORGANISM: Homo sapiens

<400> SEQUENCE: 16

Arg Gly Ala Asp Tyr Ser Leu Arg Ala Val Arg Met Lys Ile Arg Pro
1               5                   10                  15

Leu Val Thr Gln
            20

<210> SEQ ID NO 17
<211> LENGTH: 24
<212> TYPE: PRT
<213> ORGANISM: Homo sapiens

<400> SEQUENCE: 17

Leu Gly Thr Tyr Thr Gln Asp Phe Asn Lys Phe His Thr Phe Pro Gln
1               5                   10                  15
```

```
Thr Ala Ile Gly Val Gly Ala Pro
            20

<210> SEQ ID NO 18
<211> LENGTH: 12
<212> TYPE: PRT
<213> ORGANISM: Homo sapiens

<400> SEQUENCE: 18

Thr Ser Pro Leu Asn Ile His Asn Gly Gln Lys Leu
1               5                   10

<210> SEQ ID NO 19
<211> LENGTH: 12
<212> TYPE: PRT
<213> ORGANISM: Homo sapiens

<400> SEQUENCE: 19

Asn Ser Ala Ala Phe Glu Asp Leu Arg Val Leu Ser
1               5                   10

<210> SEQ ID NO 20
<211> LENGTH: 30
<212> TYPE: PRT
<213> ORGANISM: Homo sapiens

<400> SEQUENCE: 20

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 21
<211> LENGTH: 16
<212> TYPE: PRT
<213> ORGANISM: Homo sapiens

<400> SEQUENCE: 21

Ala Ala Val Ala Leu Leu Pro Ala Val Leu Leu Ala Leu Leu Ala Pro
1               5                   10                  15

<210> SEQ ID NO 22
<211> LENGTH: 10
<212> TYPE: PRT
<213> ORGANISM: Homo sapiens

<400> SEQUENCE: 22

Val Pro Met Leu Lys Pro Met Leu Lys Glu
1               5                   10

<210> SEQ ID NO 23
<211> LENGTH: 18
<212> TYPE: PRT
<213> ORGANISM: Homo sapiens

<400> SEQUENCE: 23

Lys Leu Ala Leu Lys Leu Ala Leu Lys Ala Leu Lys Ala Ala Leu Lys
1               5                   10                  15

Leu Ala

<210> SEQ ID NO 24
<211> LENGTH: 27
<212> TYPE: PRT
<213> ORGANISM: Homo sapiens
```

-continued

```
<400> SEQUENCE: 24

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 25
<211> LENGTH: 16
<212> TYPE: PRT
<213> ORGANISM: Homo sapiens

<400> SEQUENCE: 25

Ala Ala Val Ala Leu Leu Pro Ala Val Leu Leu Ala Leu Leu Ala Pro
1               5                   10                  15

<210> SEQ ID NO 26
<211> LENGTH: 9
<212> TYPE: PRT
<213> ORGANISM: Homo sapiens

<400> SEQUENCE: 26

Val Gln Arg Lys Arg Gln Lys Leu Met
1               5

<210> SEQ ID NO 27
<211> LENGTH: 21
<212> TYPE: PRT
<213> ORGANISM: Homo sapiens

<400> SEQUENCE: 27

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 28
<211> LENGTH: 15
<212> TYPE: PRT
<213> ORGANISM: Homo sapiens

<400> SEQUENCE: 28

Ser Asp Leu Trp Glu Met Met Met Val Ser Leu Ala Cys Gln Tyr
1               5                   10                  15

<210> SEQ ID NO 29
<211> LENGTH: 16
<212> TYPE: PRT
<213> ORGANISM: Homo sapiens

<400> SEQUENCE: 29

Arg Gln Ile Lys Ile Trp Phe Gln Asn Arg Arg Met Lys Trp Lys Lys
1               5                   10                  15

<210> SEQ ID NO 30
<211> LENGTH: 7
<212> TYPE: PRT
<213> ORGANISM: Homo sapiens

<400> SEQUENCE: 30

Arg Arg Met Lys Trp Lys Lys
1               5

<210> SEQ ID NO 31
<211> LENGTH: 7
```

```
<212> TYPE: PRT
<213> ORGANISM: Homo sapiens

<400> SEQUENCE: 31

Arg Arg Arg Arg Arg Arg Arg
1               5

<210> SEQ ID NO 32
<211> LENGTH: 9
<212> TYPE: PRT
<213> ORGANISM: Homo sapiens

<400> SEQUENCE: 32

Arg Arg Arg Arg Arg Arg Arg Arg Arg
1               5

<210> SEQ ID NO 33
<211> LENGTH: 16
<212> TYPE: PRT
<213> ORGANISM: Homo sapiens

<400> SEQUENCE: 33

Arg Val Ile Arg Val Trp Phe Gln Asn Lys Arg Cys Lys Asp Lys Lys
1               5                   10                  15

<210> SEQ ID NO 34
<211> LENGTH: 28
<212> TYPE: PRT
<213> ORGANISM: Homo sapiens

<400> SEQUENCE: 34

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 35
<211> LENGTH: 18
<212> TYPE: PRT
<213> ORGANISM: Homo sapiens

<400> SEQUENCE: 35

Leu Leu Ile Ile Leu Arg Arg Arg Ile Arg Lys Gln Ala His Ala His
1               5                   10                  15

Ser Lys

<210> SEQ ID NO 36
<211> LENGTH: 18
<212> TYPE: PRT
<213> ORGANISM: Homo sapiens

<400> SEQUENCE: 36

Val Arg Leu Pro Pro Pro Val Arg Leu Pro Pro Pro Val Arg Leu Pro
1               5                   10                  15

Pro Pro

<210> SEQ ID NO 37
<211> LENGTH: 7
<212> TYPE: PRT
<213> ORGANISM: Homo sapiens

<400> SEQUENCE: 37

Pro Lys Lys Lys Arg Lys Val
1               5
```

<210> SEQ ID NO 38
<211> LENGTH: 18
<212> TYPE: PRT
<213> ORGANISM: Homo sapiens

<400> SEQUENCE: 38

Arg Gly Gly Arg Leu Ser Tyr Ser Arg Arg Phe Ser Thr Ser Thr
1               5                   10                  15
Gly Arg

<210> SEQ ID NO 39
<211> LENGTH: 10
<212> TYPE: PRT
<213> ORGANISM: Homo sapiens

<400> SEQUENCE: 39

Arg Arg Leu Ser Tyr Ser Arg Arg Arg Phe
1               5                   10

<210> SEQ ID NO 40
<211> LENGTH: 17
<212> TYPE: PRT
<213> ORGANISM: Homo sapiens

<400> SEQUENCE: 40

Ala Trp Ser Phe Arg Val Ser Tyr Arg Gly Ile Ser Tyr Arg Ser
1               5                   10                  15
Arg

<210> SEQ ID NO 41
<211> LENGTH: 14
<212> TYPE: PRT
<213> ORGANISM: Homo sapiens

<400> SEQUENCE: 41

Tyr Gly Arg Lys Lys Arg Arg Gln Arg Arg Pro Pro Gln
1               5                   10

<210> SEQ ID NO 42
<211> LENGTH: 11
<212> TYPE: PRT
<213> ORGANISM: Homo sapiens

<400> SEQUENCE: 42

Tyr Gly Arg Lys Lys Arg Arg Gln Arg Arg
1               5                   10

<210> SEQ ID NO 43
<211> LENGTH: 9
<212> TYPE: PRT
<213> ORGANISM: Homo sapiens

<400> SEQUENCE: 43

Arg Lys Lys Arg Arg Gln Arg Arg
1               5

<210> SEQ ID NO 44
<211> LENGTH: 13
<212> TYPE: PRT
<213> ORGANISM: Homo sapiens

<400> SEQUENCE: 44

Gly Arg Lys Lys Arg Arg Gln Arg Arg Arg Pro Pro Gln

```
                1               5                  10
```

<210> SEQ ID NO 45
<211> LENGTH: 27
<212> TYPE: PRT
<213> ORGANISM: Homo sapiens

<400> SEQUENCE: 45

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

<210> SEQ ID NO 46
<211> LENGTH: 21
<212> TYPE: PRT
<213> ORGANISM: Homo sapiens

<400> SEQUENCE: 46

```
Ala Gly Tyr Leu Leu Gly Lys Ile Asn Leu Lys Ala Leu Ala Ala Leu
1               5                   10                  15

Ala Lys Lys Ile Leu
            20
```

<210> SEQ ID NO 47
<211> LENGTH: 12
<212> TYPE: PRT
<213> ORGANISM: Homo sapiens

<400> SEQUENCE: 47

```
Gly Trp Thr Leu Asn Ser Ala Gly Tyr Leu Leu Gly
1               5                   10
```

<210> SEQ ID NO 48
<211> LENGTH: 14
<212> TYPE: PRT
<213> ORGANISM: Homo sapiens

<400> SEQUENCE: 48

```
Ile Asn Leu Lys Ala Leu Ala Ala Leu Ala Lys Lys Ile Leu
1               5                   10
```

<210> SEQ ID NO 49
<211> LENGTH: 34
<212> TYPE: PRT
<213> ORGANISM: Homo sapiens

<400> SEQUENCE: 49

```
Asp Ala Ala Thr Ala Thr Arg Gly Arg Ser Ala Ser Arg Pro Thr
1               5                   10                  15

Glu Arg Pro Arg Ala Pro Ala Arg Ser Ala Ser Arg Pro Arg Arg Pro
            20                  25                  30

Val Asp
```

<210> SEQ ID NO 50
<211> LENGTH: 26
<212> TYPE: PRT
<213> ORGANISM: Homo sapiens

<400> SEQUENCE: 50

```
Asp Pro Lys Gly Asp Pro Lys Gly Val Thr Val Thr Val Thr
1               5                   10                  15

Val Thr Gly Lys Gly Asp Pro Lys Pro Asp
```

```
<210> SEQ ID NO 51
<211> LENGTH: 8
<212> TYPE: PRT
<213> ORGANISM: Homo sapiens

<400> SEQUENCE: 51

Lys Arg Gly Leu Lys Leu Arg His
1               5

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      PolyE peptide

<400> SEQUENCE: 52

Glu Glu Glu Glu Glu Glu Glu Glu Glu Glu Glu Glu Glu Glu Glu Glu
1               5                   10                  15

<210> SEQ ID NO 53
<211> LENGTH: 20
<212> TYPE: PRT
<213> ORGANISM: Artificial Sequence
<220> FEATURE:
<223> OTHER INFORMATION: Description of Artificial Sequence: Synthetic
      CPP peptide where Cys residue forms cysteine bond with
      chemical moiety

<400> SEQUENCE: 53

Cys Val Lys Arg Gly Leu Lys Leu Arg His Val Arg Pro Arg Val Thr
1               5                   10                  15

Arg Met Asp Val
            20

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      CPP peptide where Cys residue forms cysteine bond with
      chemical moiety

<400> SEQUENCE: 54

Leu Arg Arg Glu Arg Gln Ser Arg Leu Arg Arg Glu Arg Gln Ser Arg
1               5                   10                  15

Cys

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      PolyE peptide where Cys residue forms cysteine bond
      with chemical moiety

<400> SEQUENCE: 55

Glu Glu Glu Glu Glu Glu Glu Glu Glu Glu Glu Glu Glu Glu Glu Glu
1               5                   10                  15

Cys
```